(12) United States Patent
Santora et al.

(10) Patent No.: US 8,939,933 B2
(45) Date of Patent: Jan. 27, 2015

(54) MANIFOLDS, SYSTEMS, AND METHODS FOR ADMINISTERING REDUCED PRESSURE TO A SUBCUTANEOUS TISSUE SITE

(75) Inventors: Carl Joseph Santora, Helotes, TX (US); Michael E. Manwaring, San Antonio, TX (US); Douglas A. Cornet, San Antonio, TX (US); Justin Alexander Long, San Antonio, TX (US); Larry D. Swain, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 1035 days.

(21) Appl. No.: 12/647,146

(22) Filed: Dec. 24, 2009

(65) Prior Publication Data

US 2010/0168688 A1 Jul. 1, 2010

Related U.S. Application Data

(63) Continuation-in-part of application No. 12/540,934, filed on Aug. 13, 2009, now abandoned, which is a continuation-in-part of application No. 11/807,834, filed on May 29, 2007, now abandoned, which is a (Continued)

(51) Int. Cl.
*A61M 37/00* (2006.01)
*A61M 27/00* (2006.01)
(Continued)

(52) U.S. Cl.
CPC ............... *A61M 27/00* (2013.01); *A61B 17/88* (2013.01); *A61F 2/3662* (2013.01);
(Continued)

(58) Field of Classification Search
USPC ........................................ 604/93.01, 131, 43
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 A1 | 8/1982 |
| AU | 745271 | 4/1999 |

(Continued)

OTHER PUBLICATIONS

Marc G. Jeschke, MD, et al.; "Development of New Reconstructive Techniques: Use of Integra in Combination with Fibrin Glue and Negative-Pressure Therapy for Reconstruction of Acute and chronic Wounds"; Plastic and Reconstructive Surgery, Feb. 2004, vol. 113, No. 2, pp. 525-530.

(Continued)

*Primary Examiner* — Edelmira Bosques

(57) ABSTRACT

Systems, methods, and apparatuses are provided for delivering reduced pressure to a subcutaneous tissue site, such as a bone tissue site. In one instance, a manifold for providing reduced pressure to a subcutaneous tissue includes a longitudinal manifold body formed with at least one purging lumen and a reduced-pressure lumen. The manifold further includes a plurality of manifolding surface features or slits formed on the second, tissue-facing side of the longitudinal manifold body and a plurality of apertures formed in the longitudinal manifold body on the second, tissue-facing side. The plurality of apertures fluidly couple the reduced-pressure lumen and the manifolding surface features or slits. The manifold further includes an end cap fluidly coupling the reduced-pressure lumen and the at least one purging lumen. Other systems, apparatuses, and methods are presented.

9 Claims, 33 Drawing Sheets

Related U.S. Application Data continuation-in-part of application No. 11/724,072, filed on Mar. 13, 2007, now abandoned.

(60) Provisional application No. 60/782,171, filed on Mar. 14, 2006, provisional application No. 61/141,728, filed on Dec. 31, 2008.

(51) Int. Cl.
| | |
|---|---|
| *A61B 17/88* | (2006.01) |
| *A61F 2/36* | (2006.01) |
| *A61M 25/00* | (2006.01) |
| *A61B 17/135* | (2006.01) |
| *A61B 17/80* | (2006.01) |
| *A61F 2/30* | (2006.01) |

(52) U.S. Cl.
CPC ........ *A61M 25/003* (2013.01); *A61M 25/0032* (2013.01); *A61M 25/0068* (2013.01); *A61M 25/0069* (2013.01); *A61M 25/0074* (2013.01); *A61M 25/0082* (2013.01); *A61B 17/1355* (2013.01); *A61B 17/80* (2013.01); *A61F 2/30767* (2013.01); *A61F 2/36* (2013.01); *A61F 2002/30677* (2013.01); *A61F 2002/30785* (2013.01); *A61F 2002/30787* (2013.01); *A61F 2002/30968* (2013.01); *A61F 2002/3611* (2013.01); *A61F 2002/3625* (2013.01); *A61F 2002/368* (2013.01); *A61F 2002/3694* (2013.01); *A61F 2310/00395* (2013.01); *A61F 2310/00592* (2013.01); *A61F 2310/00928* (2013.01); *A61M 25/0009* (2013.01); *A61M 25/007* (2013.01); *A61M 25/0071* (2013.01); *A61M 2025/0003* (2013.01); *A61M 2025/0034* (2013.01); *A61M 2025/0036* (2013.01); *A61M 2025/0076* (2013.01)
USPC ........................... 604/131; 604/93.01; 604/43

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,376,868 A | 4/1968 | Mondiadis | |
| 3,382,867 A | 5/1968 | Reaves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,742,952 A | 7/1973 | Magers et al. | |
| 3,774,611 A | 11/1973 | Tussey et al. | |
| 3,779,243 A | 12/1973 | Tussey et al. | |
| 3,823,716 A | 7/1974 | Hale | |
| 3,826,254 A | 7/1974 | Mellor | |
| 3,867,319 A | 2/1975 | Lundberg | |
| 3,875,941 A | 4/1975 | Adair | |
| 3,957,054 A | 5/1976 | McFarlane | |
| 3,993,080 A | 11/1976 | Loseff | |
| 4,029,104 A | 6/1977 | Kerber | |
| 4,080,970 A | 3/1978 | Miller | |
| 4,096,853 A | 6/1978 | Weigand | |
| 4,139,004 A | 2/1979 | Gonzalez, Jr. | |
| 4,141,361 A | 2/1979 | Snyder | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,250,882 A | 2/1981 | Adair | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,324,262 A | 4/1982 | Hall | |
| 4,329,743 A | 5/1982 | Alexander et al. | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,433,973 A | 2/1984 | Kurtz et al. | |
| 4,437,856 A * | 3/1984 | Valli | 604/29 |
| 4,445,897 A * | 5/1984 | Ekbladh et al. | 604/541 |
| 4,465,485 A | 8/1984 | Kashmer et al. | |
| 4,475,909 A | 10/1984 | Eisenberg | |
| 4,479,792 A | 10/1984 | Lazarus et al. | |
| 4,480,638 A | 11/1984 | Schmid | |
| 4,523,920 A | 6/1985 | Russo | |
| 4,525,166 A | 6/1985 | Leclerc | |
| 4,525,374 A | 6/1985 | Vaillancourt | |
| 4,529,402 A | 7/1985 | Weilbacher et al. | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,572,906 A | 2/1986 | Sparkes et al. | |
| 4,573,965 A | 3/1986 | Russo | |
| 4,579,555 A | 4/1986 | Russo | |
| 4,605,399 A | 8/1986 | Weston et al. | |
| 4,608,041 A | 8/1986 | Nielsen | |
| 4,640,688 A | 2/1987 | Hauser | |
| 4,642,093 A | 2/1987 | Harle | |
| 4,643,719 A | 2/1987 | Garth et al. | |
| 4,655,754 A | 4/1987 | Richmond et al. | |
| 4,664,652 A | 5/1987 | Weilbacher | |
| 4,664,662 A | 5/1987 | Webster | |
| 4,681,570 A | 7/1987 | Dalton | |
| 4,710,165 A | 12/1987 | McNeil et al. | |
| 4,717,379 A * | 1/1988 | Ekholmer | 604/43 |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,830,856 A | 5/1989 | Peppers | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,936,834 A | 6/1990 | Beck et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,981,474 A | 1/1991 | Bopp et al. | |
| 4,985,019 A | 1/1991 | Michelson | |
| 5,013,300 A | 5/1991 | Williams | |
| 5,019,059 A | 5/1991 | Goldberg et al. | |
| 5,034,006 A | 7/1991 | Hosoda et al. | |
| 5,037,397 A | 8/1991 | Kalt et al. | |
| 5,045,056 A | 9/1991 | Behl | |
| 5,086,170 A | 2/1992 | Luheshi et al. | |
| 5,089,606 A | 2/1992 | Cole et al. | |
| 5,092,858 A | 3/1992 | Benson et al. | |
| 5,100,395 A | 3/1992 | Rosenberg | |
| 5,100,396 A | 3/1992 | Zamierowski | |
| 5,102,404 A | 4/1992 | Goldberg et al. | |
| 5,108,364 A | 4/1992 | Takezawa et al. | |
| 5,112,323 A | 5/1992 | Winkler et al. | |
| 5,116,310 A | 5/1992 | Seder et al. | |
| 5,134,994 A | 8/1992 | Say | |

(56) References Cited

U.S. PATENT DOCUMENTS

| | | |
|---|---|---|
| 5,149,331 A | 9/1992 | Ferdman et al. |
| 5,163,905 A | 11/1992 | Don Michael |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,254,084 A | 10/1993 | Geary |
| 5,259,399 A | 11/1993 | Brown |
| 5,261,893 A | 11/1993 | Zamierowski |
| 5,266,071 A | 11/1993 | Elftman |
| 5,278,100 A | 1/1994 | Doan et al. |
| 5,279,550 A | 1/1994 | Habib et al. |
| 5,298,015 A | 3/1994 | Komatsuzaki et al. |
| 5,324,306 A | 6/1994 | Makower et al. |
| 5,342,329 A | 8/1994 | Croquevielle |
| 5,342,376 A | 8/1994 | Ruff |
| 5,344,415 A | 9/1994 | DeBusk et al. |
| 5,358,494 A | 10/1994 | Svedman |
| 5,376,376 A | 12/1994 | Li |
| 5,405,322 A | 4/1995 | Lennox et al. |
| 5,437,622 A | 8/1995 | Carion |
| 5,437,651 A | 8/1995 | Todd et al. |
| 5,443,481 A | 8/1995 | Lee |
| 5,470,316 A | 11/1995 | Tovey et al. |
| 5,527,293 A | 6/1996 | Zamierowski |
| 5,549,579 A | 8/1996 | Batdorf et al. |
| 5,549,584 A | 8/1996 | Gross |
| 5,556,375 A | 9/1996 | Ewall |
| 5,569,184 A | 10/1996 | Crocker et al. |
| 5,591,183 A | 1/1997 | Chin |
| 5,607,388 A | 3/1997 | Ewall |
| 5,634,935 A | 6/1997 | Taheri |
| 5,636,643 A | 6/1997 | Argenta et al. |
| 5,643,589 A | 7/1997 | Chalmers |
| 5,645,081 A | 7/1997 | Argenta et al. |
| 5,676,634 A | 10/1997 | Khouri |
| 5,681,342 A | 10/1997 | Benchetrit |
| 5,713,874 A | 2/1998 | Ferber |
| 5,735,833 A | 4/1998 | Olson |
| 5,738,656 A | 4/1998 | Wagner |
| 5,762,640 A | 6/1998 | Kajiwara et al. |
| 5,820,581 A | 10/1998 | Wolfinbarger, Jr. |
| 5,885,508 A | 3/1999 | Ishida |
| 5,888,544 A | 3/1999 | Gergely et al. |
| 5,908,403 A * | 6/1999 | Bosma et al. ............ 604/43 |
| 5,914,264 A | 6/1999 | Korman |
| 5,916,193 A | 6/1999 | Stevens et al. |
| 5,941,859 A | 8/1999 | Lerman |
| 5,948,020 A | 9/1999 | Yoon et al. |
| RE36,370 E | 11/1999 | Li |
| 5,980,503 A | 11/1999 | Chin |
| 5,984,942 A | 11/1999 | Alden et al. |
| 6,013,054 A | 1/2000 | Jiun Yan |
| 6,042,537 A | 3/2000 | Kaiser |
| 6,071,267 A | 6/2000 | Zamierowski |
| 6,080,243 A | 6/2000 | Insley et al. |
| 6,086,587 A | 7/2000 | Hawk |
| 6,132,415 A | 10/2000 | Finch et al. |
| 6,135,116 A | 10/2000 | Vogel et al. |
| 6,142,982 A | 11/2000 | Hunt et al. |
| 6,153,292 A | 11/2000 | Bell et al. |
| 6,174,306 B1 | 1/2001 | Fleischmann |
| 6,231,551 B1 * | 5/2001 | Barbut ............ 604/236 |
| 6,241,747 B1 | 6/2001 | Ruff |
| 6,285,903 B1 | 9/2001 | Rosenthal et al. |
| 6,287,316 B1 | 9/2001 | Agarwal et al. |
| 6,345,623 B1 | 2/2002 | Heaton et al. |
| 6,394,948 B1 | 5/2002 | Borst et al. |
| 6,398,767 B1 | 6/2002 | Fleischmann |
| 6,458,109 B1 | 10/2002 | Henley et al. |
| 6,478,789 B1 | 11/2002 | Spehalski et al. |
| 6,478,960 B1 | 11/2002 | Saruhashi et al. |
| 6,488,643 B1 | 12/2002 | Tumey et al. |
| 6,493,568 B1 | 12/2002 | Bell et al. |
| 6,500,112 B1 | 12/2002 | Khouri |
| 6,551,280 B1 | 4/2003 | Knighton et al. |
| 6,553,998 B2 | 4/2003 | Heaton et al. |
| 6,572,594 B2 | 6/2003 | Satterfield et al. |
| 6,613,026 B1 | 9/2003 | Palasis et al. |
| 6,626,891 B2 | 9/2003 | Ohmstede |
| 6,641,553 B1 | 11/2003 | Chee |
| 6,641,575 B1 | 11/2003 | Lonky |
| 6,648,862 B2 | 11/2003 | Watson |
| 6,656,149 B2 | 12/2003 | Ladd |
| 6,660,484 B2 | 12/2003 | Charych et al. |
| 6,682,506 B1 | 1/2004 | Navarro |
| 6,685,681 B2 | 2/2004 | Lockwood et al. |
| 6,695,823 B1 | 2/2004 | Lina et al. |
| 6,752,794 B2 | 6/2004 | Lockwood et al. |
| 6,755,796 B2 | 6/2004 | Spector |
| 6,755,807 B2 | 6/2004 | Risk, Jr. et al. |
| 6,758,836 B2 | 7/2004 | Zawacki |
| 6,764,497 B2 | 7/2004 | Fogarty et al. |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,840,960 B2 | 1/2005 | Bubb |
| 6,855,135 B2 | 2/2005 | Lockwood et al. |
| 6,866,805 B2 | 3/2005 | Hong et al. |
| 6,871,740 B1 | 3/2005 | Cao |
| 6,979,324 B2 | 12/2005 | Bybordi et al. |
| 7,004,915 B2 | 2/2006 | Boynton et al. |
| 7,022,113 B2 | 4/2006 | Lockwood et al. |
| 7,070,584 B2 | 7/2006 | Johnson et al. |
| 7,077,832 B2 | 7/2006 | Fleischmann |
| 7,128,735 B2 | 10/2006 | Weston |
| 7,195,624 B2 | 3/2007 | Lockwood et al. |
| 7,276,051 B1 | 10/2007 | Henley et al. |
| 7,322,971 B2 | 1/2008 | Shehada |
| 7,344,512 B2 | 3/2008 | Yamazaki et al. |
| 7,396,339 B2 | 7/2008 | Britto et al. |
| 7,699,823 B2 | 4/2010 | Haggstrom et al. |
| 7,753,902 B1 | 7/2010 | Mansour et al. |
| 7,824,384 B2 | 11/2010 | Watson, Jr. |
| 7,976,533 B2 | 7/2011 | Larsson |
| 7,981,098 B2 | 7/2011 | Boehringer et al. |
| 8,057,449 B2 | 11/2011 | Sanders et al. |
| 2002/0028243 A1 | 3/2002 | Masters |
| 2002/0065494 A1 | 5/2002 | Lockwood et al. |
| 2002/0077661 A1 | 6/2002 | Saadat |
| 2002/0111576 A1 | 8/2002 | Greene et al. |
| 2002/0115951 A1 | 8/2002 | Norstrem et al. |
| 2002/0120185 A1 | 8/2002 | Johnson |
| 2002/0143286 A1 | 10/2002 | Tumey |
| 2002/0161346 A1 | 10/2002 | Lockwood et al. |
| 2002/0198503 A1 | 12/2002 | Risk, Jr. et al. |
| 2002/0198504 A1 | 12/2002 | Risk, Jr. et al. |
| 2003/0009187 A1 | 1/2003 | Fogarty et al. |
| 2003/0014022 A1 | 1/2003 | Lockwood et al. |
| 2003/0033017 A1 | 2/2003 | Lotz et al. |
| 2003/0040687 A1 | 2/2003 | Boynton et al. |
| 2003/0057070 A1 | 3/2003 | Wang et al. |
| 2003/0088209 A1 | 5/2003 | Chiu et al. |
| 2003/0167031 A1 | 9/2003 | Odland |
| 2003/0216672 A1 | 11/2003 | Rastegar et al. |
| 2003/0225441 A1 | 12/2003 | Boynton et al. |
| 2004/0006319 A1 | 1/2004 | Lina et al. |
| 2004/0039391 A1 | 2/2004 | Argenta et al. |
| 2004/0039406 A1 | 2/2004 | Jessen |
| 2004/0064111 A1 | 4/2004 | Lockwood et al. |
| 2004/0064132 A1 | 4/2004 | Boehringer et al. |
| 2004/0071949 A1 | 4/2004 | Glatkowski et al. |
| 2004/0093026 A1 | 5/2004 | Weidenhagen et al. |
| 2004/0093080 A1 | 5/2004 | Helmus et al. |
| 2004/0098017 A1 | 5/2004 | Saab et al. |
| 2004/0122434 A1 | 6/2004 | Argenta et al. |
| 2004/0243167 A1 | 12/2004 | Tanaka et al. |
| 2005/0004534 A1 | 1/2005 | Lockwood |
| 2005/0065484 A1 | 3/2005 | Watson, Jr. |
| 2005/0070858 A1 | 3/2005 | Lockwood et al. |
| 2005/0119617 A1 | 6/2005 | Stecker et al. |
| 2005/0131327 A1 | 6/2005 | Lockwood et al. |
| 2005/0137539 A1 | 6/2005 | Biggie et al. |
| 2005/0148913 A1 | 7/2005 | Weston |

(56) References Cited

U.S. PATENT DOCUMENTS

| | | |
|---|---|---|
| 2005/0171467 A1 | 8/2005 | Landman |
| 2005/0192532 A1 | 9/2005 | Kucklick et al. |
| 2005/0203483 A1 | 9/2005 | Perkins et al. |
| 2005/0245906 A1 | 11/2005 | Makower et al. |
| 2005/0261642 A1 | 11/2005 | Weston |
| 2005/0261643 A1 | 11/2005 | Bybordi et al. |
| 2005/0267577 A1 | 12/2005 | Trieu |
| 2006/0024266 A1 | 2/2006 | Brandom et al. |
| 2006/0142685 A1 | 6/2006 | Addison et al. |
| 2006/0149170 A1 | 7/2006 | Boynton et al. |
| 2006/0200003 A1 | 9/2006 | Youssef |
| 2006/0271019 A1 | 11/2006 | Stoller et al. |
| 2007/0118096 A1 | 5/2007 | Smith et al. |
| 2007/0156251 A1 | 7/2007 | Karmon |
| 2007/0237811 A1 | 10/2007 | Scherr |
| 2008/0033333 A1 | 2/2008 | Macphee et al. |
| 2008/0114277 A1 | 5/2008 | Ambrosio et al. |
| 2008/0206308 A1 | 8/2008 | Jabbari et al. |
| 2008/0275409 A1 | 11/2008 | Kane et al. |
| 2008/0319268 A1 | 12/2008 | Michaeli et al. |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | S58-95841 U | 6/1983 |
| JP | 4129536 | 4/1992 |
| JP | 6-70746 U | 10/1994 |
| JP | H11-501837 | 2/1999 |
| JP | 2001-252349 A | 9/2001 |
| JP | 2005-528167 | 9/2005 |
| KR | 10-2002-0000580 A | 1/2002 |
| SG | 71559 | 4/2002 |
| TW | 512066 | 12/2002 |
| TW | 558444 | 10/2003 |
| TW | 200612877 | 5/2006 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | WO 00/07653 | 2/2000 |
| WO | WO 03/057070 | 7/2003 |
| WO | WO 2004/071949 | 8/2004 |
| WO | WO2004071279 | 8/2004 |
| WO | WO 2005/020849 A2 | 3/2005 |
| WO | WO2005/061025 | 7/2005 |
| WO | WO 2005/105180 | 11/2005 |
| WO | WO 2007/133618 | 11/2007 |

OTHER PUBLICATIONS

C. Daniel Medical, Inc.; All Silicone Jackson Pratt(r) Style Round Drain; www.cdanielmedical.com; Mar. 2007, 2 pgs.
C. Daniel Medical, Inc.; All Silicone Jackson Pratt(r) Style Flat Drain; www.cdanielmedical.com; Mar. 2007, 2 pgs.
Kilbride, et al. "Vacuum-assisted closure: a new method for treating patients with gian omphalocele", J Pediatric Surg, Jan. 2006, vol. 41, issue 1, pp. 212-215.
Davydov et al, "Vacuum-therapy of Wounds and Wound Process," Moscow, Meditsina, 1999, pp. 66-69 (English translation).
Restriction Requirement date mailed Jul. 21, 2009 in U.S. Appl. No. 11/717,892.
Response to Restriction Requirement filed Aug. 19, 2009 in U.S. Appl. No. 11/717,892.
Non-Final Office Action date mailed Oct. 28, 2009 in U.S. Appl. No. 11/717,892.
Interview Summary date mailed Dec. 30, 2009 in U.S. Appl. No. 11/717,892.
Response filed Jan. 25, 2010 to Non-Final Action date mailed Oct. 28, 2009 in U.S. Appl. No. 11/717,892.
Non-Final Office Action date mailed May 28, 2008 in U.S. Appl. No. 11/717,854.
Response filed Aug. 13, 2008 in U.S. Appl. No. 11/717,854.
Non-Final Office Action date mailed Nov. 13, 2008 in U.S. Appl. No. 11/717,854.
Response filed Dec. 12, 2008 in U.S. Appl. No. 11/717,854.
Non-Final Office Action date mailed Mar. 5, 2009 in U.S. Appl. No. 11/717,854.
Response filed Jun. 25, 2009 in U.S. Appl. No. 11/717,854.
Non-Final Office Action date mailed Oct. 1, 2009 in U.S. Appl. No. 11/717,854.
Interview Summary date mailed Dec. 11, 2009 in U.S. Appl. No. 11/717,854.
Response filed Dec. 23, 2009 to Non-Final Action dated Oct. 1, 2009 in U.S. Appl. No. 11/717,854.
Non-Final Rejection date mailed Mar. 18, 2010 in U.S. Appl. No. 11/717,854.
Non-Final Office Action date mailed Jun. 18, 2009 in U.S. Appl. No. 11/807,834.
Response filed Aug. 19, 2009 in U.S. Appl. No. 11/807,834.
Final Office Action date mailed Oct. 2, 2009 in U.S. Appl. No. 11/807,834.
RCE/Amendment filed Jan. 27, 2010 in U.S. Appl. No. 11/807,834.
Non-Final Action date mailed Mar. 11, 2010 in U.S. Appl. No. 11/807,834.
Express abandonment filed Apr. 22, 2010 in U.S. Appl. No. 12/540,934.
Decision on Petition for Express Abandonment and Notice of Abandonment date mailed May 3, 2010 in U.S. Appl. No. 12/540,934.
NPD 1000 Negative Pressure Wound Therapy System, Kalypto Medical, pp. 1-4.
Non-Final Office Action dated Sep. 27, 2006 in U.S. Appl. No. 11/200,837.
Response filed Jan. 29, 2007 to Non-Final Office Action dated Sep. 27, 2006 in U.S. Appl. No. 11/200,837.
Final Office Action dated Apr. 27, 2007 in U.S. Appl. No. 11/200,837.
Response filed Jun. 26, 2007 to Final Office Action dated Apr. 27, 2007 in U.S. Appl. No. 11/200,837.
Advisory Action dated Jul. 26, 2007 in U.S. Appl. No. 11/200,837.
Request for Continued Examination/Amendment filed Oct. 29, 2007 in U.S. Appl. No. 11/200,837.
Non-Final Office Action dated Jan. 16, 2008 in U.S. Appl. No. 11/200,837.
Response filed Mar. 27, 2008 to Non-Final Office Action dated Jan. 16, 2008 in U.S. Appl. No. 11/200,837.
Final Office Action dated Jul. 9, 2008 in U.S. Appl. No. 11/200,837.
Response filed Sep. 8, 2008 to Final Office Action dated Jul. 9, 2008 in U.S. Appl. No. 11/200,837.
Final Office Action dated Nov. 14, 2008 in U.S. Appl. No. 11/200,837.
Supplemental Response filed Feb. 27, 2009 to Final Office Action date mailed Nov. 14, 2008 in U.S. Appl. No. 11/200,837.
Restriction Requirement date mailed Mar. 5, 2009 in U.S. Appl. No. 11/200,837.
Response filed Apr. 3, 2009 to Restriction Requirement dated Mar. 5, 2009 in U.S. Appl. No. 11/200,837.
Non-Final Office Action date mailed Jul. 9, 2009 in U.S. Appl. No. 11/200,837.

(56) References Cited

OTHER PUBLICATIONS

Response filed Sep. 17, 2009 to Non-Final Action dated Jul. 9, 2009 in U.S. Appl. No. 11/200,837.
Notice of Allowance and Notice of Allowability date mailed Jan. 14, 2010 in U.S. Appl. No. 11/200,837.
RCE/Amendment filed Apr. 7, 2010 in U.S. Appl. No. 11/200,837.
Non-Final Office Action date mailed May 15, 2012 for U.S. Appl. No. 13/332,233.
Final Office Action date mailed May 16, 2011 for U.S. Appl. No. 11/717,854.
Interview Summary date mailed May 2, 2011 for U.S. Appl. No. 11/724,072.
Response filed May 12, 2011 for U.S. Appl. No. 11/724,072.
Response filed May 16, 2011 for U.S. Appl. No. 11/807,834.
Interview Summary date mailed May 17, 2011 for U.S. Appl. No. 11/807,834.
Non-Final Office Action date mailed May 17, 2011 for U.S. Appl. No. 12/275,417.
Notice of Allowance date mailed Jun. 2, 2011 for U.S. Appl. No. 11/717,892.
Kane et al "Controlled Induction of Distributed Microdeformation in Wounded Tissue via a Microchamber Array Dressing", pp. 333-340; Journal of Biomedical Materials Research; Nov. 2010, vol. 95A, Issue 2.
Non-Final Office Action date mailed Jun. 30, 2011 for U.S. Appl. No. 11/807,834.
Restriction Requirement date mailed Jun. 30, 2011 for U.S. Appl. No. 12/347,791.
Non-Final Office Action date mailed Jul. 27, 2010 for U.S. Appl. No. 11/717,892.
Interview Summary date mailed Jun. 11, 2010 for U.S. Appl. No. 11/807,834.
Response filed Jun. 14, 2010 for U.S. Appl. No. 11/807,834.
Response filed Jul. 1, 2010 for U.S. Appl. No. 11/717,854.
Interview Summary date mailed Jul. 6, 2010 for U.S. Appl. No. 11/717,854.
RCE/Response filed Aug. 10, 2011 for U.S. Appl. No. 11/717,854.
Interview Summary date mailed Aug. 11, 2011 for U.S. Appl. No. 11/717,854.
Non-Final Office Action date mailed Jul. 19, 2011 for U.S. Appl. No. 11/724,073.
Response filed Jul. 26, 201 for U.S. Appl. No. 12/347,791.
Restriction Requirement date mailed Jul. 25, 2011 for U.S. Appl. No. 11/717,893.
Response filed Aug. 12, 2011 for U.S. Appl. No. 11/717,893.
Final Office Action date mailed Aug. 1, 2011 for U.S. Appl. No. 11/724,072.
Notice of Allowance date mailed Jul. 1, 2011 for U.S. Appl. No. 12/069 363.
Response filed Aug. 17, 2011 for U.S. Appl. No. 12/275,417.
Final Office Action date mailed Aug. 31, 2010 for U.S. Appl. No. 11/807,834.
International Search Report and Written Opinion date mailed Sep. 13, 2010 for PCT Application No. PCT/US2009/069495.
Non-Final Office Action date mailed Sep. 15, 2010 for U.S. Appl. No. 11/717,854.
Response filed Oct. 26, 2010 for U.S. Appl. No. 11/717,892.
Restriction Requirement date mailed Oct. 6, 2010 for U.S. Appl. No. 11/724,073.
Response filed Nov. 2, 2010 for U.S. Appl. No. 11/724,073.
Restriction Requirement date mailed Oct. 7, 2010 for U.S. Appl. No. 11/724,072.
Response filed Nov. 8, 2010 for U.S. Appl. No. 11/724,072.
Responsed filed Oct. 26, 2010 for U.S. Appl. No. 11/807,834.
Response filed Sep. 24, 2010 for U.S. Appl. No. 12/069,363.
Interview Summary date mailed Oct. 4, 2010 for U.S. Appl. No. 12/069,363.
Final Office Action date mailed Dec. 7, 2010 for U.S. Appl. No. 12/069,363.

Advisory Action date mailed Nov. 10, 2010 for U.S. Appl. No. 11/807,834.
RCE/Response filed Nov. 24, 2010 for U.S. Appl. No. 11/807,834.
NPD 1000 Negative Pressure Wound Therapy System, Kalypto Medical, pp. 1-4, Sep. 2008.
Non-Final Office Action date mailed Oct. 4, 2011 for U.S. Appl. No. 11/717,893.
Express Abandonment filed Nov. 29, 2011 for U.S. Appl. No. 11/724,072.
Response filed Oct. 19, 2011 for U.S. Appl. No. 11/724,073.
Non-Final Office Action date mailed Oct. 25, 2011 for U.S. Appl. No. 12/275,417.
RCE/Response filed Sep. 8, 2011 for U.S. Appl. No. 11/717,854.
N.A. Bagautdinov, "Variant of External Vacuum Aspiration in the Treatment of Purulent Diseases of the Soft Tissues," *Current Problems in Modem Clinical Surgery: Interdepartmental Collection*, edited by V. Ye Volkov et al. (Chuvashia State University, Cheboksary, U.S.S.R. 1986);pp. 94-96.
Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 pages English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.

(56) References Cited

OTHER PUBLICATIONS

Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Sur., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.
G. Živadinović, V. Ðukić, Ž. Maksimović, Ð.. Radak, and P. Peška, "Vacuum Therapy in the Treatment of Peripheral Blood Vessels," *Timok Medical Journal* 11 (1986), pp. 161-164.
F.E. Johnson, "An Improved Technique for Skin Graft Placement Using a Suction Drain," *Surgery, Gynecology, and Obstetrics* 159 (1984), pp. 584-585.
A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967).
M. Schein, R. Saadia, J.R. Jamieson, and G.A.G. Decker, "The 'Sandwich Technique' in the Management of the Open Abdomen," *British Journal of Surgery* 73 1986, pp. 369-370.
D.E. Tribble, An Improved Sump Drain-Irrigation Device of Simple Construction, *Archives of Surgery* 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).
C.E. Tennants, "The Use of Hypermia in the Postoperative Treatment of Lesions of the Extremities and Thorax," *Journal of the American Medical Association* 64 (1915), pp. 1548-1549.
Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians (Jul. 2007).
Response filed Jan. 28, 2011 for U.S. Appl. No. 12/069,363.
Non-Final Office Action date mailed Feb. 11, 2011 for U.S. Appl. No. 12/069,363.
Response filed Mar. 17, 2011 for U.S. Appl. No. 11/717,892.
Response filed Apr. 18, 2011 for U.S. Appl. No. 11/724,073.
Interview Summary date mailed Apr. 20, 2011 for U.S. Appl. No. 11/724,073.
Response filed Apr. 21, 2011 for U.S. Appl. No. 12/069,363.
Restriction Requirement date mailed Mar. 28, 2011 for U.S. Appl. No 12/275,417.
Response filed Apr. 28, 2011 for U.S. Appl. No. 12/275,417.
Non-Final Office Action date mailed Jan. 12, 2011 for U.S. Appl. No. 11/717,892.
Response filed Dec. 15, 2010 for U.S. Appl. No. 11/717,854.
Interview Summary date mailed Dec. 19, 2010 for U.S. Appl. No. 11/717,854.
Non-Final Office Action date mailed Jan. 21, 2011 for U.S. Appl. No. 11/724,073.
Non-Final Office Action date mailed Feb. 14, 2011 for U.S. Appl. No. 11/724,072.
Non-Final Office Action date mailed Feb. 18, 2011 for U.S. Appl. No. 11/807,834.
International Search Report and Written Opinion date mailed Jun. 28, 2010 for PCT Application No. PCT/US2009/064972.
Restriction Requirement date mailed Apr. 13, 2010 for U.S. Appl. No. 12/069,363.
Response filed May 4, 2010 for U.S. Appl. No. 12/069,363.
Non-Final Office Action date mailed Jul. 9, 2010 for U.S. Appl. No. 12/069,363.
Notice of Allowance date mailed Jun. 16, 2010 for U.S. Appl. No. 11/200,837.
Borzacchiello et al. "Chitosan based hydrogels: Synthesis and characterization" Journal of Materials Science: Materials in Medicine, 12, 2011, pp. 861-864.
Lee et al. "Hydrogels for Tissue Engineering" Chemical Reviews, 101(7), 2001, pp. 1869-1879.
Ma et al. "A preliminary in vitro study on the fabrication and tissue engineering applications of a novel chitosan bilayer material as a scaffold of human neofetal dermal fibroblasts" Biomaterials, 22, 2001, pp. 311-336.
Non-Final Office Action date mailed Dec. 19, 2011 for U.S. Appl. No. 12/347,791.
Extended European Search Report issued Jan. 11, 2013 in corresponding European Application No. 07753287.7-2370.

\* cited by examiner

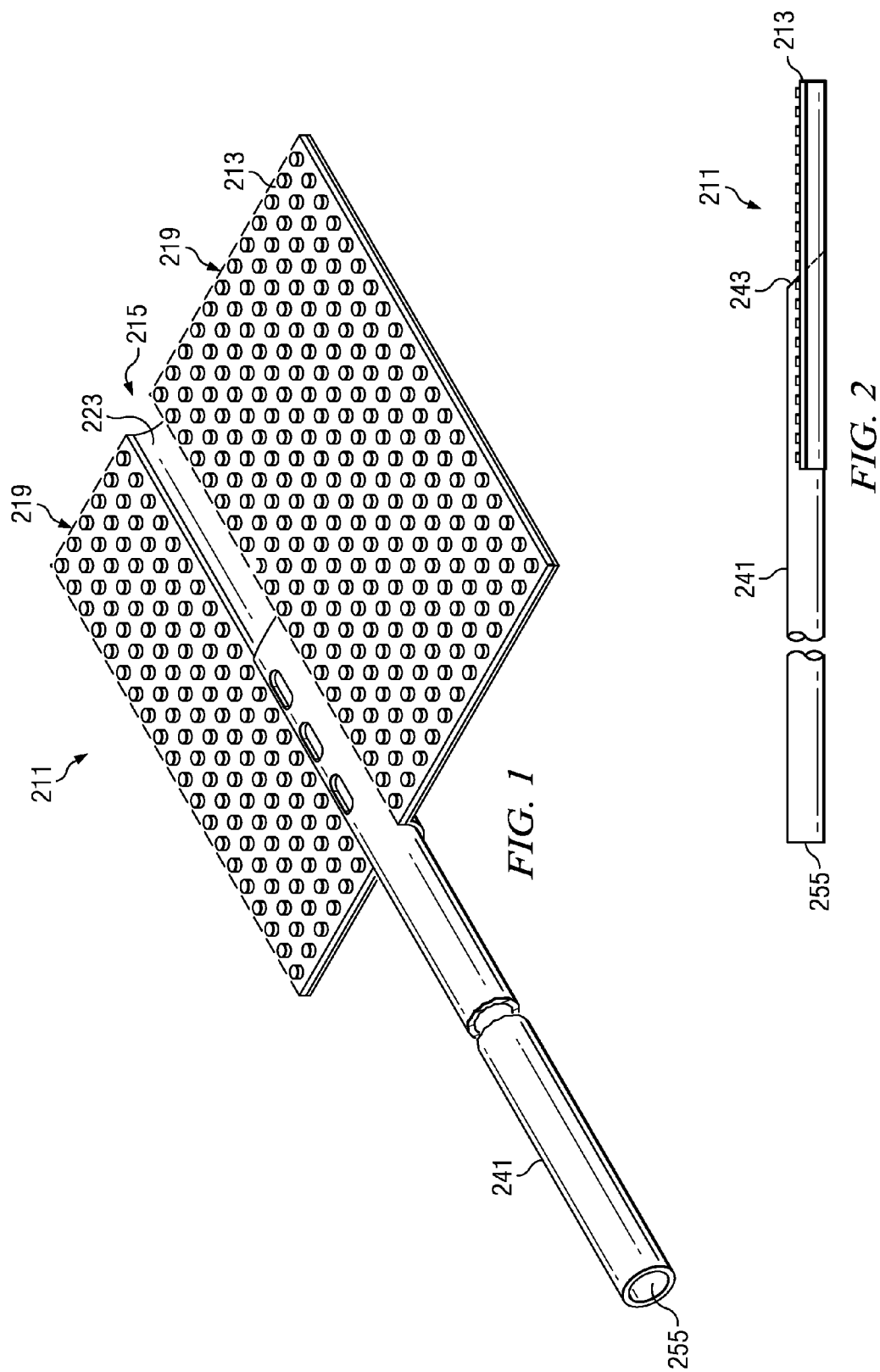

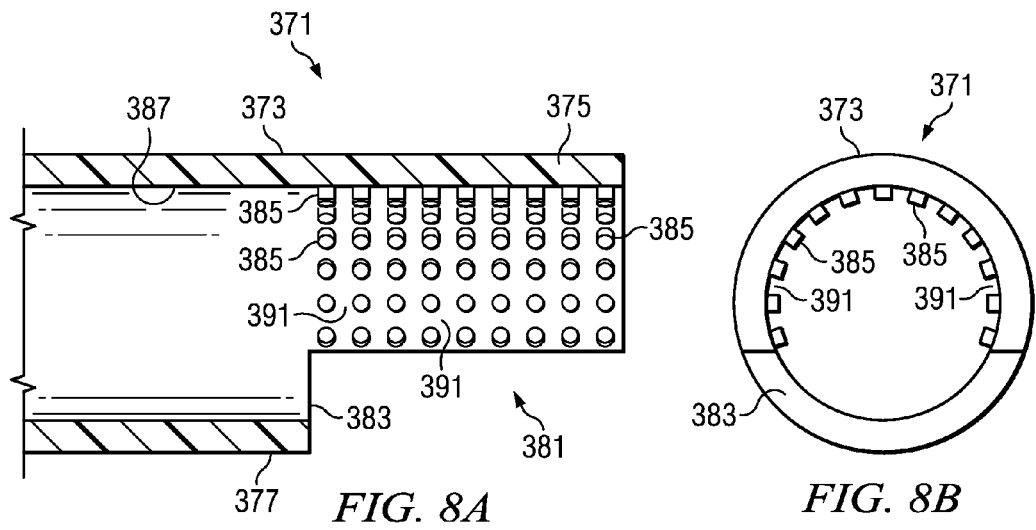
FIG. 8A
FIG. 8B
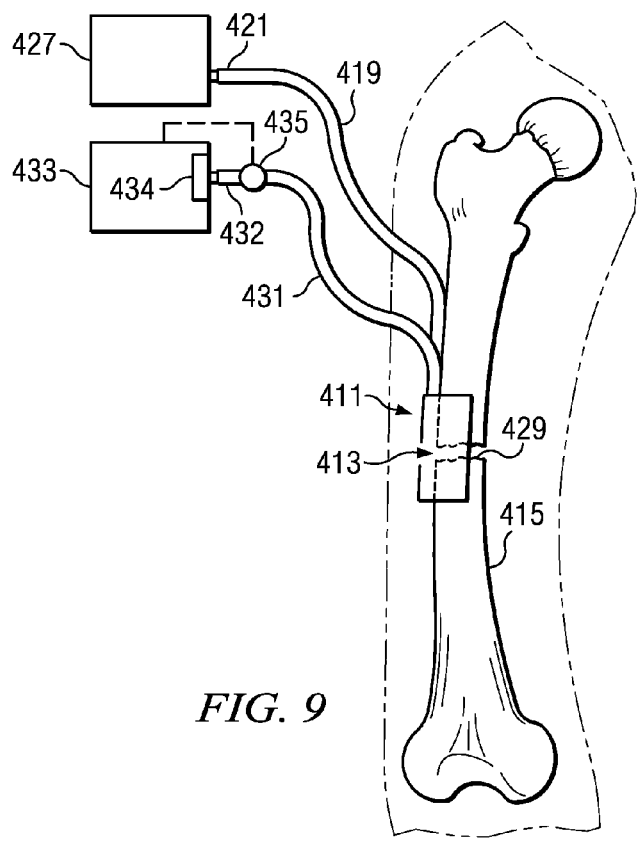
FIG. 9

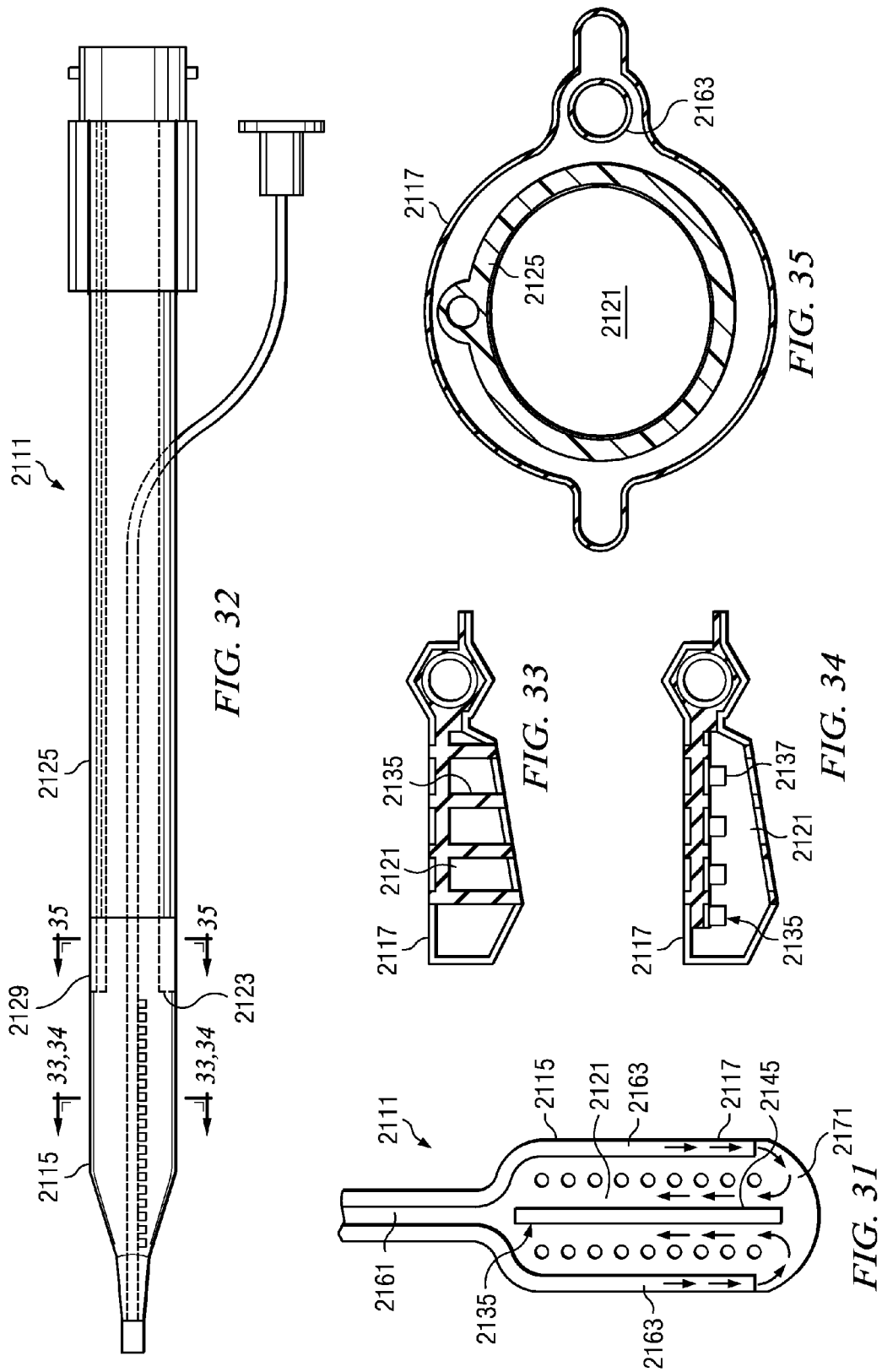

MANIFOLDS, SYSTEMS, AND METHODS FOR ADMINISTERING REDUCED PRESSURE TO A SUBCUTANEOUS TISSUE SITE

CROSS-REFERENCE TO RELATED APPLICATIONS

This application is a continuation-in-part of U.S. patent application Ser. No. 12/540,934, filed Aug. 13, 2009, now abandoned which is a continuation-in-part of U.S. patent application Ser. No. 11/807,834, filed May 29, 2007, now abandoned which is a continuation-in-part of U.S. patent application Ser. No. 11/724,072, filed on Mar. 13, 2007, now abandoned which claims the benefit of U.S. Provisional Application Ser. No. 60/782,171, filed Mar. 14, 2006. The present application also claims the benefit, under 35 USC §119(e), of the filing of U.S. Provisional Patent Application Ser. No. 61/141,728, filed Dec. 31, 2008. All of the above-referenced applications are hereby incorporated by reference for all purposes.

BACKGROUND OF THE INVENTION

The illustrative embodiments relate generally to systems, apparatuses, and methods of promoting tissue growth and more specifically a system for applying reduced-pressure tissue treatment to a tissue site, such as a bone.

Reduced-pressure therapy is increasingly used to promote wound healing in soft tissue wounds that are slow to heal or non-healing without reduced-pressure therapy. Typically, reduced pressure is applied to the wound site through an open-cell foam or other device that serves as a manifold to distribute the reduced pressure. The open-cell foam is sized to fit the existing wound, placed into contact with the wound, and then periodically replaced with smaller pieces of foam as the wound begins to heal and become smaller. Frequent replacement of the open-cell foam may be necessary to minimize the amount of tissue that grows into the cells of the foam. Significant tissue in-growth can cause pain to patients during removal of the foam.

Reduced-pressure therapy may be applied to non-healing, open wounds. In some cases, the tissues being healed are subcutaneous, and in other cases, the tissues are located within or on dermal tissue. Traditionally, reduced-pressure therapy has primarily been applied to soft tissues. Reduced-pressure therapy has not typically been used to treat closed, deep-tissue wounds because of the difficulty of access presented by such wounds. Additionally, reduced-pressure therapy has not generally been used in connection with healing bone defects or promoting bone growth, primarily due to access problems.

BRIEF SUMMARY

To alleviate the existing problems with reduced-pressure treatment systems, the illustrative embodiments described herein are directed to a systems, methods, and apparatuses for applying a reduced pressure to a subcutaneous tissue site. An apparatus includes a manifold that is adapted to be inserted for placement at the subcutaneous tissue site. The manifold may include at least one purging lumen operable to deliver a fluid to a distal portion of the manifold. The manifold may also include at least one slit at the distal portion of the manifold. The manifold may include at least one reduced-pressure lumen operable to deliver reduced pressure to the subcutaneous tissue site via the at least one slit. In one example, the manifold also includes an interlumen channel fluidly interconnecting the at least one purging lumen, the at least one reduced-pressure lumen, and the at least one slit at the distal portion of the manifold.

According to one illustrative embodiment, a system for applying a reduced pressure at a subcutaneous tissue site is also provided. The system includes a reduced-pressure source operable to supply reduced pressure to a manifold. The manifold may include at least one reduced-pressure lumen operable to deliver reduced pressure supplied from the reduced-pressure source to the subcutaneous tissue site via at least one slit. The system may also include a delivery tube in fluid communication with the manifold and the reduced pressure source to deliver reduced pressure to the at least one reduced-pressure lumen. The delivery tube may also provide for the delivery of fluid to the at least one purge lumen.

According to one illustrative embodiment, a method for applying a reduced pressure at a subcutaneous tissue site is also provided. The method may include applying a manifold to the subcutaneous tissue site. The method may also include supplying a reduced pressure to the manifold via a delivery tube.

According to one illustrative embodiment, a method of manufacturing an apparatus for applying a reduced pressure at a subcutaneous tissue site on a patient is also provided. The method may include forming a manifold adapted to be inserted into the patient and for placement at the subcutaneous tissue site. In one example, the method may also include providing a delivery tube for delivering reduced pressure to at least one reduced-pressure lumen in the manifold and fluid to at least one purge lumen in the manifold. In this example, the method may also include coupling the delivery tube to the manifold such that the delivery tube is in fluid communication with the manifold.

According to another illustrative embodiment, a manifold for providing reduced pressure to a subcutaneous tissue site on a patient includes a longitudinal manifold body formed with at least one purging lumen and a reduced-pressure lumen. The manifold body has a first side and a second, tissue-facing side. The manifold further includes a plurality of manifolding surface features formed on the second, tissue-facing side of the longitudinal manifold body and a plurality of apertures formed in the longitudinal manifold body on the second, tissue-facing side. The plurality of apertures fluidly couple the reduced-pressure lumen and the manifolding surface features. The manifold further includes an end cap fluidly coupling the reduced-pressure lumen and the at least one purging lumen.

According to another illustrative embodiment, a system for treating a subcutaneous tissue site on a patient with reduced pressure includes a reduced-pressure source, a manifold, and a reduced pressure delivery tube coupling the reduced-pressure source and the manifold. The manifold includes a longitudinal manifold body formed with at least one purging lumen and a reduced-pressure lumen. The manifold body has a first side and a second, tissue-facing side. The manifold further includes a plurality of manifolding surface features formed on the second, tissue-facing side of the longitudinal manifold body and a plurality of apertures formed in the longitudinal manifold body on the second, tissue-facing side. The plurality of apertures fluidly couple the reduced-pressure lumen and the manifolding surface features. The manifold further includes an end cap fluidly coupling the reduced-pressure lumen and the at least one purging lumen.

According to another illustrative embodiment, a method of manufacturing a manifold for providing reduced pressure to a subcutaneous tissue site on a patient includes forming a longitudinal manifold body with at least one purging lumen and a reduced-pressure lumen. The manifold body has a first side and a second, tissue-facing side. The method further includes forming a plurality of manifolding surface features on the second, tissue-facing side of the longitudinal manifold body and forming a plurality of apertures in the longitudinal manifold body on the second, tissue-facing side. The plurality of apertures fluidly couple the reduced-pressure lumen and the manifolding surface features. The method further includes forming an end cap on the manifold body that fluidly couples the reduced-pressure lumen and the at least one purging lumen.

According to an illustrative, non-limiting embodiment, a system for applying reduced pressure to a subcutaneous tissue site that includes a reduced-pressure source for supplying reduced pressure, a fluid source for supplying a fluid, and a manifold adapted for placement at the subcutaneous tissue site. The manifold includes a plurality of first conduits, each of the plurality of first conduits having a wall formed with at least one first aperture and at least one second aperture. At least one of the plurality of first conduits is in fluid communication with the reduced-pressure source and is operable to deliver the reduced pressure to the subcutaneous tissue site via the at least one first aperture. The manifold further includes a second conduit formed by a portion of each wall of the plurality of first conduits. The second conduit is in fluid communication with the plurality of first conduits via the at least one second aperture. The system may further include a delivery conduit fluidly coupled to the manifold and reduced-pressure source.

According to another illustrative, non-limiting embodiment, a manifold for applying reduced pressure to a subcutaneous tissue site includes a plurality of first conduits, each of the plurality of first conduits having a wall with at least one first aperture and at least one second aperture. At least one of the plurality of first conduits is operable to deliver reduced pressure to the subcutaneous tissue site via the at least one first aperture. The plurality of first conduits is coupled in a spaced arrangement that forms an interior space. The manifold further includes a second conduit comprising the interior space and formed by a portion of each wall of the plurality of first conduits. The second conduit is in fluid communication with the plurality of first conduits via the at least one second aperture.

According to another illustrative, non-limiting embodiment, a method for applying reduced pressure to a subcutaneous tissue site includes providing a manifold, applying the manifold to the subcutaneous tissue site, and supplying the reduced pressure to the manifold via a delivery conduit. The manifold includes a plurality of first conduits. Each of the plurality of first conduits has a wall with at least one first aperture and at least one second aperture. At least one of the plurality of first conduits is operable to deliver reduced pressure to the subcutaneous tissue site via the at least one first aperture. The plurality of first conduits are coupled in a spaced arrangement that forms an interior space. The manifold further includes a second conduit comprising the interior space and formed by a portion of each wall of the plurality of first conduits. The second conduit is in fluid communication with the plurality of first conduits via the at least one second aperture.

According to another illustrative, non-limiting embodiment, a method of manufacturing an apparatus that is applying reduced pressure to a subcutaneous tissue includes providing a plurality of first conduits. Each of the plurality of first conduits has a wall formed with at least one first aperture and at least one second aperture. At least one of the plurality of first conduits is operable to deliver reduced pressure to the subcutaneous tissue site via the at least one first aperture. The method further includes coupling the plurality of first conduits to one another to form a second conduit. The second conduit is formed by a portion of each wall of the plurality of first conduits and is in fluid communication with the plurality of first conduits via the at least one second aperture.

According to another illustrative, non-limiting embodiment, a medical manifold for delivering one or more fluids to a tissue site includes a plurality of exterior conduits coupled in a spaced relationships to define an interior space between the plurality of exterior conduits. The interior space comprises a central conduit. The medical manifold further includes a plurality of apertures formed on the plurality of external conduits.

According to another illustrative, non-limiting embodiment, a method of manufacturing a medical manifold includes forming four first conduits with each first conduit touching two other first conduits, forming a second conduit from the four first conduits, and using a core pin to create apertures in the first conduits and the second conduit.

Other features and advantages of the illustrative embodiments will become apparent with reference to the drawings and detailed description that follow.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 depicts a perspective view of a reduced-pressure delivery apparatus according to an embodiment of the present invention, the reduced-pressure delivery apparatus having a plurality of projections extending from a flexible barrier to create a plurality of flow channels;

FIG. 2 illustrates a front view of the reduced-pressure delivery apparatus of FIG. 1;

FIG. 8A illustrates a cross-sectional front view of a reduced-pressure delivery apparatus according to an embodiment of the present invention;

FIG. 8B depicts a side view of the reduced-pressure delivery apparatus of FIG. 8A;

FIG. 9 illustrates a front view of a reduced-pressure delivery apparatus according to an embodiment of the present invention being used to apply a reduced-pressure tissue treatment to a bone of a patient;

FIGS. 30-38 depict various views of a reduced-pressure delivery system according to an embodiment of the present invention, the reduced-pressure delivery system having a primary manifold that includes a flexible wall surrounding a primary flow passage and a plurality of apertures in the flexible wall;

DETAILED DESCRIPTION

Figure 3:
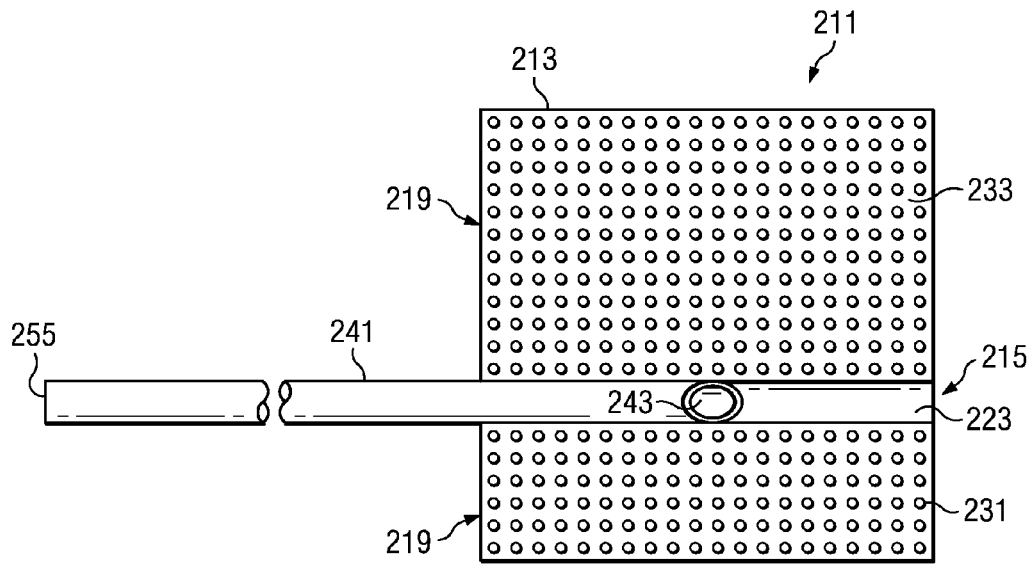
FIG. 3 depicts a top view of the reduced-pressure delivery apparatus of FIG. 1.

In the following detailed description of the preferred embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

As used herein, the term "elastomeric" means having the properties of an elastomer. The term "elastomer" refers generally to a polymeric material that has rubber-like properties. More specifically, most elastomers have an ultimate elongation greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, and silicones.

As used herein, the term "flexible" refers to an object or material that is able to be bent or flexed. Elastomeric materials are typically flexible, but reference to flexible materials herein does not necessarily limit material selection to only elastomers. The use of the term "flexible" in connection with a material or reduced-pressure delivery apparatus of the present invention generally refers to the material's ability to conform to or closely match the shape of a tissue site. For example, the flexible nature of a reduced-pressure delivery apparatus used to treat a bone defect may allow the apparatus to be wrapped or folded around the portion of the bone having the defect.

The term "fluid" as used herein generally refers to a gas or liquid, but may also include any other flowable material, including but not limited to gels, colloids, and foams.

The term "impermeable" as used herein generally refers to the ability of a membrane, cover, sheet, or other substance to block or slow the transmission of either liquids or gas. Impermeability may be used to refer to covers, sheets, or other membranes that are resistant to the transmission of liquids, while allowing gases to transmit through the membrane. While an impermeable membrane may be liquid tight, the membrane may simply reduce the transmission rate of all or only certain liquids. The use of the term "impermeable" is not meant to imply that an impermeable membrane is above or below any particular industry standard measurement for impermeability, such as a particular value of water vapor transfer rate (WVTR).

The term "manifold" as used herein generally refers to a substance or structure that is provided to assist in applying reduced pressure to, delivering fluids to, or removing fluids from a tissue site. A manifold typically includes a plurality of flow channels or pathways that are interconnected to improve distribution of fluids provided to and removed from the area of tissue around the manifold. Examples of manifolds may include without limitation devices that have structural elements arranged to form flow channels, cellular foam, such as open-cell foam, porous tissue collections, and liquids, gels, and foams that include or cure to include flow channels.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure of tissue at the tissue site. Reduced pressure may initially generate fluid flow in the tube and the area of the tissue site. As the hydrostatic pressure around the tissue site approaches the desired reduced pressure, the flow may subside, and the reduced pressure is then maintained. Unless otherwise indicated, values of pressure stated herein are gauge pressures.

The term "scaffold" as used herein refers to a substance or structure used to enhance or promote the growth of cells or the formation of tissue. Unless otherwise indicated, "or" does not require mutual exclusivity. A scaffold is typically a three-dimensional porous structure that provides a template for cell growth. The scaffold may be infused with, coated with, or comprised of cells, growth factors, or other nutrients to promote cell growth. A scaffold may be used as a manifold in accordance with the embodiments described herein to administer reduced-pressure tissue treatment to a tissue site.

The term "tissue site" as used herein refers to a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced-pressure tissue treatment may be used in certain tissue areas to grow additional tissue that may be harvested and transplanted to another tissue location.

Referring primarily to FIGS. 1-5, a reduced-pressure delivery apparatus, or wing manifold 211 according to the principles of the present disclosure includes a flexible barrier 213 having a spine portion 215 and a pair of wing portions 219. Each wing portion 219 is positioned along opposite sides of the spine portion 215. The spine portion 215 forms an arcuate channel 223 that may or may not extend the entire length of the wing manifold 211. Although the spine portion 215 may be centrally located on the wing manifold 211 such that the width of the wing portions 219 is equal, the spine portion 215 may also be offset as illustrated in FIGS. 1-5, resulting in one of the wing portions 219 being wider than the other wing portion 219. The extra width of one of the wing portions 219 may be particularly useful if the wing manifold 211 is being used in connection with bone regeneration or healing and the wider wing manifold 211 is to be wrapped around fixation hardware attached to the bone.

The flexible barrier 213 is preferably formed by an elastomeric material such as a silicone polymer. An example of a suitable silicone polymer includes MED-6015 manufactured by Nusil Technologies of Carpinteria, Calif. It should be noted, however, that the flexible barrier 213 could be made from any other biocompatible, flexible material. The flexible barrier 213 encases a flexible backing 227 that adds strength and durability to the flexible barrier 213. The thickness of the flexible barrier 213 encasing the flexible backing 227 may be less in the arcuate channel 223 than that in the wing portions 219. If a silicone polymer is used to form the flexible barrier 213, a silicone adhesive may also be used to aid bonding with the flexible backing 227. An example of a silicone adhesive could include MED-1011, also sold by Nusil Technologies. The flexible backing 227 is preferably made from a polyester knit fabric, such as Bard 6013 manufactured by C.R. Bard of Tempe, Ariz. However, the flexible backing 227 could be made from any biocompatible, flexible material that is capable of adding strength and durability to the flexible barrier 213. Under certain circumstances, if the flexible barrier 213 is made from a suitably strong material, the flexible backing 227 could be omitted.

It is preferred that either the flexible barrier 213 or the flexible backing 227 be impermeable to liquids, air, and other gases, or alternatively, both the flexible backing 227 and the flexible barrier 213 may be impermeable to liquids, air, and other gases.

The flexible barrier 213 and flexible backing 227 may also be constructed from bioresorbable materials that do not have to be removed from a patient's body following use of the wing manifold 211. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The flexible barrier 213 and the flexible backing 227 may further serve as a scaffold for new cell-growth, or a scaffold material may be used in conjunction with the flexible barrier 213 and flexible backing 227 to promote cell-growth. Suitable scaffold material may include, without limitation, calcium phosphate, collagen, PLA/PGA, coral hydroxy apatites, carbonates, or processed allograft materials. Preferably, the scaffold material will have a high void-fraction (i.e., a high content of air).

In one embodiment the flexible backing 227 may be adhesively attached to a surface of the flexible barrier 213. If a silicone polymer is used to form the flexible barrier 213, a silicone adhesive may also be used to attach the flexible backing 227 to the flexible barrier 213. While an adhesive is the preferred method of attachment when the flexible backing 227 is surface bonded to the flexible barrier 213, any suitable attachment may be used.

The flexible barrier 213 includes a plurality of projections 231 extending from the wing portions 219 on a surface of the flexible barrier 213. The projections 231 may be cylindrical, spherical, hemispherical, cubed, or any other shape, as long as at least some portion of each projection 231 is in a plane different than the plane associated with the side of the flexible barrier 213 to which the projections 231 are attached. In this regard, a particular projection 231 is not even required to have the same shape or size as other projections 231; in fact, the projections 231 may include a random mix of different shapes and sizes. Consequently, the distance by which each projection 231 extends from the flexible barrier 213 could vary, but may also be uniform among the plurality of projections 231.

The placement of projections 231 on the flexible barrier 213 creates a plurality of flow channels 233 between the projections. When the projections 231 are of uniform shape and size and are spaced uniformly on the flexible barrier 213, the flow channels 233 created between the projections 231 are similarly uniform. Variations in the size, shape, and spacing of the projections 231 may be used to alter the size and flow characteristics of the flow channels 233.

Figure 5:
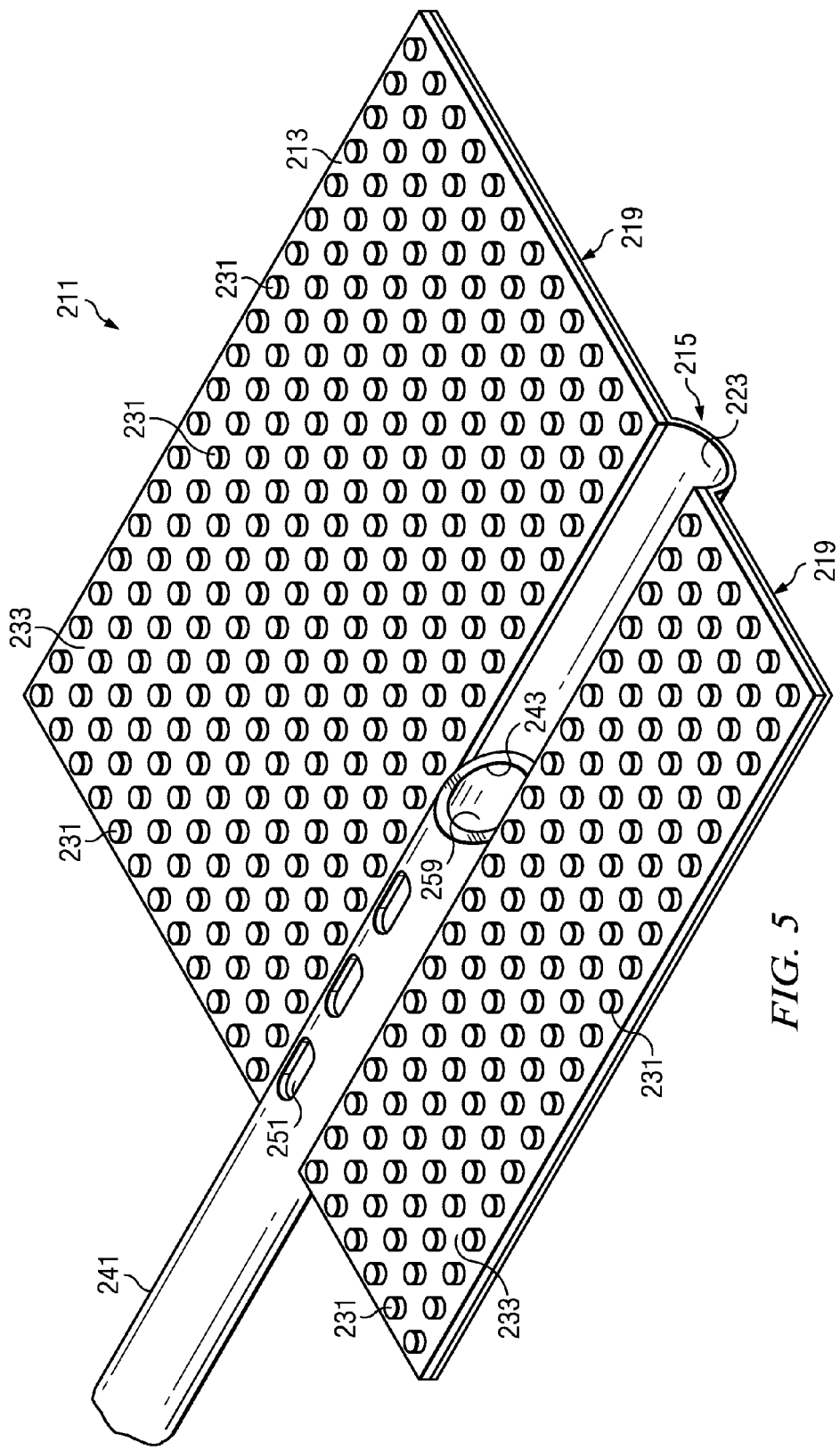
FIG. 5 illustrates an enlarged perspective view of the reduced-pressure delivery apparatus of FIG. 1.

A reduced-pressure delivery tube 241 is positioned within the arcuate channel 223 and is attached to the flexible barrier 213 as illustrated in FIG. 5. The reduced-pressure delivery tube 241 may be attached solely to the flexible barrier 213 or the flexible backing 227, or the reduced-pressure delivery tube 241 could be attached to both the flexible barrier 213 and the flexible backing 227. The reduced-pressure delivery tube 241 includes a distal orifice 243 at a distal end of the reduced-pressure delivery tube 241. The reduced-pressure delivery tube 241 may be positioned such that the distal orifice 243 is located at any point along the arcuate channel 223, but the reduced-pressure delivery tube 241 is preferably positioned such that the distal orifice 243 is located approximately midway along the longitudinal length of the arcuate channel 223. The distal orifice 243 is preferably made elliptical or oval in shape by cutting the reduced-pressure delivery tube 241 along a plane that is oriented less than ninety (90) degrees to the longitudinal axis of the tube 241. While the distal orifice 243 may also be round, the elliptical shape of the distal orifice 243 increases fluid communication with the flow channels 233 formed between the projections 231.

The reduced-pressure delivery tube 241 is preferably made from paralyne-coated silicone or urethane. However, any medical-grade tubing material may be used to construct the reduced-pressure delivery tube 241. Other coatings that may coat the tube include heparin, anti-coagulants, anti-fibrinogens, anti-adherents, anti-thrombinogens, and hydrophilic coatings.

In one embodiment, the reduced-pressure delivery tube 241 may also include vent openings, or vent orifices 251 positioned along the reduced-pressure delivery tube 241 as either an alternative to the distal orifice 243 or in addition to the distal orifice 243 to further increase fluid communication between the reduced-pressure delivery tube 241 and the flow channels 233. The reduced-pressure delivery tube 241 may be positioned along only a portion of the longitudinal length of the arcuate channel 223 as shown in FIGS. 1-5, or alternatively may be positioned along the entire longitudinal length of the arcuate channel 223. If positioned such that the reduced-pressure delivery tube 241 occupies the entire length of the arcuate channel 223, the distal orifice 243 may be capped such that all fluid communication between the tube 241 and the flow channels 233 occurs through the vent orifices 251.

The reduced-pressure delivery tube 241 further includes a proximal orifice 255 at a proximal end of the tube 241. The proximal orifice 255 is configured to mate with a reduced-pressure source, which is described in more detail below with reference to FIG. 9. The reduced-pressure delivery tube 241 illustrated in FIGS. 1-3, 4A, and 5 includes only a single lumen, or passageway 259. It is possible, however, for the reduced-pressure delivery tube 241 to include multiple lumens, such as a dual lumen tube 261 illustrated in FIG. 4B. The dual lumen tube 261 includes a first lumen 263 and a second lumen 265. The use of a dual lumen tube provides separate paths of fluid communication between the proximal end of the reduced-pressure delivery tube 241 and the flow channels 233. For example, the use of the dual lumen tube 261 may be used to allow communication between the reduced-pressure source and the flow channels 233 along the first lumen 263. The second lumen 265 may be used to introduce a fluid to the flow channels 233. The fluid may be filtered air or other gases, antibacterial agents, antiviral agents, cell-growth promotion agents, irrigation fluids, chemically active fluids, or any other fluid. If it is desired to introduce multiple fluids to the flow channels 233 through separate fluid communication paths, a reduced-pressure delivery tube may be provided with more than two lumens.

Figure 4A:
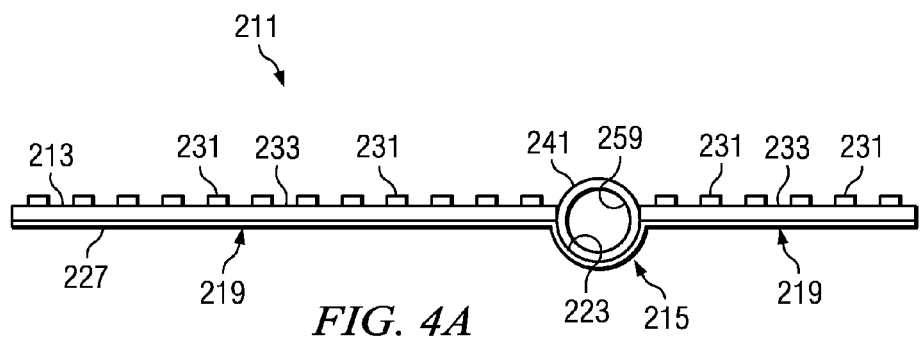
FIG. 4A illustrates a side view of the reduced-pressure delivery apparatus of FIG. 1, the reduced-pressure delivery apparatus having a single lumen, reduced-pressure delivery tube.
Figure 4B:
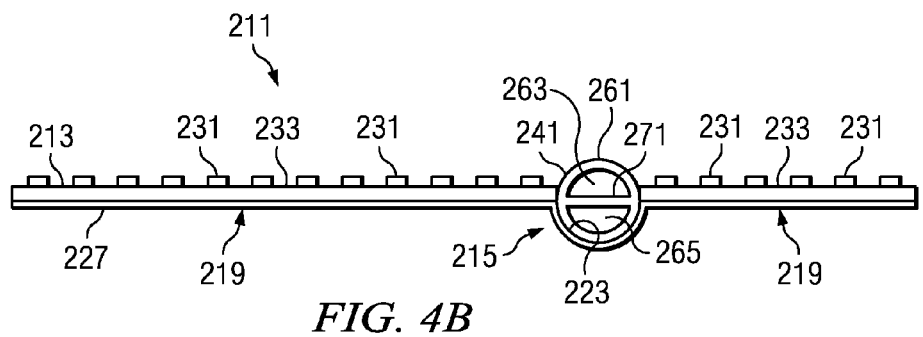
FIG. 4B depicts a side view of an alternative embodiment of the reduced-pressure delivery apparatus of FIG. 1, the reduced-pressure delivery apparatus having a dual lumen, reduced-pressure delivery tube.

Referring still to FIG. 4B, a horizontal divider 271 separates the first and second lumens 263, 265 of the reduced-pressure delivery tube 241, resulting in the first lumen 263 being positioned above the second lumen 265. The relative position of the first and second lumens 263, 265 may vary, depending on how fluid communication is provided between the first and second lumens 263, 265 and the flow channels 233. For example, when the first lumen 263 is positioned as illustrated in FIG. 4B, vent openings similar to vent openings 251 may be provided to allow communication with the flow channels 233. When the second lumen 265 is positioned as illustrated in FIG. 4B, the second lumen 265 may communicate with the flow channels 233 through a distal orifice similar to distal orifice 243. Alternatively, the multiple lumens of a reduced-pressure delivery tube could be positioned side by side with a vertical divider separating the lumens, or the lumens could be arranged concentrically or coaxially.

It should be apparent to a person having ordinary skill in the art that the provision of independent paths of fluid communication could be accomplished in a number of different ways, including that of providing a multi-lumen tube as described above. Alternatively, independent paths of fluid communication may be provided by attaching a single lumen tube to another single lumen tube, or by using separate, unattached tubes with single or multiple lumens.

If separate tubes are used to provide separate paths of fluid communication to the flow channels 233, the spine portion 215 may include multiple arcuate channels 223, one for each tube. Alternatively the arcuate channel 223 may be enlarged to accommodate multiple tubes. An example of a reduced-pressure delivery apparatus having a reduced-pressure delivery tube separate from a fluid delivery tube is discussed in more detail below with reference to FIG. 9.

Figure 6:
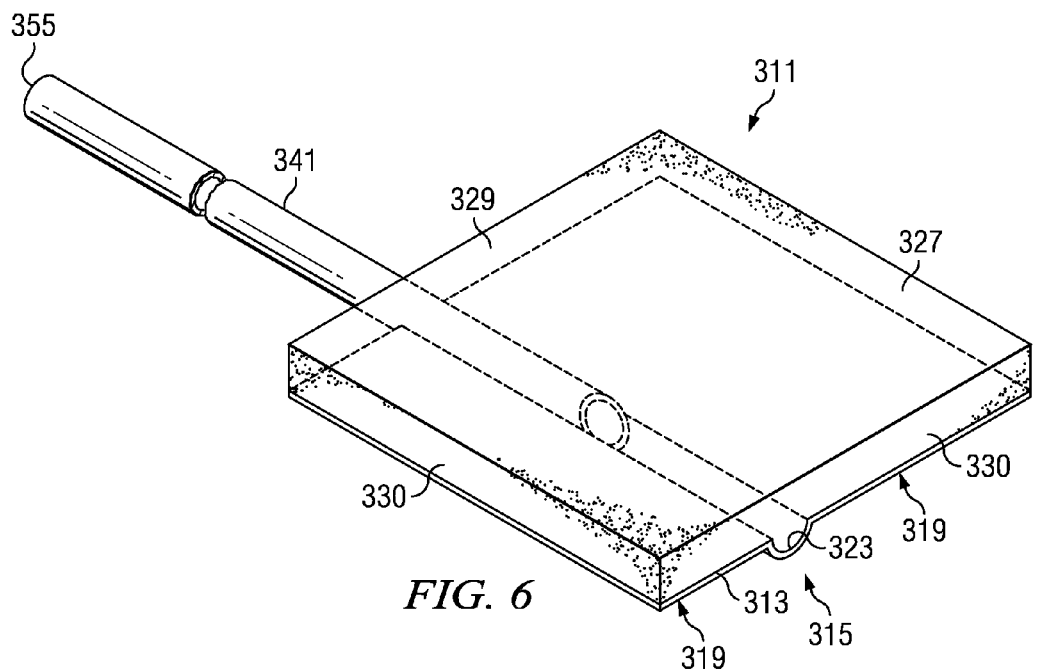
FIG. 6 depicts a perspective view of a reduced-pressure delivery apparatus according to an embodiment of the present invention, the reduced-pressure delivery apparatus having a cellular material attached to a flexible barrier having a spine portion and a pair of wing portions, the cellular material having a plurality of flow channels.
Figure 7:
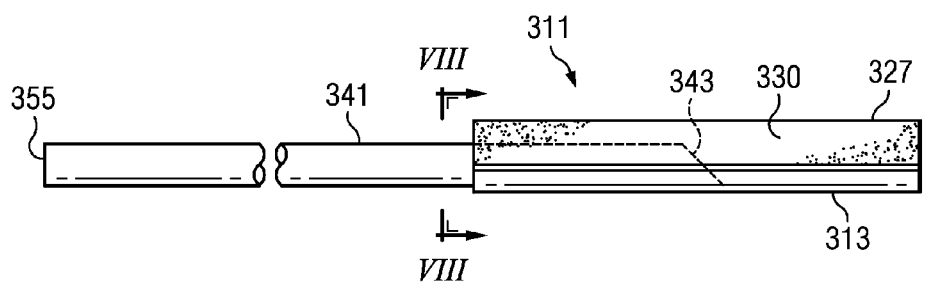
FIG. 7 illustrates a front view of the reduced-pressure delivery apparatus of FIG. 6.
Figure 8:
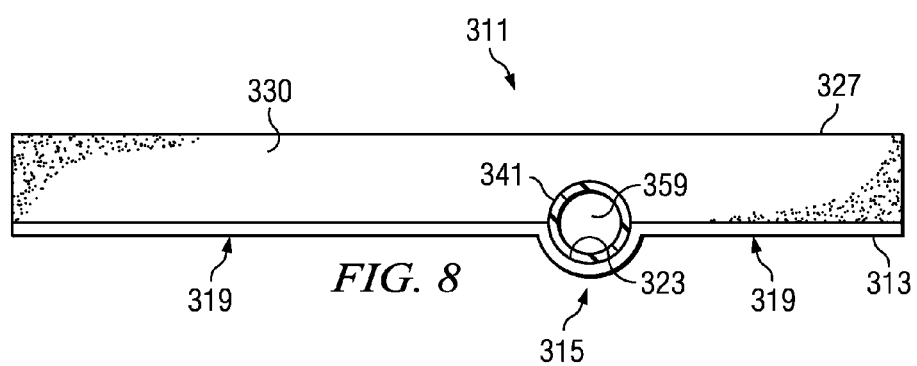
FIG. 8 depicts a cross-sectional side view of the reduced-pressure delivery apparatus of FIG. 7 taken at VIII-VIII.

Referring primarily to FIGS. 6-8, a reduced-pressure delivery apparatus, or wing manifold 311 according to the principles of the present disclosure includes a flexible barrier 313 having a spine portion 315 and a pair of wing portions 319. Each wing portion 319 is positioned along opposite sides of the spine portion 315. The spine portion 315 forms an arcuate channel 323 that may or may not extend the entire length of the wing manifold 311. Although the spine portion 315 may be centrally located on the wing manifold 311 such that the size of the wing portions 319 is equal, the spine portion 315 may also be offset as illustrated in FIGS. 6-8, resulting in one of the wing portions 319 being wider than the other wing portion 319. The extra width of one of the wing portions 319 may be particularly useful if the wing manifold 311 is being used in connection with bone regeneration or healing and the wider wing manifold 311 is to be wrapped around fixation hardware attached to the bone.

A cellular material 327 is attached to the flexible barrier 313 and may be provided as a single piece of material that covers the entire surface of the flexible barrier 313, extending across the spine portion 315 and both wing portions 319. The cellular material 327 includes an attachment surface (not visible in FIG. 6) that is disposed adjacent to the flexible barrier 313, a main distribution surface 329 opposite the attachment surface, and a plurality of perimeter surfaces 330.

In one embodiment the flexible barrier 313 may be similar to flexible barrier 213 and include a flexible backing. While an adhesive is a preferred method of attaching the cellular material 327 to the flexible barrier 313, the flexible barrier 313 and cellular material 327 could be attached by any other suitable attachment method or left for the user to assemble at the site of treatment. The flexible barrier 313 or flexible backing serve as an impermeable barrier to transmission of fluids, such as liquids, air, and other gases.

In one embodiment, a flexible barrier and flexible backing may not be separately provided to back the cellular material 327. Rather, the cellular material 327 may have an integral barrier layer that is an impermeable portion of the cellular material 327. The barrier layer could be formed from closed-cell material to prevent transmission of fluids, thereby substituting for the flexible barrier 313. If an integral barrier layer is used with the cellular material 327, the barrier layer may include a spine portion and wing portions as described previously with reference to the flexible barrier 313.

The flexible barrier 313 is preferably made from an elastomeric material, such as a silicone polymer. An example of a suitable silicone polymer includes MED-6015 manufactured by Nusil Technologies of Carpinteria, Calif. It should be noted, however, that the flexible barrier 313 could be made from any other biocompatible, flexible material. If the flexible barrier encases or otherwise incorporates a flexible backing, the flexible backing is preferably made from a polyester knit fabric such as Bard 6013 manufactured by C.R. Bard of Tempe, Ariz. However, the flexible backing could be made from any biocompatible, flexible material that is capable of adding strength and durability to the flexible barrier 313.

In one embodiment, the cellular material 327 is an open-cell, reticulated polyetherurethane foam with pore sizes ranging from about 400-600 microns. An example of this foam may include GranuFoam® material manufactured by Kinetic Concepts, Inc. of San Antonio, Tex. The cellular material 327 may also be gauze, felted mats, or any other biocompatible material that provides fluid communication through a plurality of channels in three dimensions.

The cellular material 327 is primarily an "open cell" material that includes a plurality of cells fluidly connected to adjacent cells. A plurality of flow channels is formed by and between the "open cells" of the cellular material 327. The flow channels allow fluid communication throughout that portion of the cellular material 327 having open cells. The cells and flow channels may be uniform in shape and size, or may include patterned or random variations in shape and size. Variations in shape and size of the cells of the cellular material 327 result in variations in the flow channels, and such characteristics can be used to alter the flow characteristics of fluid through the cellular material 327. The cellular material 327 may further include portions that include "closed cells." These closed-cell portions of the cellular material 327 contain a plurality of cells, the majority of which are not fluidly connected to adjacent cells. An example of a closed-cell portion is described above as a barrier layer that may be substituted for the flexible barrier 313. Similarly, closed-cell portions could be selectively disposed in the cellular material 327 to prevent transmission of fluids through the perimeter surfaces 330 of the cellular material 327.

The flexible barrier 313 and cellular material 327 may also be constructed from bioresorbable materials that do not have to be removed from a patient's body following use of the reduced-pressure delivery apparatus 311. Suitable bioresorbable materials may include, without limitation, a polymeric blend of polylactic acid (PLA) and polyglycolic acid (PGA). The polymeric blend may also include without limitation polycarbonates, polyfumarates, and capralactones. The flexible barrier 313 and the cellular material 327 may further serve as a scaffold for new cell-growth, or a scaffold material may be used in conjunction with the flexible barrier 313, flexible backing, or cellular material 327 to promote cell-growth. Suitable scaffold materials may include, without limitation, calcium phosphate, collagen, PLA/PGA, coral hydroxy apatites, carbonates, or processed allograft materials. Preferably, the scaffold material will have a high void-fraction (i.e. a high content of air).

A reduced-pressure delivery tube 341 is positioned within the arcuate channel 323 and is attached to the flexible barrier 313. The reduced-pressure delivery tube 341 may also be attached to the cellular material 327, or in the case of only a cellular material 327 being present, the reduced-pressure delivery tube 341 may be attached to only the cellular material 327. The reduced-pressure delivery tube 341 includes a distal orifice 343 at a distal end of the reduced-pressure delivery tube 341 similar to the distal orifice 243 of FIG. 5. The reduced-pressure delivery tube 341 may be positioned such that the distal orifice 343 is located at any point along the arcuate channel 323, but is preferably located approximately midway along the longitudinal length of the arcuate channel 323. The distal orifice 343 is preferably made elliptical or oval in shape by cutting the reduced-pressure delivery tube 341 along a plane that is oriented less than ninety (90) degrees to the longitudinal axis of the reduced-pressure delivery tube 341. While the orifice may also be round, the elliptical shape of the orifice increases fluid communication with the flow channels in the cellular material 327.

In one embodiment, the reduced-pressure delivery tube 341 may also include vent openings, or vent orifices (not shown) similar to vent openings 251 of FIG. 5. The vent openings are positioned along the reduced-pressure delivery tube 341 as either an alternative to the distal orifice 343 or in addition to the distal orifice 343 to further increase fluid communication between the reduced-pressure delivery tube 341 and the flow channels. As previously described, the reduced-pressure delivery tube 341 may be positioned along only a portion of the longitudinal length of the arcuate channel 323, or alternatively may be positioned along the entire longitudinal length of the arcuate channel 323. If positioned such that the reduced-pressure delivery tube 341 occupies the entire arcuate channel 323, the distal orifice 343 may be capped such that all fluid communication between the reduced-pressure delivery tube 341 and the flow channels occurs through the vent openings.

Preferably, the cellular material 327 overlays and directly contacts the reduced-pressure delivery tube 341. The cellular material 327 may be connected to the reduced-pressure delivery tube 341, or the cellular material 327 may simply be attached to the flexible barrier 313. If the reduced-pressure delivery tube 341 is positioned such that it only extends to a midpoint of the arcuate channel 323, the cellular material 327 may also be connected to the spine portion 315 of the flexible barrier 313 in that area of the arcuate channel 323 that does not contain the reduced-pressure delivery tube 341.

The reduced-pressure delivery tube 341 further includes a proximal orifice 355 at a proximal end of the reduced-pressure delivery tube 341. The proximal orifice 355 is configured to mate with a reduced-pressure source, which is described in more detail below with reference to FIG. 9. The reduced-pressure delivery tube 341 illustrated in FIGS. 6-8 includes only a single lumen, or passageway 359. It is possible, however, for the reduced-pressure delivery tube 341 to include multiple lumens such as those described previously with reference to FIG. 4B. The use of a multiple lumen tube provides separate paths of fluid communication between the proximal end of the reduced-pressure delivery tube 341 and the flow channels as previously described. These separate paths of fluid communication may also be provided by separate tubes having single or multiple lumens that communicate with the flow channels.

Referring primarily to FIGS. 8A and 8B, a reduced-pressure delivery apparatus 371 according to the principles of the present disclosure includes a reduced-pressure delivery tube 373 having an extension portion 375 at a distal end 377 of the reduced-pressure delivery tube 373. The extension portion 375 is preferably arcuately shaped to match the curvature of the reduced-pressure delivery tube 373. The extension portion 375 may be formed by removing a portion of the reduced-pressure delivery tube 373 at the distal end 377, thereby forming a cut-out 381 having a shoulder 383. A plurality of projections 385 is disposed on an inner surface 387 of the reduced-pressure delivery tube 373 to form a plurality of flow channels 391 between the projections 385. The projections 385 may be similar in size, shape, and spacing as the projections described with reference to FIGS. 1-5. The reduced-pressure delivery apparatus 371 is particularly suited for applying reduced pressure to and regenerating tissue on connective tissues that are capable of being received within the cut-out 381. Ligaments, tendons, and cartilage are non-limiting examples of the tissues that may be treated by reduced-pressure delivery apparatus 371.

Referring primarily to FIG. 9, a reduced-pressure delivery apparatus 411 similar to the other reduced-pressure delivery apparatuses described herein is used to apply a reduced-pressure tissue treatment to a tissue site 413, such as a human bone 415 of a patient. When used to promote bone tissue growth, reduced-pressure tissue treatment can increase the rate of healing associated with a fracture, a non-union, a void, or other bone defects. It is further believed that reduced-pressure tissue treatment may be used to improve recovery from osteomyelitis. The therapy may further be used to increase localized bone densities in patients suffering from osteoporosis. Finally, reduced-pressure tissue treatment may be used to speed and improve oseointegration of orthopedic implants such as hip implants, knee implants, and fixation devices.

Referring still to FIG. 9, the reduced-pressure delivery apparatus 411 includes a reduced-pressure delivery tube 419 having a proximal end 421 fluidly connected to a reduced-pressure source 427. The reduced-pressure source 427 is a pump or any other device that is capable of applying a reduced pressure to the tissue site 413 through the reduced-pressure delivery tube 419 and a plurality of flow channels associated with the reduced-pressure delivery apparatus 411. Applying reduced pressure to the tissue site 413 is accomplished by placing the wing portions of the reduced-pressure delivery apparatus 411 adjacent the tissue site 413, which in this particular example involves wrapping the wing portions around a void defect 429 in the bone 415. The reduced-pressure delivery apparatus 411 may be surgically or percutaneously inserted. When percutaneously inserted, the reduced-pressure delivery tube 419 is preferably inserted through a sterile insertion sheath that penetrates the skin tissue of the patient.

The application of reduced-pressure tissue treatment typically generates granulation tissue in the area surrounding the tissue site 413. Granulation tissue is a common tissue that often forms prior to tissue repair in the body. Under normal circumstances, granulation tissue may form in response to a foreign body or during wound healing. Granulation tissue typically serves as a scaffold for healthy replacement tissue and further results in the development of some scar tissue. Granulation tissue is highly vascularized, and the increased growth and growth rate of the highly vascularized tissue in the presence of reduced pressure promotes new tissue growth at the tissue site 413.

Referring still to FIG. 9, a fluid delivery tube 431 may be fluidly connected at a distal end to the flow channels of the reduced-pressure delivery apparatus 411. The fluid delivery tube 431 includes a proximal end 432 that is fluidly connected to a fluid delivery source 433. If the fluid being delivered to the tissue site is air, the air is preferably filtered by a filter 434 capable of filtering particles at least as small as 0.22 µm in order to clean and sterilize the air. The introduction of air to the tissue site 413, especially when the tissue site 413 is located beneath the surface of the skin, is important to facilitate good drainage of the tissue site 413, thereby reducing or preventing obstruction of the reduced-pressure delivery tube 419. The fluid delivery tube 431 and fluid delivery source 433 could also be used to introduce other fluids to the tissue site 413, including without limitation an antibacterial agent, an antiviral agent, a cell-growth promotion agent, an irrigation fluid, or other chemically active agents. When percutaneously inserted, the fluid delivery tube 431 is preferably inserted through a sterile insertion sheath that penetrates the skin tissue of the patient.

A pressure sensor 435 may be operably connected to the fluid delivery tube 431 to indicate whether the fluid delivery tube 431 is occluded with blood or other bodily fluids. The pressure sensor 435 may be operably connected to the fluid delivery source 433 to provide feedback so that the amount of fluid introduced to the tissue site 413 is controlled. A check valve (not shown) may also be operably connected near the distal end of the fluid delivery tube 431 to prevent blood or other bodily fluids from entering the fluid delivery tube 431.

The independent paths of fluid communication provided by reduced-pressure delivery tube 419 and fluid delivery tube 431 may be accomplished in a number of different ways, including that of providing a single, multi-lumen tube as described previously with reference to FIG. 4B. A person of ordinary skill in the art will recognize that the sensors, valves, and other components associated with the fluid delivery tube 431 could also be similarly associated with a particular lumen in the reduced-pressure delivery tube 419 if a multi-lumen tube is used. It is preferred that any lumen or tube that fluidly communicates with the tissue site be coated with an anti-coagulant to prevent a build-up of bodily fluids or blood within the lumen or tube. Other coatings that may coat the lumens or tubes include without limitation heparin, anti-coagulants, anti-fibrinogens, anti-adherents, anti-thrombinogens, and hydrophilic coatings.

Figure 10:
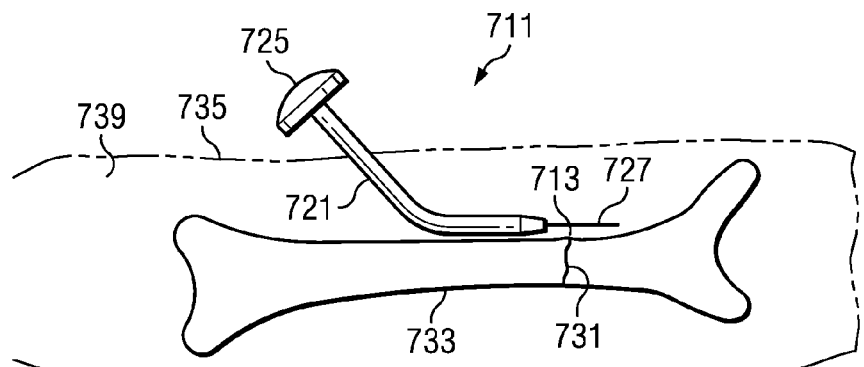
FIG. 10 depicts a front view of a reduced-pressure delivery system according to an embodiment of the present invention, the reduced-pressure delivery system having a manifold delivery tube that is used to percutaneously insert a reduced-pressure delivery apparatus to a tissue site.

Referring primarily to FIG. 10, a reduced-pressure delivery system 711 according to an embodiment of the present disclosure delivers reduced-pressure tissue treatment to a tissue site 713 of a patient. The reduced-pressure delivery system 711 includes a manifold delivery tube 721. The manifold delivery tube 721 may be a catheter or cannula and may include features, such as a steering unit 725 and a guide wire 727 that allow the manifold delivery tube 721 to be guided to the tissue site 713. Placement and direction of the guide wire 727 and the manifold delivery tube 721 may be accomplished by using endoscopy, ultrasound, fluoroscopy, auscultation, palpation, or any other suitable localization technique. The manifold delivery tube 721 is provided to percutaneously insert a reduced-pressure delivery apparatus to the tissue site 713 of the patient. When percutaneously inserted, the manifold delivery tube 721 is preferably inserted through a sterile insertion sheath that penetrates the skin tissue of the patient.

In FIG. 10, the tissue site 713 includes bone tissue adjacent a fracture 731 on a bone 733 of the patient. The manifold delivery tube 721 is inserted through the patient's skin 735 and any soft tissue 739 surrounding the bone 733. As previously discussed, the tissue site 713 may also include any other type of tissue, including, without limitation, adipose tissue, muscle tissue, neural tissue, dermal tissue, vascular tissue, connective tissue, cartilage, tendons, or ligaments.

Figure 11:
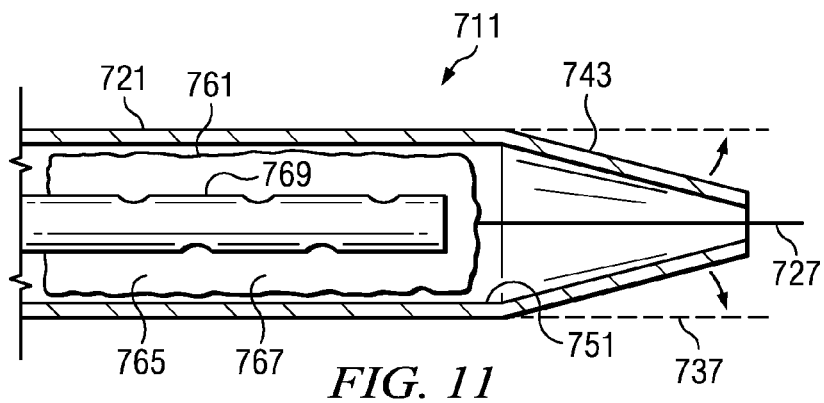
FIG. 11 illustrates an enlarged front view of the manifold delivery tube of FIG. 10, the manifold delivery tube containing a reduced-pressure delivery apparatus having a flexible barrier or a cellular material in a compressed position.
Figure 12:
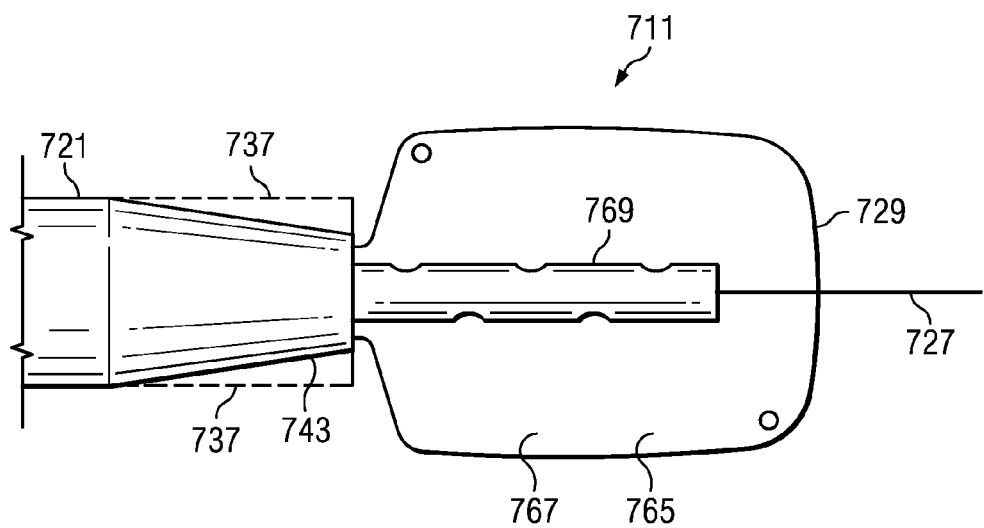
FIG. 12 depicts an enlarged front view of the manifold delivery tube of FIG. 11, the flexible barrier or cellular material of the reduced-pressure delivery apparatus being shown in an expanded position after having been pushed from the manifold delivery tube.

Referring primarily to FIGS. 11 and 12, the reduced-pressure delivery system 711 is further illustrated. The manifold delivery tube 721 may include a tapered distal end 743 to ease insertion through the patient's skin 735 and soft tissue 739 in FIG. 10. The tapered distal end 743 may further be configured to flex radially outward to an open position such that the inner diameter of the tapered distal end 743 would be substantially the same as or greater than the inner diameter at other portions of the tube 721. The open position of the tapered distal end 743 is schematically illustrated in FIG. 11 by broken lines 737.

The manifold delivery tube 721 further includes a passageway 751 in which a reduced-pressure delivery apparatus 761, or any other reduced-pressure delivery apparatus, is contained. The reduced-pressure delivery apparatus 761 includes a flexible barrier 765 or cellular material 767 similar to that described with reference to FIGS. 6-8. The flexible barrier 765 or cellular material 767 is preferably rolled, folded, or otherwise compressed around a reduced-pressure delivery tube 769 to reduce the cross-sectional area of the reduced-pressure delivery apparatus 761 within the passageway 751.

The reduced-pressure delivery apparatus 761 may be placed within the passageway 751 and guided to the tissue site 713 following the placement of the tapered distal end 743 manifold delivery tube 721 at the tissue site 713. Alternatively, the reduced-pressure delivery apparatus 761 may be pre-positioned within the passageway 751 prior to the manifold delivery tube 721 being inserted into the patient. If the reduced-pressure delivery apparatus 761 is to be pushed through the passageway 751, a biocompatible lubricant may be used to reduce friction between the reduced-pressure delivery apparatus 761 and the manifold delivery tube 721. When the tapered distal end 743 has been positioned at the tissue site 713 and the reduced-pressure delivery apparatus 761 has been delivered to the tapered distal end 743, the reduced-pressure delivery apparatus 761 is then pushed toward the tapered distal end 743, causing the tapered distal end 743 to expand radially outward into the open position. The reduced-pressure delivery apparatus 761 is pushed out of the manifold delivery tube 721, preferably into a void or space adjacent the tissue site 713. The void or space is typically formed by dissection of soft tissue, which may be accomplished by percutaneous means. In some cases, the tissue site 713 may be located at a wound site, and a void may be naturally present due to the anatomy of the wound. In other instances, the void may be created by balloon dissection, sharp dissection, blunt dissection, hydrodissection, pneumatic dissection, ultrasonic dissection, electrocautery dissection, laser dissection, or any other suitable dissection technique. When the reduced-pressure delivery apparatus 761 enters the void adjacent the tissue site 713, the flexible barrier 765 or cellular material 767 of the reduced-pressure delivery apparatus 761 either unrolls, unfolds, or decompresses (see FIG. 12) such that the reduced-pressure delivery apparatus 761 can be placed in contact with the tissue site 713. Although not required, the flexible barrier 765 or cellular material 767 may be subjected to a vacuum or reduced pressure supplied through the reduced-pressure delivery tube 769 to compress the flexible barrier 765 or cellular material 767. The unfolding of the flexible barrier 765 or cellular material 767 may be accomplished by either relaxing the reduced pressure supplied through the reduced-pressure delivery tube 769 or by supplying a positive pressure through the reduced-pressure delivery tube 769 to assist the unrolling process. Final placement and manipulation of the reduced-pressure delivery apparatus 761 may be accomplished by using endoscopy, ultrasound, fluoroscopy, auscultation, palpation, or any other suitable localization technique. Following placement of the reduced-pressure delivery apparatus 761, the manifold delivery tube 721 is preferably removed from the patient, but the reduced-pressure delivery tube associated with reduced-pressure delivery apparatus 761 remains in situ to allow percutaneous application of reduced pressure to the tissue site 713.

Figure 13:
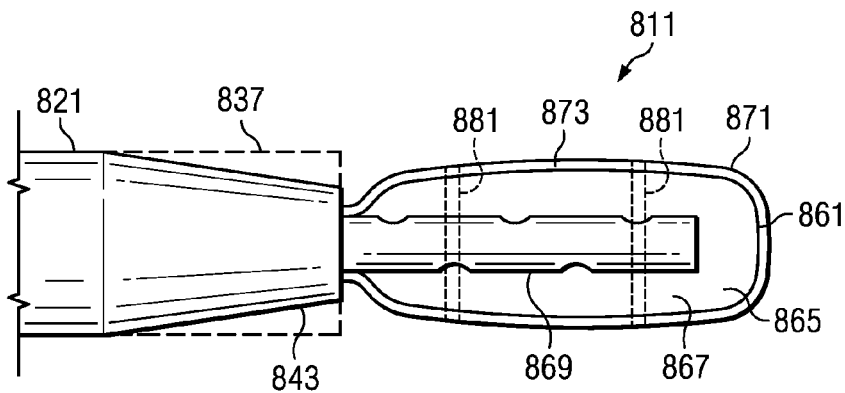
FIG. 13 illustrates a front view of a reduced-pressure delivery system according to an embodiment of the present invention, the reduced-pressure delivery system having a manifold delivery tube that is used to percutaneously insert a reduced-pressure delivery apparatus to a tissue site, the reduced-pressure delivery apparatus being shown outside of the manifold delivery tube but constrained by an impermeable membrane in a compressed position.
Figure 14:
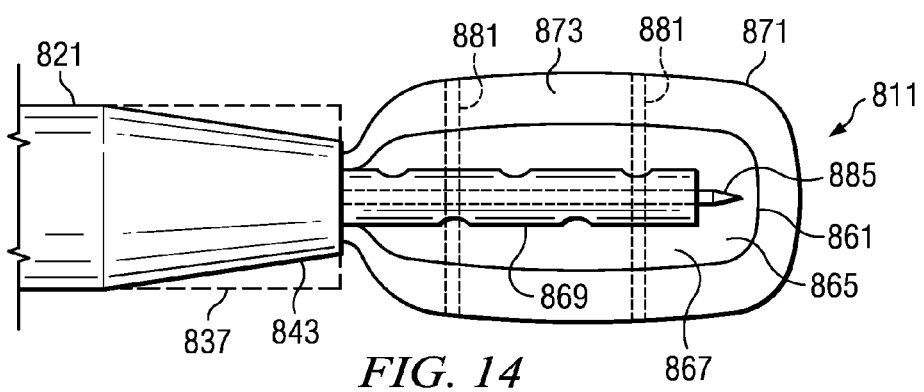
FIG. 14 depicts a front view of the reduced-pressure delivery system of FIG. 13, the reduced-pressure delivery apparatus being shown outside of the manifold delivery tube but constrained by an impermeable membrane in a relaxed position.
Figure 15:
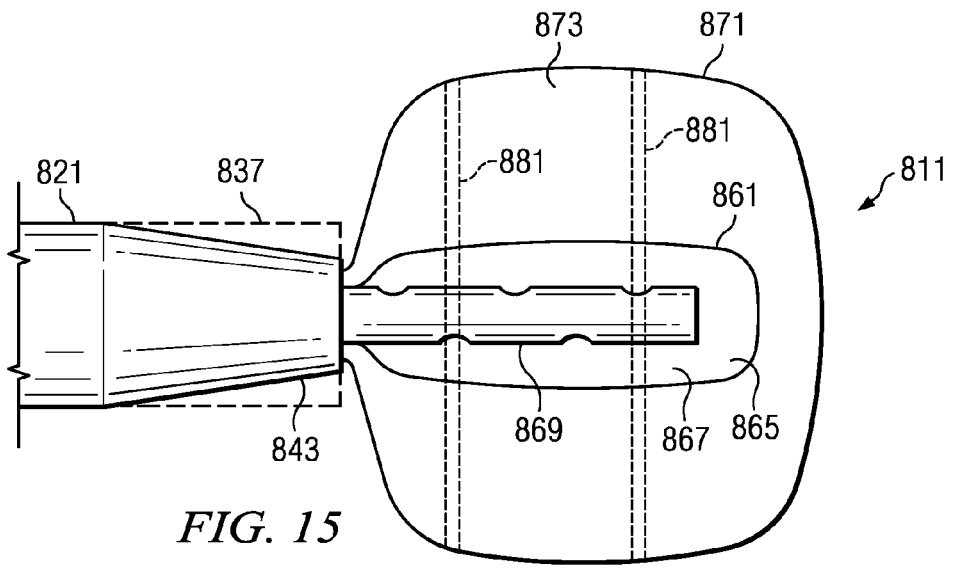
FIG. 15 illustrates a front view of the reduced-pressure delivery system of FIG. 13, the reduced-pressure delivery apparatus being shown outside of the manifold delivery tube but constrained by an impermeable membrane in an expanded position.

Referring primarily to FIGS. 13-15, a reduced-pressure delivery system 811 according to an embodiment of the present disclosure includes a manifold delivery tube 821 having a tapered distal end 843 that is configured to flex radially outward to an open position such that the inner diameter of the distal end 843 would be substantially the same as or greater than the inner diameter at other portions of the manifold delivery tube 821. The open position of the distal end 843 is schematically illustrated in FIGS. 13-15 by broken lines 837.

The manifold delivery tube 821 further includes a passageway in which a reduced-pressure delivery apparatus 861 similar to the other reduced-pressure delivery apparatuses described herein is contained. The reduced-pressure delivery apparatus 861 includes a flexible barrier 865 or a cellular material 867 that is preferably rolled, folded, or otherwise compressed around a reduced-pressure delivery tube 869 to reduce the cross-sectional area of the reduced-pressure delivery apparatus 861 within the passageway.

An impermeable membrane 871 having an inner space 873 is disposed around the reduced-pressure delivery apparatus 861 such that the reduced-pressure delivery apparatus 861 is contained within the inner space 873 of the impermeable membrane 871. The impermeable membrane 871 may be a balloon, a sheath, or any other type of membrane that is capable of preventing fluid transmission such that the impermeable membrane 871 can assume at least one of a compressed position (see FIG. 13), a relaxed position (see FIG. 14), and an expanded position (see FIGS. 15 and 15A). The impermeable membrane 871 may be sealingly connected to the manifold delivery tube 821 such that the inner space 873 of the impermeable membrane 871 is in fluid communication with the passageway of the manifold delivery tube 821. The impermeable membrane 871 may alternatively be attached to the reduced-pressure delivery tube 869 such that the inner space 873 of the impermeable membrane 871 is in fluid communication with the passageway of the reduced-pressure delivery tube 869. The impermeable membrane 871 instead may be attached to a separate control tube or control lumen (see for example FIG. 15A) that fluidly communicates with the inner space 873.

In one embodiment, the impermeable membrane 871 may be provided to further reduce the cross-sectional area of the reduced-pressure delivery apparatus 861 within the passageway. To accomplish this, a pressure is applied to the inner space 873 of the impermeable membrane 871 that is less than the ambient pressure surrounding the impermeable membrane 871. A significant portion of the air or other fluid within the inner space 873 is thereby evacuated, placing the impermeable membrane 871 in the compressed position illustrated in FIG. 13. In the compressed position, the impermeable membrane 871 is drawn inward such that a compressive force is applied to the reduced-pressure delivery apparatus 861 to further reduce the cross-sectional area of the reduced-pressure delivery apparatus 861. As previously described with reference to FIGS. 11 and 12, the reduced-pressure delivery apparatus 861 may be delivered to the tissue site following the placement of the distal end 843 of the manifold delivery tube 821 at the tissue site. Placement and manipulation of the impermeable membrane 871 and the reduced-pressure delivery apparatus 861 may be accomplished by using endoscopy, ultrasound, fluoroscopy, auscultation, palpation, or any other suitable localization technique. The impermeable membrane 871 may include radio-opaque markers 881 that improve visualization of the impermeable membrane 871 under fluoroscopy prior to its removal.

After pushing the reduced-pressure delivery apparatus 861 through the distal end 843, the reduced pressure applied to the inner space 873 may be eased to place the impermeable membrane 871 in the relaxed position (see FIG. 14), thereby facilitating easier removal of the reduced-pressure delivery apparatus 861 from the impermeable membrane 871. A removal instrument 885, such as a trocar, stylet, or other sharp instrument may be provided to rupture the impermeable membrane 871. Preferably, the removal instrument 885 is inserted through the reduced-pressure delivery tube 869 and is capable of being advanced into contact with the impermeable membrane 871. After rupture of the impermeable membrane 871, the removal instrument 885 and the impermeable membrane 871 may be withdrawn through the manifold delivery tube 821, allowing the flexible barrier 865 or cellular material 867 of the reduced-pressure delivery apparatus 861 to unroll, unfold, or decompress such that the reduced-pressure delivery apparatus 861 can be placed in contact with the tissue site. The unrolling of the flexible barrier 865 or cellular material 867 may occur automatically following the relaxation of reduced pressure to the inner space 873 and the removal of the impermeable membrane 871. In some cases, a positive pressure may be delivered through the reduced-pressure delivery tube 869 to assist in unrolling or decompressing the flexible barrier 865 or cellular material 867. Following final placement of the reduced-pressure delivery apparatus 861, the manifold delivery tube 821 is preferably removed from the patient, but the reduced-pressure delivery tube 869 associated with the reduced-pressure delivery apparatus 861 remains in situ to allow percutaneous application of reduced pressure to the tissue site.

The impermeable membrane 871 may also be used to dissect tissue adjacent the tissue site prior to placing the reduced-pressure delivery apparatus 861 against the tissue site. After pushing the reduced-pressure delivery apparatus 861 and intact impermeable membrane 871 through the distal end 843 of the manifold delivery tube 821, air or another fluid may be injected or pumped into the inner space 873 of the impermeable membrane 871. A liquid is preferably used to inflate the impermeable membrane 871 since the incompressibility of liquids allow the impermeable membrane 871 to expand more evenly and consistently. The impermeable membrane 871 may expand radially as illustrated in FIG. 15 or directionally depending on its method of manufacture and attachment to the manifold delivery tube 821. As the impermeable membrane 871 expands outward into the expanded position (see FIG. 15) due to the pressure of the air or fluid, a void is dissected adjacent the tissue site. When the void is large enough, the liquid, air or other fluid may be released from the inner space 873 to allow the impermeable membrane 871 to assume the relaxed position. The impermeable membrane 871 may then be ruptured as previously explained and the reduced-pressure delivery apparatus 861 inserted adjacent the tissue site.

Figure 15A:
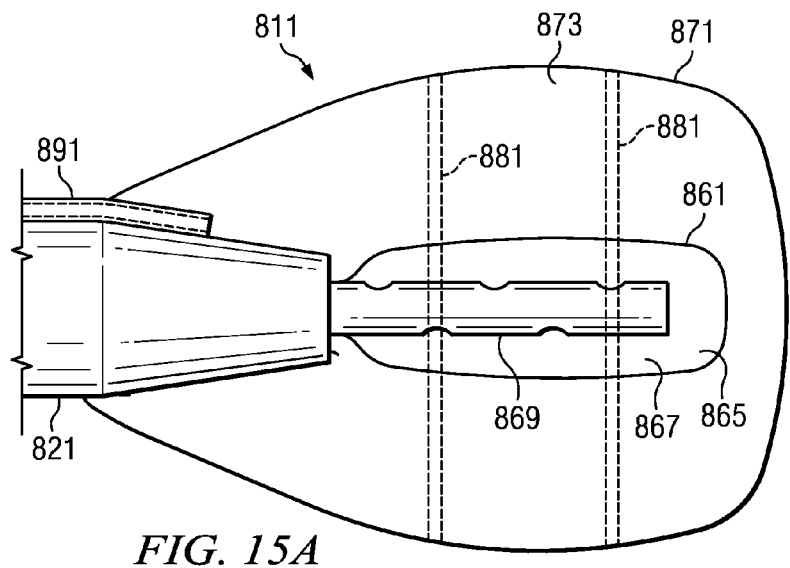
FIG. 15A illustrates a front view of the reduced-pressure delivery system of FIG. 13, the reduced-pressure delivery apparatus being shown outside of the manifold delivery tube but surrounded by an impermeable membrane in an expanded position.

Referring primarily to FIG. 15A, if the impermeable membrane 871 is used primarily to dissect tissue adjacent the tissue site, the impermeable membrane 871 may be sealingly attached to the manifold delivery tube 821 such that the inner space 873 fluidly communicates with a secondary lumen, or tube 891, associated with or attached to the manifold delivery tube 821. The secondary lumen 891 may be used to deliver a liquid, air, or other fluid to the inner space 873 to place the impermeable membrane 871 in the expanded position. Following dissection, the impermeable membrane 871 may be relaxed and ruptured as previously described with reference to FIG. 14.

Figure 16:
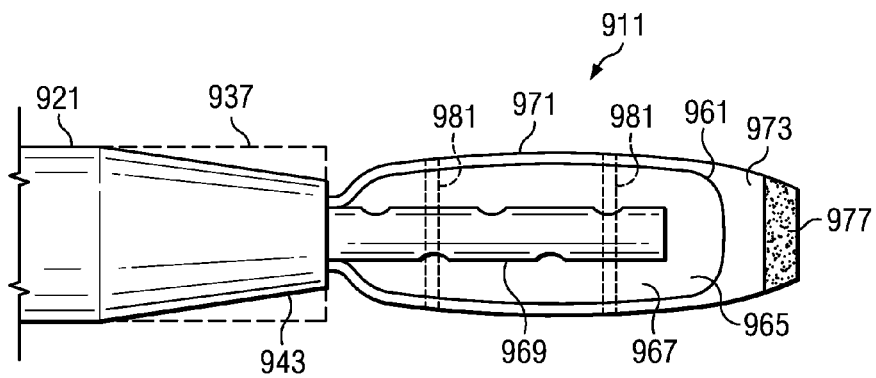
FIG. 16 depicts a front view of a reduced-pressure delivery system according to an embodiment of the present invention, the reduced-pressure delivery system having a manifold delivery tube that is used to percutaneously insert a reduced-pressure delivery apparatus to a tissue site, the reduced-pressure delivery apparatus being shown outside of the manifold delivery tube but constrained by an impermeable membrane having a glue seal.

Referring primarily to FIG. 16, a reduced-pressure delivery system 911 according to an embodiment of the present disclosure includes a manifold delivery tube 921 having a tapered distal end 943 that is configured to flex radially outward to an open position such that the inner diameter of the distal end 943 would be substantially the same as or greater than the inner diameter at other portions of the manifold delivery tube 921. The open position of the distal end 943 is schematically illustrated in FIG. 16 by broken lines 937.

The manifold delivery tube 921 further includes a passageway in which a reduced-pressure delivery apparatus 961 similar to the other reduced-pressure delivery apparatuses described herein is contained. The reduced-pressure delivery apparatus 961 includes a flexible barrier 965 or a cellular material 967 that is preferably rolled, folded, or otherwise compressed around a reduced-pressure delivery tube 969 to reduce the cross-sectional area of the reduced-pressure delivery apparatus 961 within the passageway of the manifold delivery tube 921.

An impermeable membrane 971 having an inner space 973 is disposed around the reduced-pressure delivery apparatus 961 such that the reduced-pressure delivery apparatus 961 is contained within the inner space 973 of the impermeable membrane 971. The impermeable membrane 971 includes a glue seal 977 on one end of the impermeable membrane 971 to provide an alternative method of removing the reduced-pressure delivery apparatus 961 from the impermeable membrane 971. The impermeable membrane 971 may be sealingly connected at another end to the manifold delivery tube 921 such that the inner space 973 of the impermeable membrane 971 is in fluid communication with the passageway of the manifold delivery tube 921. Alternatively, the impermeable membrane 971 may be attached to a separate control tube (not shown) that fluidly communicates with the inner space 973.

Similar to the impermeable membrane 871 of FIG. 13, impermeable membrane 971 may be capable of preventing fluid transmission such that the impermeable membrane 971 can assume at least one of a compressed position, a relaxed position, and an expanded position. Since the procedures for placing the impermeable membrane 971 in a compressed position and an expanded position are similar to those for impermeable membrane 871, only the differing process of removing the reduced-pressure delivery apparatus 961 is described.

The reduced-pressure delivery apparatus 961 is delivered to the tissue site within the impermeable membrane 971 and then properly positioned using endoscopy, ultrasound, fluoroscopy, auscultation, palpation, or any other suitable localization technique. The impermeable membrane 971 may include radio-opaque markers 981 that improve visualization of the impermeable membrane 971 under fluoroscopy prior to its removal. The reduced-pressure delivery apparatus 961 is then pushed through the distal end 943 of the manifold delivery tube 921. The reduced pressure applied to the inner space 973 may be eased to place the impermeable membrane 971 in the relaxed position. The reduced-pressure delivery apparatus 961 is then pushed through the glue seal 977 to exit the impermeable membrane 971.

Figure 16A:
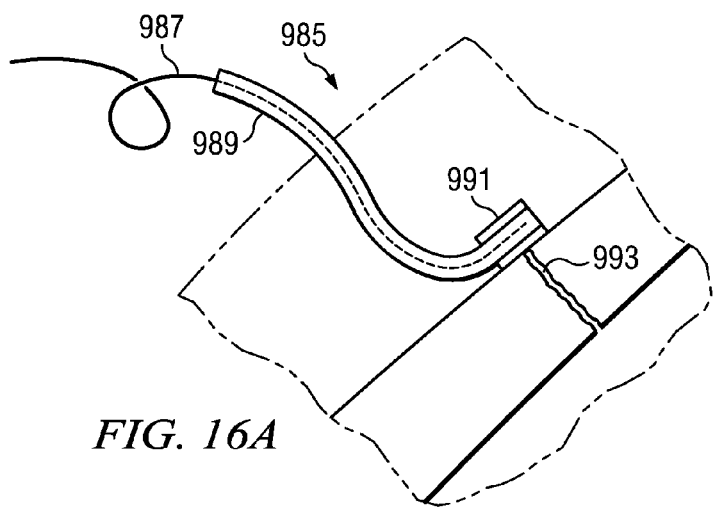
FIG. 16A depicts a front view of a reduced-pressure delivery system according to an embodiment of the present invention.

Referring primarily to FIG. 16A, a reduced-pressure delivery system 985 according to an embodiment of the present disclosure may not include a manifold delivery tube similar to manifold delivery tube 921 of FIG. 16. Instead, the reduced-pressure delivery system 985 may include a guide wire 987, a reduced-pressure delivery tube 989, and a reduced-pressure delivery apparatus 991. The reduced-pressure delivery apparatus 991 includes a plurality flow channels that is fluidly connected to the reduced-pressure delivery tube 989. Instead of using an independent manifold delivery tube to deliver the reduced-pressure delivery apparatus 991, the reduced-pressure delivery apparatus 991 and reduced-pressure delivery tube 989 are placed on the guide wire 987, which is percutaneously guided to a tissue site 993. Preferably, the guide wire 987 and reduced-pressure delivery tube 989 penetrate the skin of the patient through a sterile sheath. By guiding the reduced-pressure delivery tube 989 and reduced-pressure delivery apparatus 991 along the guide wire 987, the reduced-pressure delivery apparatus 991 may be placed at the tissue site 993 to allow percutaneous application of reduced-pressure tissue treatment.

Since the reduced-pressure delivery apparatus 991 is not constrained within a manifold delivery tube during delivery to the tissue site 993, it is preferable to hold the reduced-pressure delivery apparatus 991 in a compressed position during delivery. If an elastic foam is used as the reduced-pressure delivery apparatus 991, a biocompatible, soluble adhesive may be applied to the foam and the foam compressed. Upon arrival at the tissue site, bodily fluids or other fluids delivered through the reduced-pressure delivery tube 989 dissolve the adhesive, allowing the foam to expand into contact with the tissue site. Alternatively, the reduced-pressure delivery apparatus 991 may be formed from a compressed, dry hydrogel. The hydrogel absorbs moisture following delivery to the tissue site 993 allowing expansion of the reduced-pressure delivery apparatus 991. Still another reduced-pressure delivery apparatus 991 may be made from a thermoactive material (e.g., polyethylene glycol) that expands at the tissue site 993 when exposed to the body heat of the patient. In still another embodiment, a compressed reduced-pressure delivery apparatus 991 may be delivered to the tissue site 993 in a dissolvable membrane.

Figure 17:
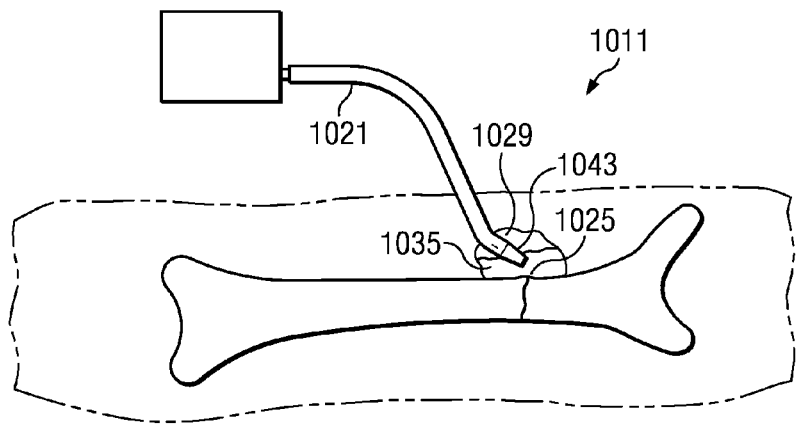
FIG. 17 illustrates a front view of a reduced-pressure delivery system according to an embodiment of the present invention, the reduced-pressure delivery system having a manifold delivery tube that is used to percutaneously inject a reduced-pressure delivery apparatus to a tissue site.

Referring primarily to FIG. 17, a reduced-pressure delivery system 1011 according to an embodiment of the present disclosure includes a manifold delivery tube 1021 having a distal end 1043 that is inserted through a tissue of a patient to access a tissue site 1025. The tissue site 1025 may include a void 1029 that is associated with a wound or other defect, or alternatively a void may be created by dissection, including the dissection techniques described herein.

Following placement of the distal end 1043 within the void 1029 adjacent the tissue site 1025, an injectable, pourable, or flowable reduced-pressure delivery apparatus 1035 is delivered through the manifold delivery tube 1021 to the tissue site 1025. The reduced-pressure delivery apparatus 1035 preferably exists in a flowable state during delivery to the tissue site, and then, after arrival forms a plurality of flow channels for distribution of reduced pressure or fluids. In some cases, the flowable material may harden into a solid state after arrival at the tissue site, either through a drying process, a curing process, or other chemical or physical reaction. In other cases, the flowable material may form a foam in situ following delivery to the tissue site. Still other materials may exist in a gel-like state at the tissue site 1025 but still have a plurality of flow channels for delivering reduced pressure. The amount of reduced-pressure delivery apparatus 1035 delivered to the tissue site 1025 may be enough to partially or completely fill the void 1029. The reduced-pressure delivery apparatus 1035 may include aspects of both a manifold and a scaffold. As a manifold, the reduced-pressure delivery apparatus 1035 includes a plurality of pores or open cells that may be formed in the material after delivery to the void 1029. The pores or open cells communicate with one another, thereby creating a plurality of flow channels. The flow channels are used to apply and distribute reduced pressure to the tissue site 1025. As a scaffold, the reduced-pressure delivery apparatus 1035 is bioresorbable and serves as a substrate upon and within which new tissue may grow.

In one embodiment, the reduced-pressure delivery apparatus 1035 may include poragens, such as NaCl or other salts that are distributed throughout a liquid or viscous gel. After the liquid or viscous gel is delivered to the tissue site 1025, the material conforms to the void 1029 and then cures into a solid mass. The water-soluble NaCl poragens dissolve in the presence of bodily fluids leaving a structure with interconnected pores, or flow channels. Reduced pressure or fluid is delivered to the flow channels. As new tissue develops, the tissue grows into the pores of the reduced-pressure delivery apparatus 1035, and then ultimately replaces the reduced-pressure delivery apparatus 1035 as it degrades. In this particular example, the reduced-pressure delivery apparatus 1035 serves not only as a manifold, but also as a scaffold for new tissue growth.

In another embodiment, the reduced-pressure delivery apparatus 1035 is an alginate mixed with 400 μm mannose beads. The poragens or beads may be dissolved by local body fluids or by irrigational or other fluids delivered to the reduced-pressure delivery apparatus 1035 at the tissue site. Following dissolution of the poragens or beads, the spaces previously occupied by the poragens or beads become voids that are interconnected with other voids to form the flow channels within the reduced-pressure delivery apparatus 1035.

The use of poragens to create flow channels in a material is effective, but it also forms pores and flow channels that are limited in size to approximately the particle size of the selected poragen. Instead of poragens, a chemical reaction may be used to create larger pores due to the formation of gaseous by-products. For example, in one embodiment, a flowable material may be delivered to the tissue site 1025 that contains sodium bicarbonate and citric acid particles (non-stoichiometric amounts may be used). As the flowable material forms a foam or solid in situ, bodily fluids will initiate an acid-base reaction between the sodium bicarbonate and the citric acid. The resulting carbon dioxide gas particles that are produced create larger pore and flow channels throughout the reduced-pressure delivery apparatus 1035 than techniques relying on poragen dissolution.

The transformation of the reduced-pressure delivery apparatus 1035 from a liquid or viscous gel into a solid or a foam can be triggered by pH, temperature, light, or a reaction with bodily fluids, chemicals, or other substances delivered to the tissue site. The transformation may also occur by mixing multiple reactive components. In one embodiment, the reduced-pressure delivery apparatus 1035 is prepared by selecting bioresorbable microspheres made from any bioresorbable polymer. The microspheres are dispersed in a solution containing a photoinitiator and a hydrogel-forming material, such as hyaluronic acid, collagen, or polyethylene glycol with photoreactive groups. The microsphere-gel mixture is exposed to light for a brief period of time to partially crosslink the hydrogel and immobilize the hydrogel on the microspheres. The excess solution is drained, and the microspheres are then dried. The microspheres are delivered to the tissue site by injection or pouring, and following delivery, the mixture absorbs moisture, and the hydrogel coating becomes hydrated. The mixture is then again exposed to light, which cross-links the microspheres, creating a plurality of flow channels. The cross-linked microspheres then serve as a manifold to deliver reduced pressure to the tissue site and as a porous scaffold to promote new tissue growth.

In addition to the preceding embodiments described herein, the reduced-pressure delivery apparatus 1035 may be made from a variety of materials, including, without limitation, calcium phosphate, collagen, alginate, cellulose, or any other equivalent material that is capable of being delivered to the tissue site as a gas, liquid, gel, paste, putty, slurry, suspension, or other flowable material and is capable of forming multiple flow paths in fluid communication with the tissue site. The flowable material may further include particulate solids, such as beads, that are capable of flowing through the manifold delivery tube 1021 if the particulate solids are sufficiently small in size. Materials that are delivered to the tissue site in a flowable state may polymerize or gel in situ.

Figure 17A:
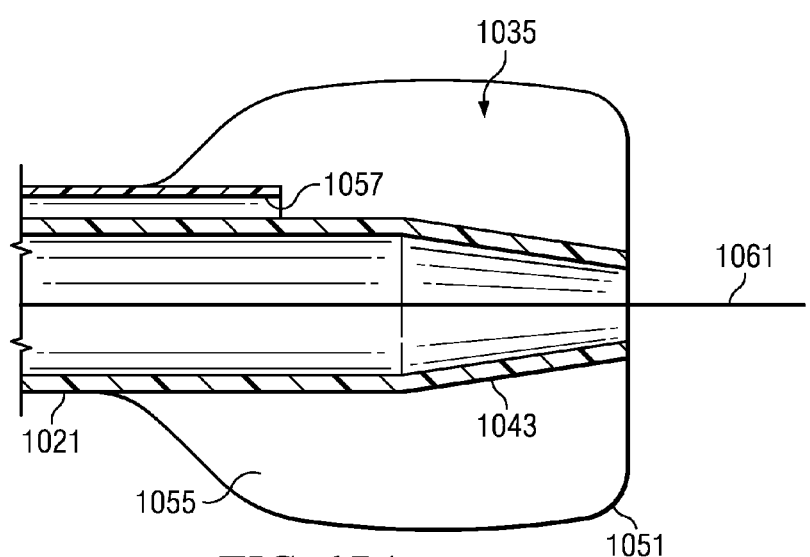
FIG. 17A illustrates a front view of a reduced-pressure delivery system according to an embodiment of the present invention, the reduced-pressure delivery system having a manifold delivery tube that is used to percutaneously deliver a reduced-pressure delivery apparatus to an impermeable membrane positioned at a tissue site.

As previously described, the reduced-pressure delivery apparatus 1035 may be injected or poured directly into the void 1029 adjacent the tissue site 1025. Referring primarily to FIG. 17A, the manifold delivery tube 1021 may include an impermeable or semi-permeable membrane 1051 at the distal end 1043 of the manifold delivery tube 1021. The membrane 1051 includes an inner space 1055 that fluidly communicates with a secondary lumen 1057 attached to the manifold delivery tube 1021. The manifold delivery tube 1021 is guided to the tissue site 1025 over a guide wire 1061.

The reduced-pressure delivery apparatus 1035 may be injected or poured through the secondary lumen 1057 to fill the inner space 1055 of the membrane 1051. As the fluid or gel fills the membrane 1051, the membrane 1051 expands to fill the void 1029 such that the membrane is in contact with the tissue site 1025. As the membrane 1051 expands, the membrane 1051 may be used to dissect additional tissue adjacent or near the tissue site 1025. The membrane 1051, if impermeable, may be physically ruptured and removed, leaving behind the reduced-pressure delivery apparatus 1035 in contact with the tissue site 1025. Alternatively, the membrane 1051 may be made from a dissolvable material that dissolves in the presence of bodily fluids or biocompatible solvents that may be delivered to the membrane 1051. If the membrane 1051 is semi-permeable, the membrane 1051 may remain in situ. The semi-permeable membrane 1051 allows communication of reduced pressure and possibly other fluids to the tissue site 1025.

Figure 18:
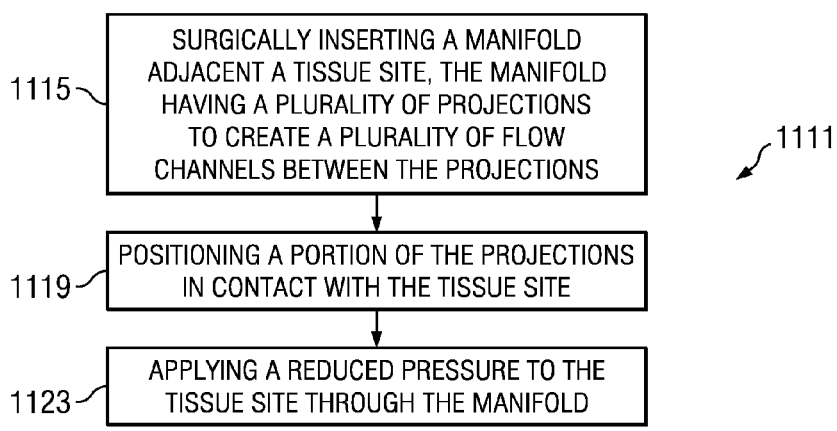
FIG. 18 depicts a flow chart of a method of administering a reduced-pressure tissue treatment to a tissue site according to an embodiment of the present invention.

Referring primarily to FIG. 18, a method 1111 of administering a reduced-pressure tissue treatment to a tissue site includes at 1115 surgically inserting a manifold adjacent the tissue site, the manifold having a plurality of projections extending from a flexible barrier to create a plurality of flow channels between the projections. The manifold is positioned at 1119 such that at least a portion of the projections are in contact with the tissue site. At 1123, a reduced pressure is applied through the manifold to the tissue site.

Figure 19:
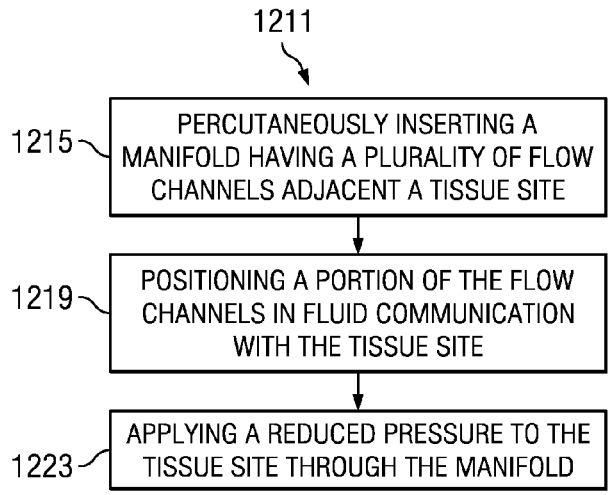
FIG. 19 illustrates a flow chart of a method of administering a reduced-pressure tissue treatment to a tissue site according to an embodiment of the present invention.

Referring primarily to FIG. 19, a method 1211 of administering a reduced-pressure tissue treatment to a tissue site includes at 1215 percutaneously inserting a manifold adjacent the tissue site. The manifold may include a plurality of projections extending from a flexible barrier to create a plurality of flow channels between the projections. Alternatively, the manifold may include cellular material having a plurality of flow channels within the cellular material. Alternatively, the manifold may be formed from an injectable or pourable material that is delivered to the tissue site and forms a plurality of flow channels after arriving at the tissue site. At 1219, the manifold is positioned such that at least a portion of the flow channels are in fluid communication with the tissue site. A reduced pressure is applied to the tissue site through the manifold at 1223.

Figure 20:
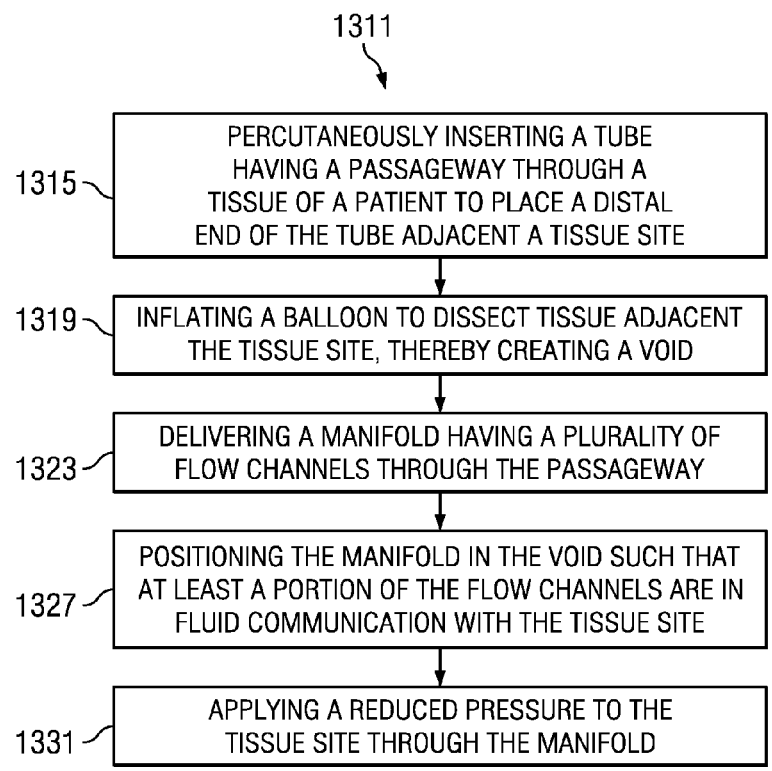
FIG. 20 depicts a flow chart of a method of administering a reduced-pressure tissue treatment to a tissue site according to an embodiment of the present invention.

Referring primarily to FIG. 20, a method 1311 of administering a reduced-pressure tissue treatment to a tissue site includes at 1315 percutaneously inserting a tube having a passageway through a tissue of a patient to place a distal end of the tube adjacent the tissue site. At 1319, a balloon associated with the tube may be inflated to dissect tissue adjacent the tissue site, thereby creating a void. At 1323, a manifold is delivered through the passageway. The manifold may include a plurality of projections extending from a flexible barrier to create a plurality of flow channels between the projections. Alternatively, the manifold may include cellular material having a plurality of flow channels within the cellular material. Alternatively, the manifold may be formed from an injectable or pourable material that is delivered to the tissue site as described previously with reference to FIG. 17. The manifold is positioned in the void at 1327 such that at least a portion of the flow channels are in fluid communication with the tissue site. At 1331, a reduced pressure is applied to the tissue site through the manifold via a reduced-pressure delivery tube or any other delivery means.

Figure 21:
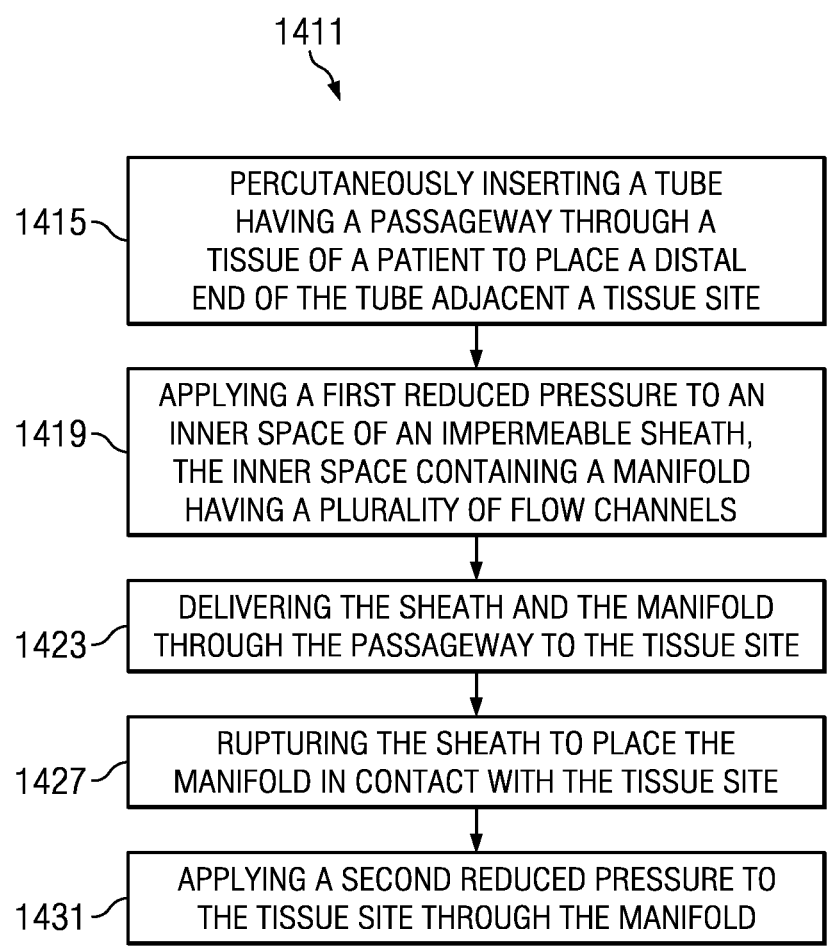
FIG. 21 illustrates a flow chart of a method of administering a reduced-pressure tissue treatment to a tissue site according to an embodiment of the present invention.

Referring primarily to FIG. 21, a method 1411 of administering a reduced-pressure tissue treatment to a tissue site includes at 1415 percutaneously inserting a tube having a passageway through a tissue of a patient to place a distal end of the tube adjacent the tissue site. At 1423, a manifold is delivered through the passageway to the tissue site within an impermeable sheath, the impermeable sheath at 1419 having been subjected to a first reduced pressure less than an ambient pressure of the sheath. At 1427, the sheath is ruptured to place the manifold in contact with the tissue site. At 1431, a second reduced pressure is applied through the manifold to the tissue site.

Figure 22:
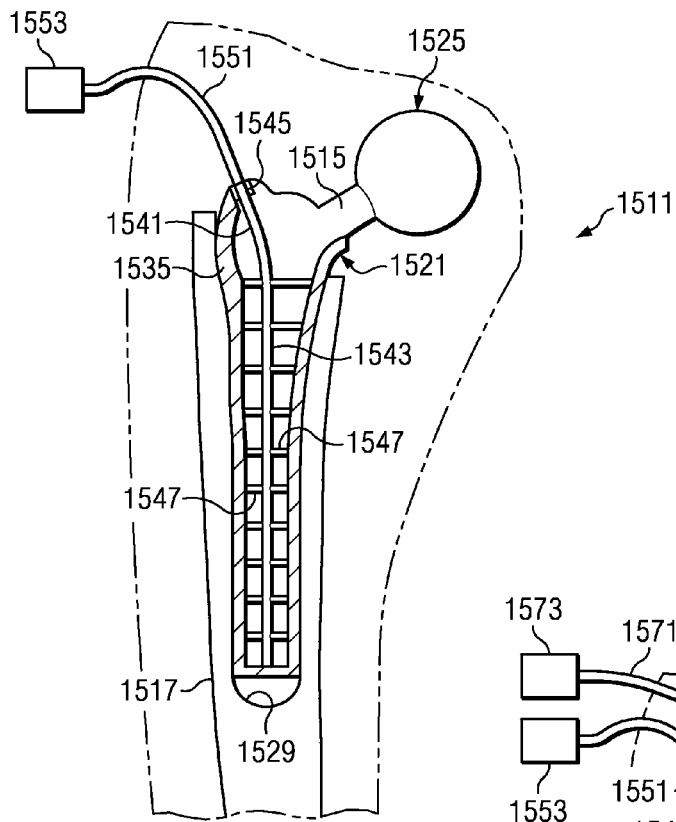
FIG. 22 depicts a cross-sectional front view of a reduced-pressure delivery apparatus according to an embodiment of the present invention, the reduced-pressure delivery apparatus including a hip prosthesis having a plurality of flow channels for applying a reduced pressure to an area of bone surrounding the hip prosthesis.
Figure 23:
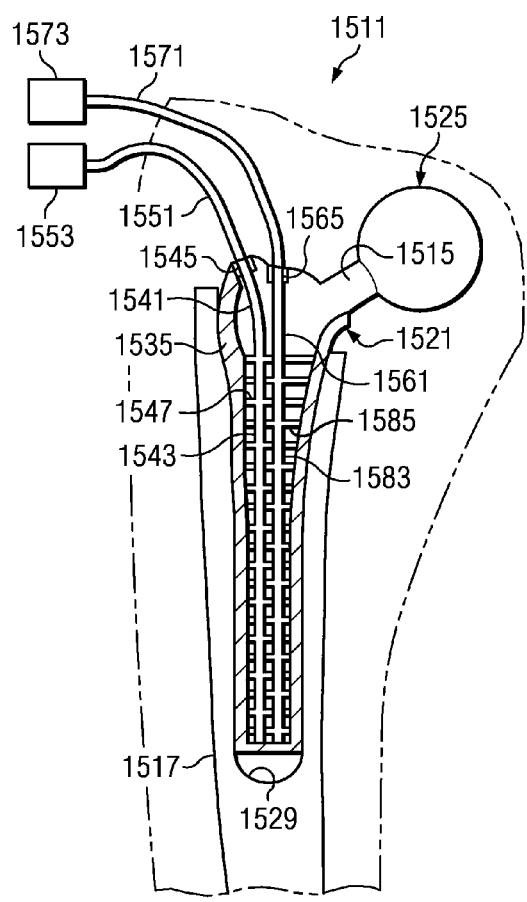
FIG. 23 illustrates a cross-sectional front view of the hip prosthesis of FIG. 22 having a second plurality of flow channels for delivering a fluid to the area of bone surrounding the hip prosthesis.

Referring primarily to FIGS. 22 and 23, a reduced-pressure delivery apparatus 1511 according to an embodiment of the present disclosure includes an orthopedic hip prosthesis 1515 for replacing the existing femoral head of a femur 1517 of a patient. The hip prosthesis 1515 includes a stem portion 1521 and a head portion 1525. The stem portion 1521 is elongated for insertion within a passage 1529 reamed in a shaft of the femur 1517. A porous coating 1535 is disposed around the stem portion and preferably is constructed from sintered or vitrified ceramics or metal. Alternatively, a cellular material having porous characteristic could be disposed around the stem portion. A plurality of flow channels 1541 is disposed within the stem portion 1521 of the hip prosthesis 1515 such that the flow channels 1541 are in fluid communication with the porous coating 1535. A connection port 1545 is fluidly connected to the flow channels 1541, the port being configured for releasable connection to a reduced-pressure delivery tube 1551 and a reduced-pressure delivery source 1553. The flow channels 1541 are used to deliver a reduced pressure to the porous coating 1535 or the bone surrounding the hip prosthesis 1515 following implantation. The flow channels 1541 may include a main feeder line 1543 that fluidly communicates with several lateral branch lines 1547, which communicate with the porous coating 1535. The lateral branch lines 1547 may be oriented normal to the main feeder line 1543 as illustrated in FIG. 22, or may be oriented at angles to the main feeder line 1543. An alternative method for distributing the reduced pressure includes providing a hollow hip prosthesis, and filling the inner space of the prosthesis with a cellular (preferably open-cell) material that is capable of fluidly communicating with the porous coating 1535.

Referring more specifically to FIG. 23, hip prosthesis 1515 may further include a second plurality of flow channels 1561 within the stem portion 1521 to provide a fluid to the porous coating 1535 or the bone surrounding the hip prosthesis 1515. The fluid could include filtered air or other gases, antibacterial agents, antiviral agents, cell-growth promotion agents, irrigation fluids, chemically active fluids, or any other fluid. If it is desired to introduce multiple fluids to the bone surrounding the hip prosthesis 1515, additional paths of fluid communication may be provided. A connection port 1565 is fluidly connected to the flow channels 1561, the connection port 1565 being configured for releasable connection to a fluid delivery tube 1571 and a fluid delivery source 1573. The flow channels 1561 may include a main feeder line 1583 that fluidly communicates with several lateral branch lines 1585, which communicate with the porous coating 1535. The lateral branch lines 1585 may be oriented normal to the main feeder line 1583 as illustrated in FIG. 23, or may be oriented at angles to the main feeder line 1583.

The delivery of reduced pressure to the first plurality of flow channels 1541 and the delivery of the fluid to the second plurality of flow channels 1561 may be accomplished by separate tubes, such as reduced-pressure delivery tube 1551 and fluid delivery tube 1571. Alternatively, a tube having multiple lumens as described previously herein may be used to separate the communication paths for delivering the reduced pressure and the fluid. It should further be noted that while it is preferred to provide separate paths of fluid communication within the hip prosthesis 1515, the first plurality of flow channels 1541 could be used to deliver both the reduced pressure and the fluid to the bone surrounding the hip prosthesis 1515.

As previously described, application of reduced pressure to bone tissue promotes and speeds the growth of new bone tissue. By using the hip prosthesis 1515 as a manifold to deliver reduced pressure to the area of bone surrounding the hip prosthesis, recovery of the femur 1517 is faster, and the hip prosthesis 1515 integrates more successfully with the bone. Providing the second plurality of flow channels 1561 to vent the bone surrounding the hip prosthesis 1515 improves the successful generation of new bone around the prosthesis.

Following the application of reduced pressure through the hip prosthesis 1515 for a selected amount of time, the reduced-pressure delivery tube 1551 and fluid delivery tube 1571 may be disconnected from the connection ports 1545, 1565 and removed from the patient's body, preferably without a surgically-invasive procedure. The connection between the connection ports 1545, 1565 and the tubes 1551, 1571 may be a manually-releasable connection that is effectuated by applying an axially-oriented tensile force to the tubes 1551, 1571 on the outside of the patient's body. Alternatively, the connection ports 1545, 1565 may be bioresorbable or dissolvable in the presence of selected fluids or chemicals such that release of the tubes 1551, 1571 may be obtained by exposing the connection ports 1545, 1565 to the fluid or chemical. The tubes 1551, 1571 may also be made from a bioresorbable material that dissolves over a period of time or an activated material that dissolves in the presence of a particular chemical or other substance.

The reduced-pressure delivery source 1553 may be provided outside the patient's body and connected to the reduced-pressure delivery tube 1551 to deliver reduced pressure to the hip prosthesis 1515. Alternatively, the reduced-pressure delivery source 1553 may be implanted within the patient's body, either on-board or near the hip prosthesis 1515. Placement of the reduced-pressure delivery source 1553 within the patient's body eliminates the need for a percutaneous fluid connection. The implanted reduced-pressure delivery source 1553 may be a traditional pump that is operably connected to the flow channels 1541. The pump may be powered by a battery that is implanted within the patient, or may be powered by an external battery that is electrically and percutaneously connected to the pump. The pump may also be driven directly by a chemical reaction that delivers a reduced pressure and circulates fluids through the flow channels 1541, 1561.

While only the stem portion 1521 and head portion 1525 of the hip prosthesis 1515 are illustrated in FIGS. 22 and 23, it should be noted that the flow channels and means for applying reduced-pressure tissue treatment described herein could be applied to any component of the hip prosthesis 1515 that contacts bone or other tissue, including, for example, the acetabular cup.

Figure 24:
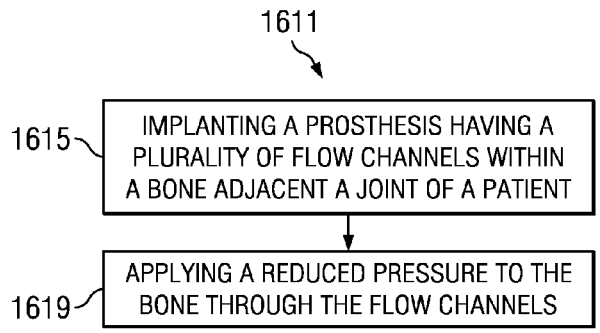
FIG. 24 depicts a flow chart of a method for repairing a joint of a patient using reduced-pressure tissue treatment according to an embodiment of the present invention.

Referring primarily to FIG. 24, a method 1611 for repairing a joint of a patient includes at 1615 implanting a prosthesis within a bone adjacent the joint. The prosthesis could be a hip prosthesis as described above or any other prosthesis that assists in restoring mobility to the joint of the patient. The prosthesis includes a plurality of flow channels configured to fluidly communicate with the bone. At 1619, a reduced pressure is applied to the bone through the plurality of flow channels to improve oseointegration of the prosthesis.

Figure 25:
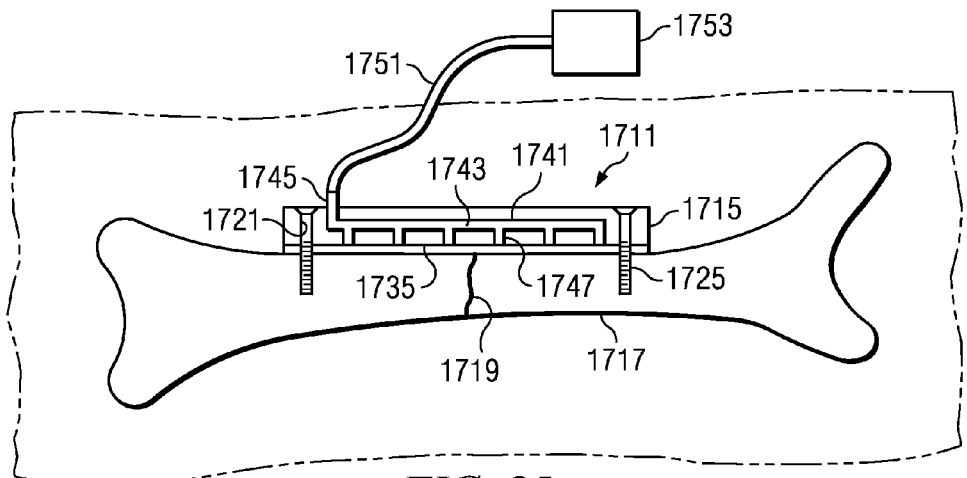
FIG. 25 illustrates a cross-sectional front view of a reduced-pressure delivery apparatus according to an embodiment of the present invention, the reduced-pressure delivery apparatus including a orthopedic fixation device having a plurality of flow channels for applying a reduced pressure to an area of bone adjacent the orthopedic fixation device.
Figure 26:
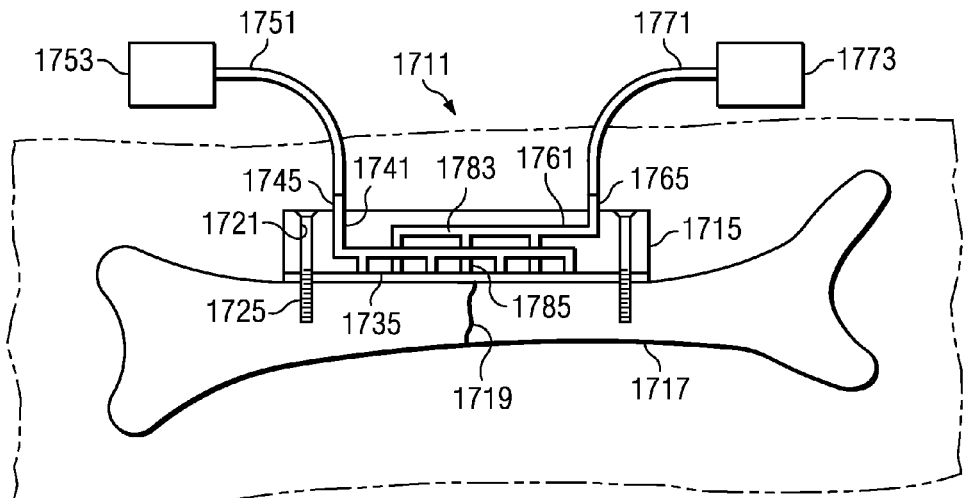
FIG. 26 depicts a cross-sectional front view of the orthopedic fixation device of FIG. 25 having a second plurality of flow channels for delivering a fluid to the area of bone adjacent the orthopedic fixation device.

Referring primarily to FIGS. 25 and 26, a reduced-pressure delivery apparatus 1711 according to an embodiment of the present disclosure includes an orthopedic fixation device 1715 for securing a bone 1717 of a patient that includes a fracture 1719 or other defect. The orthopedic fixation device 1715 illustrated in FIGS. 25 and 26 is a plate having a plurality of passages 1721 for anchoring the orthopedic fixation device 1715 to the bone 1717 with screws 1725, pins, bolts, or other fasteners. A porous coating 1735 may be disposed on a surface of the orthopedic fixation device 1715 that is to contact the bone 1717. The porous coating is preferably constructed from sintered or vitrified ceramics or metal. Alternatively, a cellular material having porous characteristic could be disposed between the bone 1717 and the orthopedic fixation device 1715. A plurality of flow channels 1741 is disposed within the orthopedic fixation device 1715 such that the flow channels 1741 are in fluid communication with the porous coating 1735. A connection port 1745 is fluidly connected to the flow channels 1741, the port being configured for connection to a reduced-pressure delivery tube 1751 and a reduced-pressure delivery source 1753. The flow channels 1741 are used to deliver a reduced pressure to the porous coating 1735 or the bone surrounding the orthopedic fixation device 1715 following fixation of the orthopedic fixation device 1715 to the bone 1717. The flow channels 1741 may include a main feeder line 1743 that fluidly communicates with several lateral branch lines 1747, which communicate with the porous coating 1735. The lateral branch lines 1747 may be oriented normal to the main feeder line 1743 as illustrated in FIG. 25, or may be oriented at angles to the main feeder line 1743. An alternative method for distributing the reduced pressure includes providing a hollow orthopedic fixation device, and filling the inner space of the orthopedic fixation device with a cellular (preferably open-cell) material that is capable of fluidly communicating with the porous coating 1735.

The orthopedic fixation device 1715 may be a plate as shown in FIG. 25, or alternatively may be a fixation device, such as a sleeve, a brace, a strut, or any other device that is used to stabilize a portion of the bone. The orthopedic fixation device 1715 may further be fasteners used to attach prosthetic or other orthopedic devices or implanted tissues (e.g., bone tissues or cartilage), provided that the fasteners include flow channels for delivering reduced pressure to tissue adjacent to or surrounding the fasteners. Examples of these fasteners may include pins, bolts, screws, or any other suitable fastener.

Referring more specifically to FIG. 26, the orthopedic fixation device 1715 may further include a second plurality of flow channels 1761 within the orthopedic fixation device 1715 to provide a fluid to the porous coating 1735 or the bone surrounding the orthopedic fixation device 1715. The fluid could include filtered air or other gases, antibacterial agents, antiviral agents, cell-growth promotion agents, irrigation fluids, chemically active agents, or any other fluid. If it is desired to introduce multiple fluids to the bone surrounding the orthopedic fixation device 1715, additional paths of fluid communication may be provided. A connection port 1765 is fluidly connected to the flow channels 1761, the connection port

1765 being configured for connection to a fluid delivery tube 1771 and a fluid delivery source 1773. The flow channels 1761 may include a main feeder line 1783 that fluidly communicates with several lateral branch lines 1785, which communicate with the porous coating 1735. The lateral branch lines 1785 may be oriented normal to the main feeder line 1783 as illustrated in FIG. 23, or may be oriented at angles to the main feeder line 1783.

The delivery of reduced pressure to the first plurality of flow channels 1741 and the delivery of the fluid to the second plurality of flow channels 1761 may be accomplished by separate tubes, such as reduced-pressure delivery tube 1751 and fluid delivery tube 1771. Alternatively, a tube having multiple lumens as described previously herein may be used to separate the communication paths for delivering the reduced pressure and the fluid. It should further be noted that while it is preferred to provide separate paths of fluid communication within the orthopedic fixation device 1715, the first plurality of flow channels 1741 could be used to deliver both the reduced pressure and the fluid to the bone adjacent the orthopedic fixation device 1715.

The use of orthopedic fixation device 1715 as a manifold to deliver reduced pressure to the area of bone adjacent the orthopedic fixation device 1715 speeds and improves recovery of the fracture 1719 of the bone 1717. Providing the second plurality of flow channels 1761 to communicate fluids to the bone surrounding the orthopedic fixation device 1715 improves the successful generation of new bone near the orthopedic fixation device.

Figure 27:
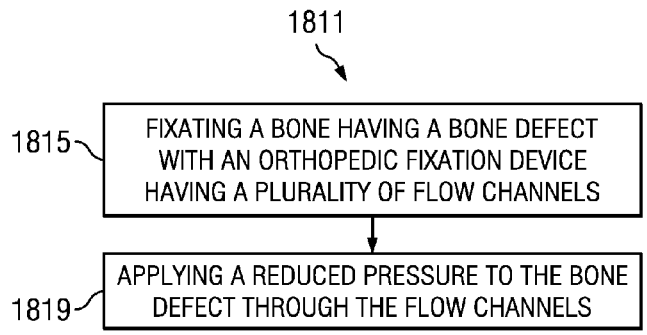
FIG. 27 illustrates a flow chart of a method for healing a bone defect of a bone using reduced-pressure tissue treatment according to an embodiment of the present invention.

Referring primarily to FIG. 27, a method 1811 for healing a bone defect of a bone includes at 1815 fixating the bone using an orthopedic fixation device. The orthopedic fixation device includes a plurality of flow channels disposed within the orthopedic fixation device. At 1819, a reduced pressure is applied to the bone defect through the plurality of flow channels.

Figure 28:
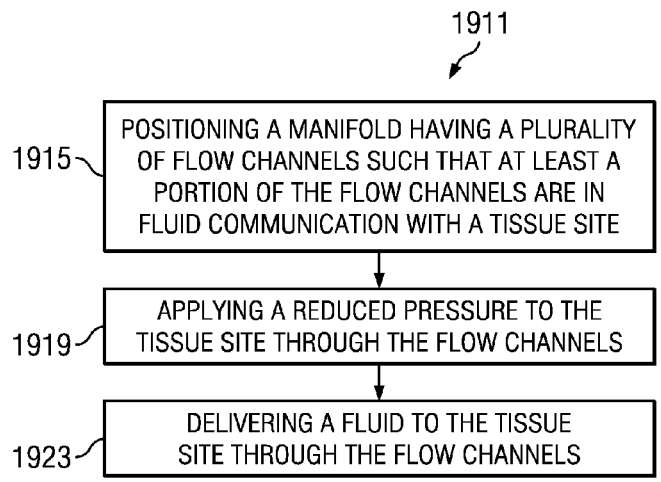
FIG. 28 depicts a flow chart of a method of administering a reduced-pressure tissue treatment to a tissue site according to an embodiment of the present invention.

Referring primarily to FIG. 28, a method 1911 for administering reduced-pressure tissue treatment to a tissue site includes at 1915 positioning a manifold having a plurality of flow channels such that at least a portion of the flow channels are in fluid communication with the tissue site. A reduced pressure is applied at 1919 to the tissue site through the flow channels, and a fluid is delivered at 1923 to the tissue site through the flow channels.

Figure 29:
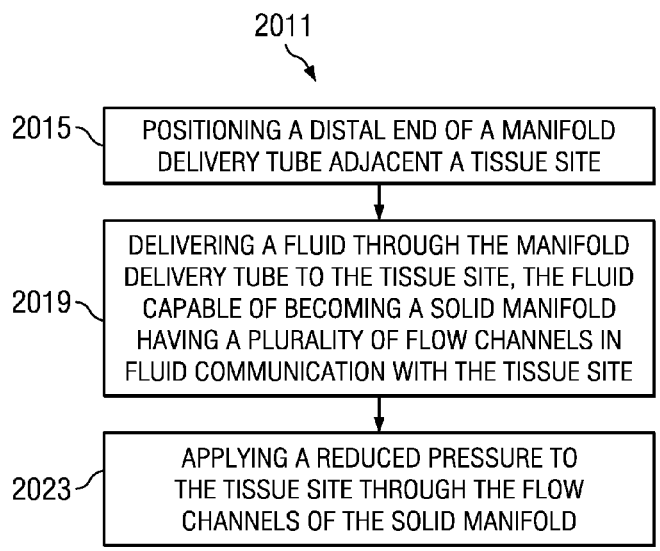
FIG. 29 illustrates a flow chart of a method of administering a reduced-pressure tissue treatment to a tissue site according to an embodiment of the present invention.

Referring primarily to FIG. 29, a method 2011 for administering reduced-pressure tissue treatment to a tissue site includes at 2015 positioning a distal end of a manifold delivery tube adjacent the tissue site. At 2019 a fluid is delivered through the manifold delivery tube to the tissue site. The fluid is capable of filling a void adjacent the tissue site and becoming a solid manifold having a plurality of flow channels in fluid communication with the tissue site. A reduced pressure is applied at 2023 to the tissue site through the flow channels of the solid manifold.

Referring primarily to FIGS. 30-38, a reduced-pressure delivery system 2111 includes a primary manifold 2115 having a wall 2117 surrounding a primary flow passage 2121. The wall 2117 is connected at a proximal end 2123 to a reduced-pressure delivery tube 2125. Since the shape of the reduced-pressure delivery tube 2125 will typically be round in cross-section, and since the shape of the primary manifold 2115 in cross-section may be other than round (i.e. rectangular in FIGS. 30-35 and triangular in FIGS. 36-38), a transition region 2129 is provided between the reduced-pressure delivery tube 2125 and the primary manifold 2115. The primary manifold 2115 may be adhesively connected to the reduced-pressure delivery tube 2125, connected using other means, such as fusing or insert molding, or alternatively may be integrally connected by co-extrusion. The reduced-pressure delivery tube 2125 delivers reduced pressure to the primary manifold 2115 for distribution at or near the tissue site.

The wall 2117 may be made from a flexible material, a rigid material, or a combination of both flexible and rigid materials. For example, a medical grade silicone polymer or other flexible materials may be molded, extruded, or otherwise manufactured to form a flexible wall 2117. Alternatively, rigid materials including but not limit to metals, polyvinylchloride (PVC), polyurethane, and other rigid polymeric materials may be molded, extruded, or otherwise manufactured to form a rigid wall 2117.

A blockage prevention member 2135 is positioned within the primary manifold to prevent collapse of the primary manifold 2115, and thus blockage of the primary flow passage 2121 during application of reduced pressure. In one embodiment, the blockage prevention member 2135 may be a plurality of projections 2137 (see FIG. 34) disposed on an inner surface 2141 of the wall 2117 and extending into the primary flow passage 2121. In another embodiment, the blockage prevention member 2135 may be a single or multiple ridges 2145 disposed on the inner surface 2141 (see FIGS. 30 and 31). In yet another embodiment, the blockage prevention member 2135 may include a cellular material 2149 disposed within the primary flow passage, such as that illustrated in FIG. 37. The blockage prevention member 2135 may be any material or structure that is capable of being inserted within the flow passage or that is capable of being integrally or otherwise attached to the wall 2117. When the wall 2117 is made from a flexible material, the blockage prevention member 2135 is able to prevent total collapse of the wall 2117, while still allowing the flow of fluids through the primary flow passage 2121.

The wall 2117 further includes a plurality of apertures 2155 through the wall 2117 that communicate with the primary flow passage 2121. The apertures 2155 allow reduced pressure delivered to the primary flow passage 2121 to be distributed to the tissue site. Apertures 2155 may be selectively positioned around the circumference of the primary manifold 2115 to preferentially direct the delivery of vacuum.

The reduced-pressure delivery tube 2125 preferably includes a first conduit 2161 having at least one outlet fluidly connected to the primary flow passage 2121 to deliver reduced pressure to the primary flow passage 2121. A second conduit 2163 may also be provided to purge the primary flow passage 2121 and the first conduit 2161 with a fluid to prevent or resolve blockages caused by wound exudate and other fluids drawn from the tissue site. The second conduit 2163 preferably includes at least one outlet positioned proximate to at least one of the primary flow passage 2121 and the at least one outlet of the first conduit 2161.

Figure 30:
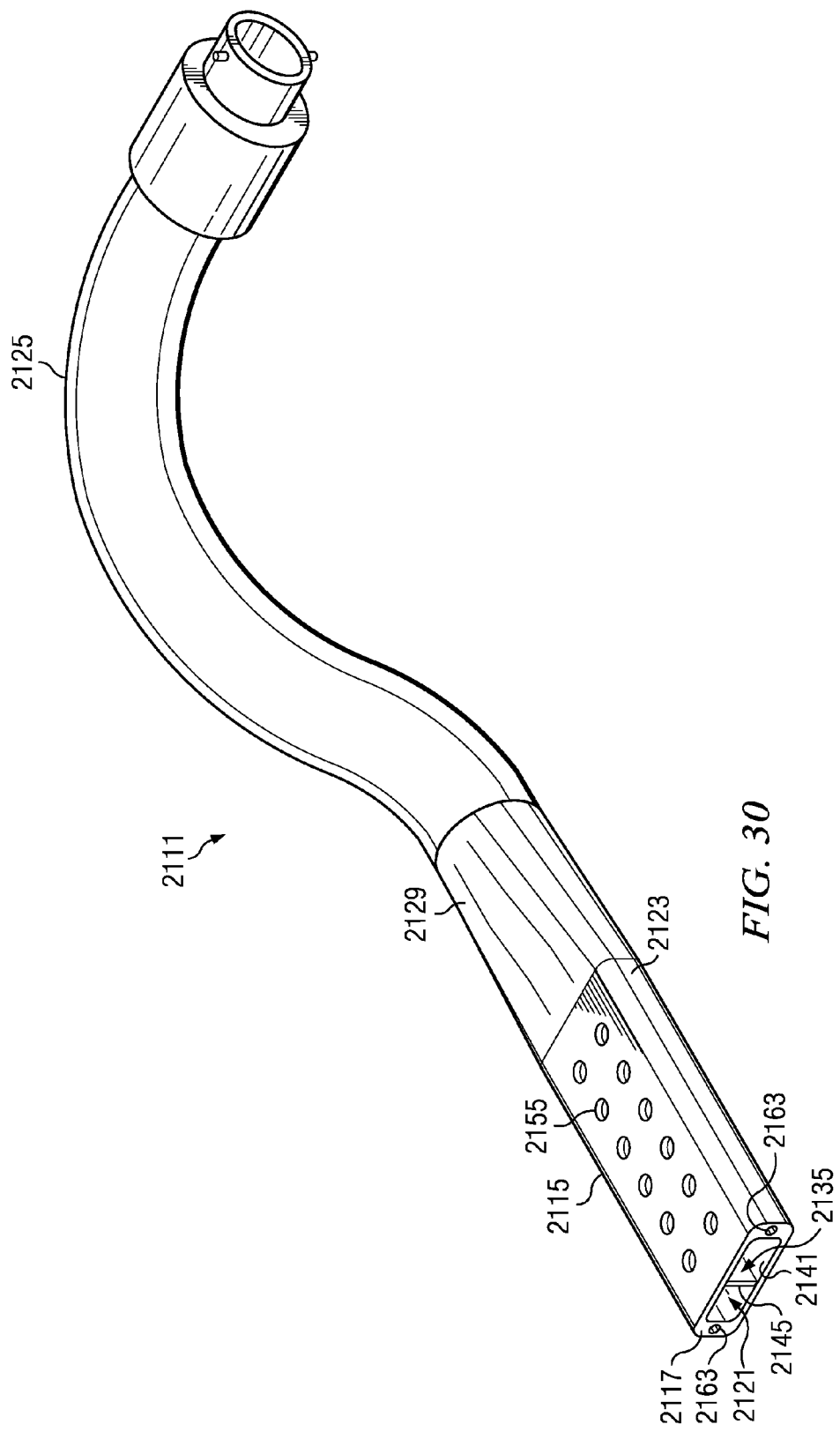
Figure 36:
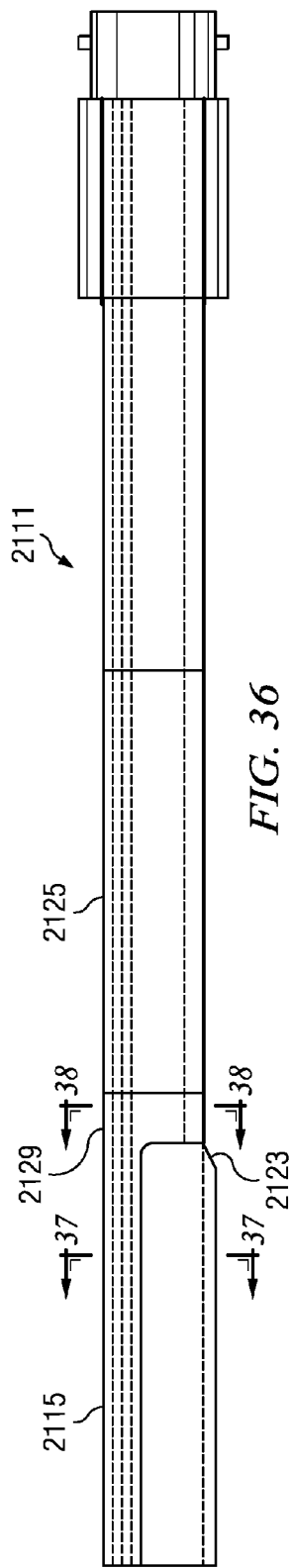
Figure 38:
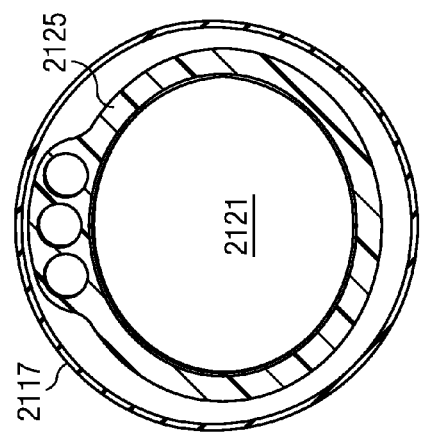
Figure 37:
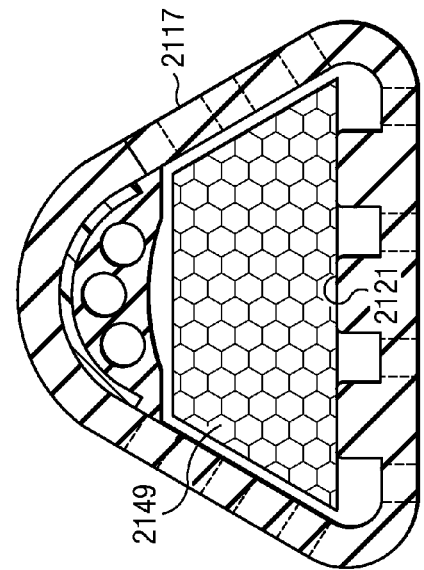

Referring more specifically to FIGS. 30 and 31, the reduced-pressure delivery system 2111 may include multiple conduits for purging the primary flow passage 2121 and the first conduit 2161. While the end of the wall 2117 opposite the end attached to reduced-pressure delivery tube 2125 may be open as illustrated in FIG. 30, it has been found that capping the end of the wall 2117 may improve the performance and reliability of the purging function. Preferably, a head space 2171 is provided for between the capped end of the wall and the end of the second conduit 2163. The head space 2171 allows for a buildup of purge fluid during the purging process, which helps drive the purge fluid through the primary flow passage 2121 and into the first conduit 2161.

Also illustrated in FIG. 31 is the divider that serves as the blockage prevention member 2135. The centrally-located divider bifurcates the primary flow passage 2121 into two chambers, which allows continued operation of the primary manifold 2115 if one of the chambers becomes blocked and purging is unable to resolve the blockage.

Figure 39:
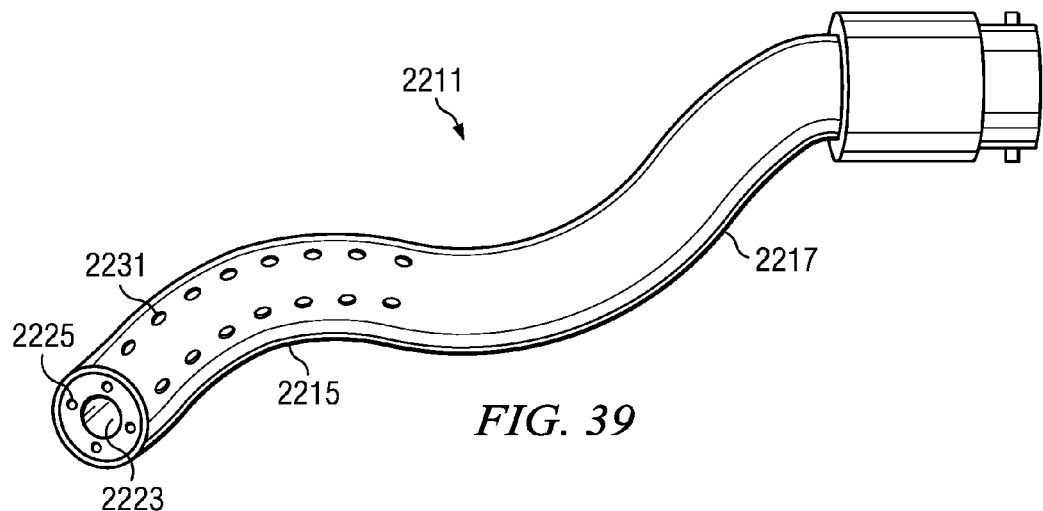
FIGS. 39-40 illustrate perspective and top cross-sectional views of a reduced-pressure delivery system according to an embodiment of the present invention, the reduced-pressure delivery system having a primary manifold that is integrally connected to a reduced-pressure delivery tube.
Figure 40:
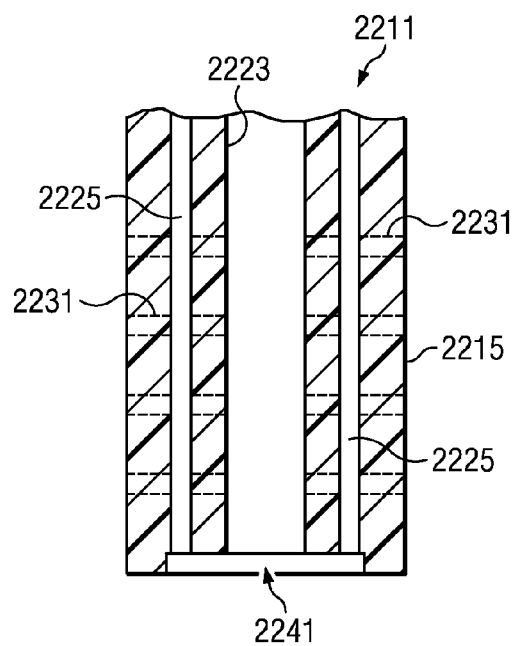

Referring primarily to FIGS. 39 and 40, a reduced-pressure delivery system 2211 includes a primary manifold 2215 that is integral to a reduced-pressure delivery tube 2217. The reduced-pressure delivery tube 2217 includes a central lumen 2223 and a plurality of ancillary lumens 2225. While the ancillary lumens 2225 may be used to measure pressure at or near the tissue site, the ancillary lumens 2225 may further be used to purge the central lumen 2223 to prevent or resolve blockages. A plurality of apertures 2231 communicate with the central lumen 2223 to distribute the reduced pressure delivered by the central lumen 2223. As illustrated in FIG. 40, it is preferred that the apertures 2231 not penetrate the ancillary lumens 2225. Also illustrated in FIG. 40 is the countersunk end of the reduced-pressure delivery tube, which creates a head space 2241 beyond the end of the ancillary lumens 2225. If tissue, scaffolds, or other materials were to engage the end of the reduced-pressure delivery tube 2217 during application of reduced pressure, the head space 2241 would continue to allow purging fluid, which may be a liquid or gas, to be delivered to the central lumen 2223.

In operation, the reduced-pressure delivery systems 2111, 2211 of FIGS. 30-40 may be applied directly to a tissue site for distributing reduced pressure to the tissue site. The low-profile shape of the primary manifolds is highly desirous for the percutaneous installation and removal techniques described herein. Similarly, the primary manifolds may also be inserted surgically.

Figure 41:
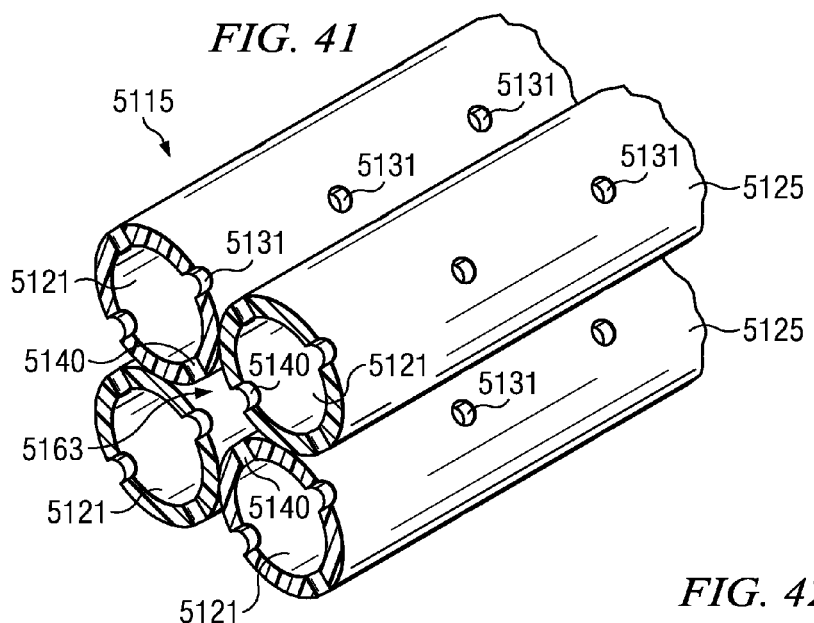
FIG. 41 is schematic, perspective view of a manifold according to an illustrative embodiment.
Figure 42:
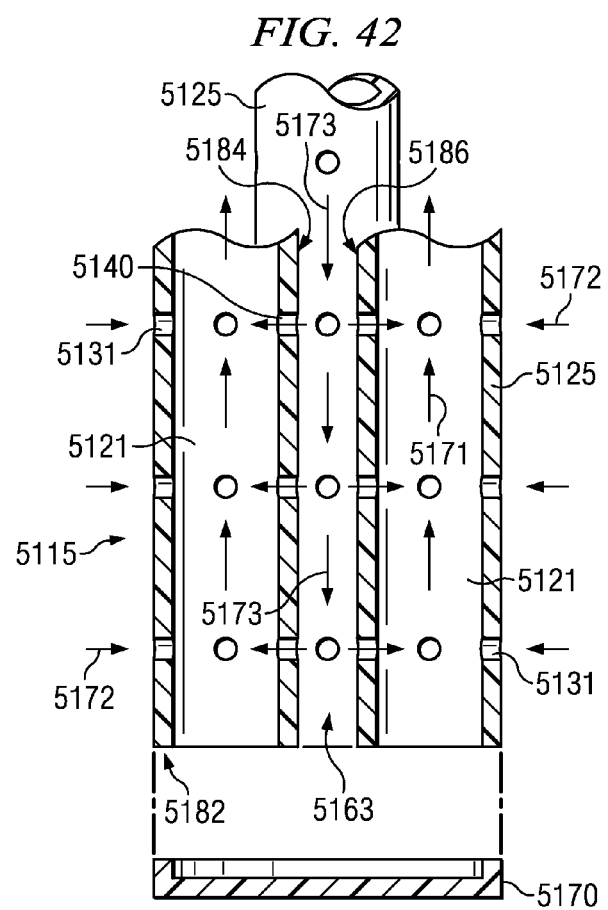
FIG. 42 is a schematic, longitudinal cross-sectional view of the manifold of FIG. 2.

Referring now primarily to FIGS. 41 and 42, a manifold 5115 is shown according to an illustrative embodiment. FIG. 42 is a longitudinal cross-sectional view of the manifold 5115. The manifold 5115 is adapted to be inserted into a patient and placed at the subcutaneous tissue site. The manifold 5115 includes a plurality of first conduits 5121 that are adjacent to one another to form an interior space that defines a second conduit 5163 between the first conduits 5121. The plurality of first conduits 5121 may be spaced in a uniform pattern or an irregular pattern and the members of the first plurality of conduits 5121 may be uniform in size or vary. The first conduits 5115 may be coupled one to another by a plurality of bonds, e.g., welds, cement, bonds, etc. The manifold 5115 provides a reduced-pressure supply function and purging function using the first conduits 5121 and second conduit 5163. In one non-limiting example, the second conduit 5163 may communicate with each of the first conduits 5121 via a plurality of second apertures 5140.

Figure 51:
FIG. 51 is a schematic plan view of an apparatus for applying reduced pressure to a subcutaneous tissue site according to an illustrative embodiment.

The manifold 5115 includes first conduits 5121. Each of the first conduits 5121 has at least one first aperture 5131 and at least one second aperture 5140 formed in a wall 5125, e.g., an annular wall. In the non-limiting examples of FIGS. 51 and 52, each of the first conduits 5121 has a plurality of first apertures 5131 and a plurality of second apertures 5140 formed in the wall 5125. The first apertures 5131 may be uniformly or non-uniformly spaced from one another and may be uniform or non-uniform in diameter. Also, the second apertures 5140 may be uniformly or non-uniformly spaced from one another and may be uniform or non-uniform in diameter.

In one illustrative embodiment, at least one of the first conduits 5121 is in fluid communication with a reduced-pressure source, such as the reduced-pressure source 427 in FIG. 9. At least one of the first conduits 5121 may deliver reduced pressure from the reduced-pressure source to a tissue site via the first apertures 5131. The first conduits 5121 may also deliver reduced pressure to any portion of the manifold 5115, such as a distal end 5182 of the manifold 5115. In another illustrative embodiment, each of the first conduits 5121 is in fluid communication with a reduced-pressure source, and each of first conduits 5121 delivers reduced pressure to a subcutaneous tissue site via the first apertures 5131. The flow of fluid in a direction away from the distal end 5182 of the manifold 5115 through the first conduits 5121 is represented by the arrows 5171. The flow of fluid away from the manifold 5115 in this manner causes a reduced pressure at the first conduits 5121 or at least a portion of the first conduits to be transferred to a tissue site via the first apertures 5131.

Each the first apertures 5131 allow fluid communication between the first conduits 5121 and a space outside of the manifold 5115, such as a tissue site. In addition to permitting the transfer of reduced pressure from the first conduits 5121 to a tissue site, the first apertures 5131 may also allow exudate or other fluid from the tissue site to enter the first conduits 5121. The flow of fluid from the space outside of the manifold 5115 into the first conduits 5121 is represented by arrows 5172.

The first conduits 5121 are shown with a circular cross-sectional shape. However, the first conduits 5121 may have any cross-sectional shape, including an elliptical, diamond, triangular, square, polygonal, etc.

In addition, although FIG. 41 shows the manifold 5115 having four first conduits 5121, the manifold 5115 may have any number of first conduits. For example, the manifold 5115 may have two or more first conduits 5121 that at least partially encompass and form the second conduit 5163. The second conduit 5163 may be centrally disposed between the two or more first conduits 5121 and typically between at least three of the first conduits 5121.

Each of the first apertures 5131 is shown to have a circular cross-sectional shape. However, each of the first apertures 5131 may have any cross-sectional shape, such as an elliptical or polygonal cross-sectional shape. In another example, each of the first apertures 5131 may be slits that extend along all or a portion of the first conduits 5121. As used herein, a "slit" is any elongated hole, aperture, or channel. In one illustrative embodiment, each of the slits may be substantially parallel to one another.

The second conduit 5163 of the manifold 5115 is formed by a portion of each of the outer surfaces 5184 and 5186 of the first conduits 5121. Each of the second apertures 5140 is located on the portion of each of the outer surfaces 5184 and 5186 of the first conduits 5121 that form the second conduit 5163. The second conduit 5163 is typically centrally formed, or otherwise disposed, between the first conduits 5121. The second conduit 5163 is in fluid communication with the first conduits 5121 via the second apertures 5140.

The second conduit 5163 may be in fluid communication with a fluid source (not shown) that supplies a fluid to the tissue site or portions of the first conduit 5121. The second conduit 5163 may receive fluid from the fluid source. In one embodiment, the second conduit 5163 delivers the fluid to each of the first conduits 5121 via the second apertures 5140. The second conduit 5163 may also deliver a fluid to a distal portion of the manifold 5115, including the end of the manifold 5115. The second conduit 5163 may also deliver a fluid to the tissue space around the manifold 5115. The fluid delivered by the second conduit 5163 may be a gas, such as air, or a liquid. The flow of fluid delivered by the second conduit 5163 is represented by arrows 5173. In an alternative embodiment, fluid from a fluid source may be delivered toward the distal end 5182 of the manifold 5115 by any one or more of the first conduits 5121.

In one non-limiting embodiment, the first conduits 5121 draw fluid from the second conduit 5163 via the second apertures 5140. In this embodiment, reduced pressure from a reduced-pressure source causes the fluid to be drawn from the second conduit 5163 to the first conduits 5121 via the second apertures 5140. In another non-limiting embodiment, positive pressure provided by the fluid source and delivered by the second conduit 5163 forces, or otherwise causes, the fluid to be transferred from the second conduit 5163 to the first conduits 5121 via the second apertures 5140. The transfer of fluid from the second conduit 5163 to the first conduits 5121 via the second apertures 5140 facilitates the purging function of the manifold 5115 that helps to remove or reduce any blockages that form in the manifold 5115. The first conduits 5121 may include any number of second apertures 5140, which number may control the rate of fluid being transferred from the second conduit 5163 to the first conduits 5121.

In one embodiment, the manifold 5115 may also include an end cap 5170 that is adapted to be coupled or is coupled to the distal end 5182 of the manifold 5115 to form a distribution space. Fluid delivered by the second conduit 5163 may be transferred from the second conduit 5163 to the first conduits 5121 via the space that is formed by coupling the end cap 5170 to the distal end 5182 of the manifold 5115. In one embodiment, the space may provide the sole passageway through which fluid is transferred from the second conduit 5163 to the first conduits 5121. In this embodiment, no second apertures 5140 may be present on the first conduits 5121 or a minimal number of apertures 5140.

In one illustrative embodiment, the second apertures 5140 are absent or not open to the outside of the manifold 5115 and fluid, such as liquid or air, may be drawn into the second conduit 5163 by opening a valve to atmosphere (e.g., air purge). The valve is in fluid communication with the second conduit 5163. Thus, fluid may be drawn through the second conduit 5163 and back toward a reduced-pressure device via the first conduits 5121, which, while under reduced pressure, may supply the force to draw any clot/clog formations, such as fibrin formations, out of the manifold 5115 and toward the reduced-pressure source. In this embodiment, no supply port for the second conduit 5163 may be present on the outer surface of the manifold 5115. In this illustrative embodiment, the second conduit 5163 may be completely enclosed by the first conduits 5121, including a distal end of the second conduit 5163, and thus may be closed from an outside environment, such as a tissue space. The second conduit 5163 communicates proximate end cap 5170 from the second conduit 5163 to the first conduits 5121. This illustrative embodiment may allow for a fluid to be contained within the manifold 5115 as the fluid moves from the second conduit 5163 to the first conduits 5121. Thus, in this embodiment, the likelihood of the fluid moving out into the tissue space is reduced or eliminated.

In one illustrative, non-limiting embodiment, the manifold 5115 is formed with four of the first conduits 5121. As before, the first conduits 5121 form the second conduit 5163. Each of the four first conduits 5121 touch at least two other of the four first conduits 5121. In this embodiment, the four first conduits 5121 and second conduit 5163 are formed by co-extruding the conduits 5121, 5163. After the extruding the conduits 5121, 5163, a core pin may be used to pierce the conduits straight through to form the first apertures 5131. Thus, for example, a core pin may pierce the upper right (for the orientation in FIG. 41) first conduit 5121 and the lower left first conduit 5121—and concomitantly pierce the second conduit 5163. This may be repeated as many times as desired and at various orientations.

In the example in which the fluid in second conduit 5163 is a liquid, the liquid may be pumped in or gravity fed down the second conduit 5163 such that the only pathway for the liquid is through the second apertures 5140 and into the first conduits 5121, along the first conduits 5121, and toward the reduced-pressure source. The manifold 5115 preferably has a symmetrical design, and the symmetrical design of the manifold 5115 allows the manifold 5115 to be used in any spatial orientation to achieve the same or similar results in each position.

In another illustrative embodiment, a supplied fluid may be allowed to enter the space surrounding the manifold 5115, such as a tissue space. For example, the fluid may exit the manifold 5115 at the opening at the distal end 5182 of the second conduit 5163. The fluid may then be drawn into the first conduits 5121.

In one illustrative embodiment, a method for applying reduced pressure to a subcutaneous tissue site includes applying the manifold 5115 to the subcutaneous tissue site. The manifold 5115 may be percutaneously inserted into a patient, and the manifold 5115 may be positioned adjacent to or abutting the subcutaneous tissue site. The symmetrical design of the manifold 5115 may facilitate the implantation of the manifold in any orientation.

In one illustrative embodiment, a method of manufacturing an apparatus for applying reduced pressure to a subcutaneous tissue site includes providing first conduits 5121. The method may also include coupling the first conduits 5121 to one another to form the second conduit 5163. The second conduit 5163 is formed by a portion of each outer surface 5184 and 5186 of the first conduits 5121. The method may also include providing a delivery conduit for delivering reduced pressure to at least one of the first conduits 5121. The method may also include fluidly coupling the delivery conduit to the first conduits 5121 and the second conduit 5163.

Figure 43:
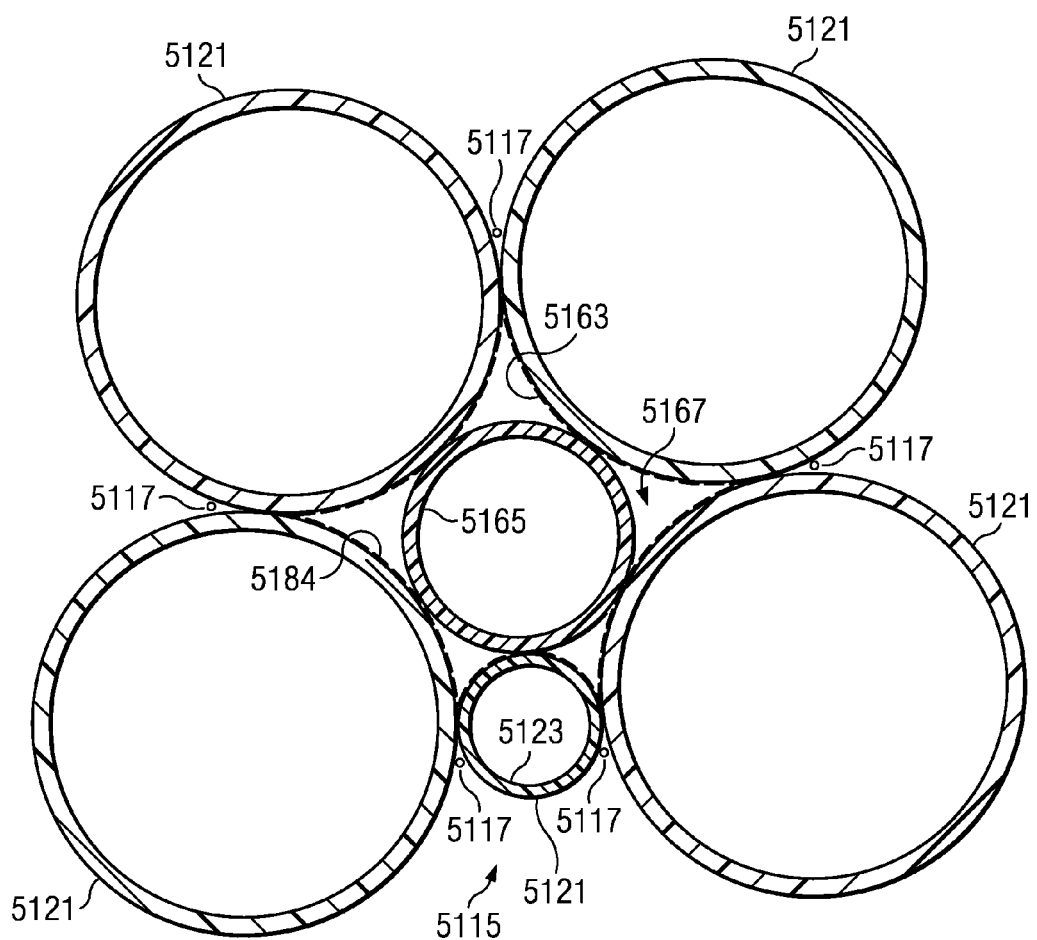
FIG. 43 is a schematic, lateral cross-sectional view of a manifold according to another illustrative embodiment.

Referring now primarily to FIG. 43, another illustrative, non-limiting embodiment of the manifold 5115 is presented. The manifold 5115 includes the plurality of first conduits 5121 that are coupled in a spaced relationship with a plurality of bonds 5117. Each of the plurality of first conduits 5121 may have differing diameters or the same diameters, and in this illustrative embodiment, one conduit 5123 of the first conduits conduit 5121 is shown with a smaller diameter than the others. It should be understood in this and the other illustrative embodiments that the diameter of the first conduits may be varied or may be uniform.

The manifold 5115 includes the second conduit 5163 formed by a portion of each of the outer surfaces 5184 of the first conduits 5121. The second conduit 5163 is shown with broken lines and in this illustration is a star-like shape. One or more additional conduits, such as third conduit 5165, may be disposed within the second conduit 5163. The additional conduit 5165 may be sized to touch each of the plurality of first conduits 5121 as shown or may be smaller in size. The additional conduit, or third conduit 5165, may be coupled to one or more of the fist conduits 5121. In an alternative embodiment (not shown), the first conduits 5121 may not form or fully form the second conduit, but the manifold 5115 may have the additional conduit 5165 at a center position adjacent to each of the first conduits 5121.

The additional conduit 5165 may carry a purging fluid or may be used to carry other fluids to or from a distal end (not shown) of the manifold 5115. The space 5167 formed exterior to the additional conduit 5165 and on the interior of the second conduit 5163 may carry a purging fluid to be introduced through apertures in the outer wall portion 5184 of the first conduits 5121, and the additional conduit 5165 may carry a purging fluid to an end cap (e.g., end cap 5170 in FIG. 42) to introduce a purging fluid into the first conduits 5121 at the distal end. The end cap 5170 may be attached to the distal end 5182 using interference fit, RF welding, RF formed tip process, solvent bonding, or any other coupling technique.

Figure 44A:
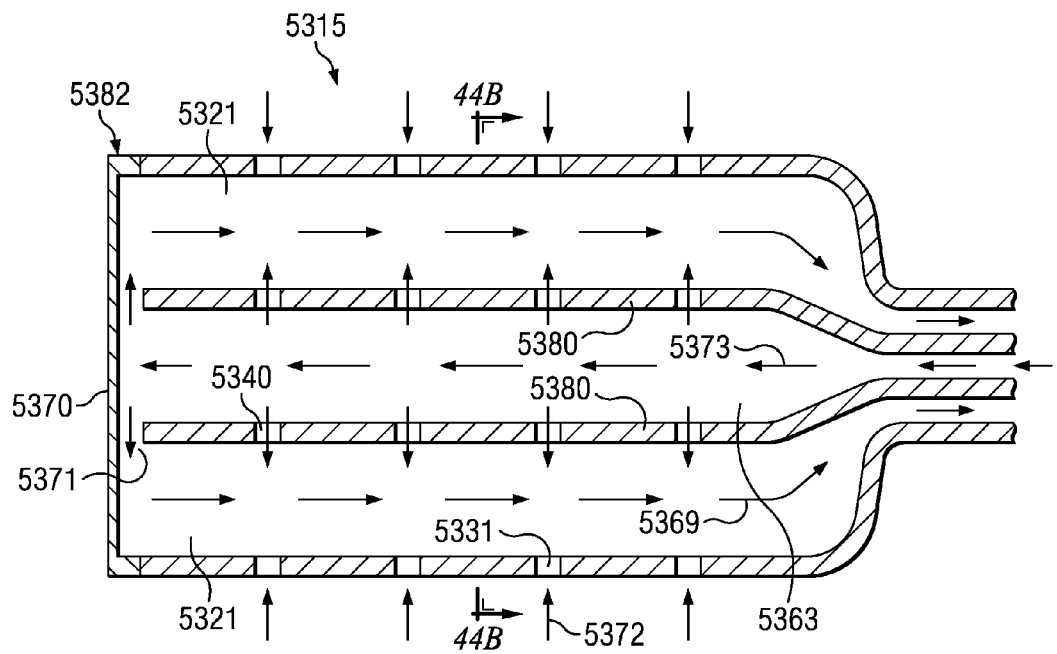
FIG. 44A is a schematic longitudinal cross-sectional view of a manifold according to an illustrative embodiment.
Figure 44B:
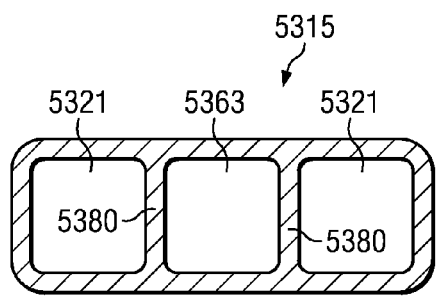
FIG. 44B is a schematic, lateral cross-sectional view of the manifold of FIG. 44A.

Referring primarily to FIGS. 44A and 44B, a manifold 5315 is shown according to an illustrative embodiment. The manifold 5315 includes purging lumen 5363 and reduced-pressure lumens 5321 that are at least partially separated by lumen walls 5380. In one non-limiting example, the purging lumen 5363 may communicate with each of the reduced-pressure lumens 5321 via the interlumen channels 5340 and head space 5371.

The manifold 5315 includes reduced-pressure lumens 5321 to transfer reduced pressure from a reduced-pressure source. The reduced-pressure lumens 5321 deliver reduced pressure from a reduced-pressure source to a tissue site, or any portion of the manifold 5315. The flow of fluid in a direction away from the end 5382 of the manifold 5315 through the reduced-pressure lumens 5321 is represented by the arrows 5369. The flow of fluid away from the manifold 5315 in this manner causes a reduced pressure at the reduced-pressure lumens 5321 that may be transferred to a tissue site, as well as other portions of the manifold 5315. The reduced-pressure lumens 5321 may have any cross-sectional shape, including a circular, elliptical, flattened, irregular, or polygonal cross-sectional shape. In one example, the material from which the manifold 5315 is made may be flexible, causing the cross-sectional shape of the reduced-pressure lumens 5321 to vary depending on fluid flow through the lumens. In addition, although FIGS. 44A and 44B show the manifold 5315 to have two reduced-pressure lumens 5321, the manifold 5315 may have any number of reduced-pressure lumens depending on the particular implementation.

The reduced-pressure lumens 5321 also include apertures 5331. Reduced pressure from a reduced-pressure source may be delivered to a tissue site via the apertures 5331 of the reduced-pressure lumens 5321. Each of the apertures 5331 allows fluid communication between the reduced-pressure lumens 5321 and a space outside of the manifold 5315, such as a tissue site. In addition to permitting the transfer of reduced pressure from the reduced-pressure lumens 5321 to a tissue site, the apertures 5331 may also allow exudate or other fluid from the tissue site to enter the reduced-pressure lumens 5321. The flow of fluid from the space outside of the manifold 5315 into the reduced-pressure lumens 5321 is represented by arrows 5372.

Each of the apertures 5331 may have a circular cross-sectional shape. However, each of the apertures 5331 may have any cross-sectional shape, such as an elliptical, polygonal, irregular cross-sectional shape. In another example, each of the apertures 5331 may be slits that extend along all or a portion of the reduced-pressure lumens 5321. In this example, each of the slits may be substantially parallel to one another.

The manifold 5315 also includes purging lumen 5363. The purging lumen 5363 is centrally disposed between the reduced-pressure lumens 5321. The purging lumen 5363, which is another non-limiting embodiment of the second conduit 2163 in FIGS. 30 and 31, is operable to deliver a fluid to a distal portion of the manifold 5315, including the end 5382 of the manifold 5315. The purging lumen 5363 may also deliver a fluid to the tissue space around the manifold 5315. The fluid delivered by the purging lumen 5363 may be a gas, such as air, or a liquid. The flow of fluid delivered by the purging lumen 5363 is represented by arrows 5373.

The purging lumen 5363 may have any cross-sectional shape, including an circular, elliptical, flattened, irregular, or polygonal cross-sectional shape. In one example, the material from which the manifold 5315 is made may be flexible, causing the cross-sectional shape of the purging lumen 5363 to vary depending on fluid flow through the lumen, as well as other factors. Although one purging lumen 5363 is shown, the manifold 5315 may include any number of purging lumens.

The purging lumen 5363 is separated from the reduced-pressure lumens 5321 by lumens walls 5380, which may be flexible or rigid. The lumens walls 5380 include interlumen channels 5340. The interlumen channels 5340 fluidly connect, or otherwise provide fluid communication between, the purging lumen 5363 and the reduced-pressure lumens 5321. In one example, the reduced-pressure lumens 5321 draw purging fluid from the purging lumen 5363 via the interlumen channels 5340. In another example, positive pressure in the purging lumen 5363 forces the fluid from the purging lumen 5363 to the reduced-pressure lumens 5321 via the interlumen channels 5340. The positive pressure in the purging lumen 5363 may be supplied by a positive pressure source. The lumen walls 5380 may include any number of interlumen channels 5340, which number may control the rate of fluid being transferred from the purging lumen 5363 to the reduced-pressure lumens 5321.

In another example, the transfer of fluid from the purging lumen 5363 to the reduced-pressure lumen 5321 may occur via the head space 5371 that is formed by coupling an end of the manifold 5315 to the end cap 5370. In one embodiment, the head space may provide the sole passageway through which fluid is transferred from the purging lumen 5363 to the reduced-pressure lumens 5321. In this embodiment, no interlumen channels 5340 may be present in the manifold 5315. To facilitate the transfer of fluid from the purging lumen 5363 to the reduced-pressure lumens 5321, the lumens walls 5380 may terminate without touching the end cap 5370 to form the head space 5371.

Figure 45:
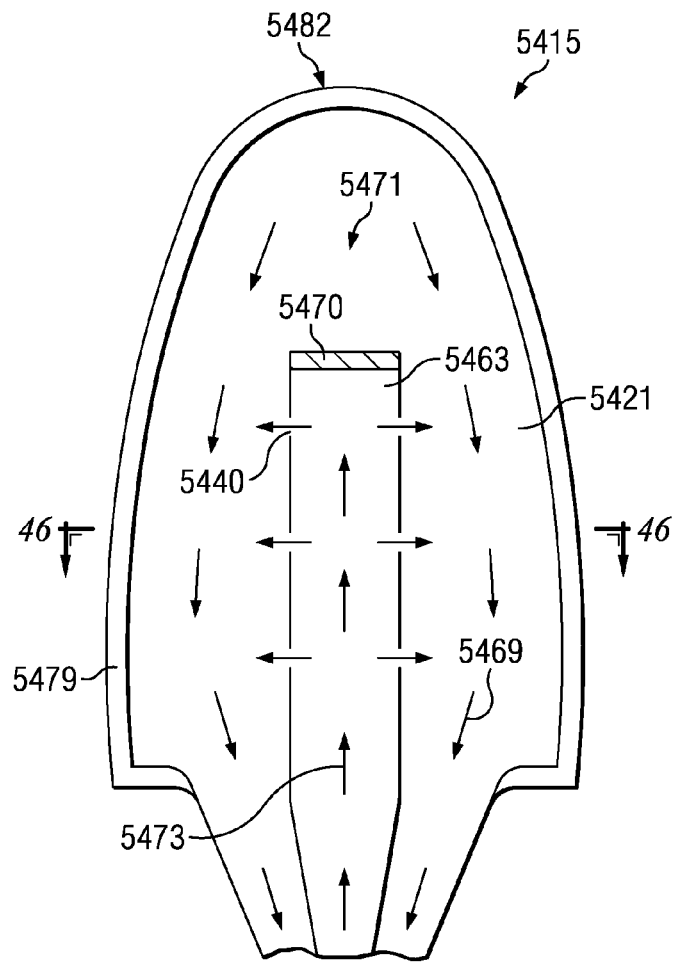
FIG. 45 is a schematic cross-sectional view of a manifold according to an illustrative embodiment.
Figure 46:
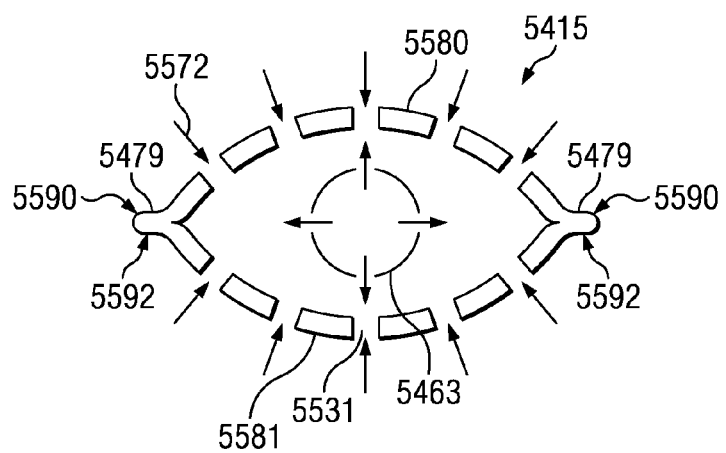
FIG. 46 is a schematic cross-sectional view of a manifold according to an illustrative embodiment.

Referring primarily to FIGS. 45 and 46, a manifold 5415 is shown according to an illustrative embodiment. FIG. 46 is a cross-sectional view of manifold 5415 taken along line 46-46 in FIG. 45. The manifold 5415 includes sheets 5580 and 5581. A perimeter 5590 of the sheet 5580 is attached to a perimeter 5592 of the sheet 5581 to form a pouch. The manifold 5415 also includes a reduced-pressure cavity 5421 that is at least partially enclosed by the pouch. The purging tube 5463 extends into the pouch.

The sheets 5580 and 5581 may be made from any material, and may be rigid or flexible. In one example, the sheets 5580 and 5581 are composed of silicone. The low-profile, and potentially flexible, nature of the manifold 5415 facilitates the movement and placement of the manifold 5415 at a subcutaneous tissue site. The low profile of the manifold 5415 may also ease percutaneous removal of the manifold 5415. The pouch that is formed from the coupling between the sheets 5580 and 5581 is shown in FIG. 45 to have a "U" shape. The cross-sectional view of FIG. 46 shows the sheets 5580 and 5581 to have an oval or "eye" shape. However, the pouch may also have any shape depending on the implementation, such as a circular, polygonal, or irregular shape. In one example, the material from which the pouch is made may be flexible, causing the cross-sectional shape of the pouch, and therefore the reduced-pressure cavity 5421, to vary depending on fluid flow through the cavity, as well as other factors.

In one example, a perimeter 5590 of the sheet 5580 is fixedly attached to a perimeter 5592 of the sheet 5581 to form seams 5479. Alternatively, no seams may be present as a result of the coupling between the sheets 5580 and 5581. In another example, the sheets 5580 and 5581 are not separate sheets, but are formed from a single continuous piece of material.

The reduced-pressure cavity 5421 transfers reduced pressure from a reduced-pressure source. The reduced-pressure cavity 5421 may deliver reduced pressure from a reduced-pressure source to a tissue site, or any portion of the manifold 5415. The flow of fluid away from the end 5482 of manifold 5415 through the reduced-pressure cavity 5421 is represented by the arrows 5469. The flow of fluid away from the manifold 5415 in this manner causes a reduced pressure at the reduced-pressure cavity 5421 that may be transferred to a tissue site, as well as other portions of the manifold 5415.

The sheets 5580 and 5581 include apertures 5531. Reduced pressure from a reduced-pressure source may be delivered to a tissue site via the apertures 5531. Each the apertures 5531 allow fluid communication between the reduced-pressure cavity 5421 and a space outside of the manifold 5415, such as a tissue site. In addition to permitting the transfer of reduced pressure from the reduced-pressure cavity 5421 to a tissue site, the apertures 5531 may also allow exudate or other fluid from the tissue site to enter the reduced-pressure cavity 5421. The flow of fluid from the space outside of the manifold 5415 into the reduced-pressure cavity 5421 is represented by arrows 5572.

Each of the apertures 5531 may have a circular cross-sectional shape. However, each of the apertures 5531 may have any cross-sectional shape, such as an elliptical, polygonal, irregular cross-sectional shape. In another example, each of the apertures 5531 may be slits that extend along all or a portion of the sheets 5580 and 5581. In this example, each of the slits may be substantially parallel to one another. Although the apertures 5531 are shown to be included on both the sheets 5580 and 5581, the apertures 5531 may also be included on only one of the sheets 5580 and 5581.

The purging tube 5463 is disposed within the pouch formed by the sheets 5580 and 5581. The purging tube 5463, which is another non-limiting embodiment of the second conduit 2163 in FIGS. 30 and 31, is operable to deliver a fluid to a distal portion of the manifold 5415, including the end 5482 of the manifold 5415. The purging tube 5463 may also deliver a fluid to the tissue space around the manifold 5415. The fluid delivered by the purging lumen 5463 may be a gas, such as air, or a liquid. The flow of fluid delivered by the purging lumen 5463 is represented by arrows 5473.

The purging tube 5463 may have any cross-sectional shape, including an circular, elliptical, flattened, irregular, or polygonal cross-sectional shape. In one example, the material from which the purging tube 5463 is made may be flexible, causing the cross-sectional shape of the purging tube 5463 to vary depending on fluid flow through the tube, as well as other factors. Although one purging tube 5463 is shown, the manifold 5415 may include any number of purging lumens.

The purging tube 5463 includes interlumen channels 5440. The interlumen channels 5440 fluidly connect, or otherwise provide fluid communication between, the purging tube 5463 and the reduced-pressure cavity 5421. In one example, the reduced-pressure cavity 5421 draws purging fluid from the purging tube 5463 via the interlumen channels 5440. In another example, positive pressure in the purging tube 5463 forces the fluid from the purging tube 5463 to the reduced-pressure cavity 5421 via the interlumen channels 5440. The positive pressure in the purging tube 5463 may be supplied by a positive pressure source. The purging tube 5463 may include any number of interlumen channels 5440, which number may control the rate of fluid being transferred from the purging tube 5463 to the reduced-pressure cavity 5421.

In another example, the transfer of fluid from the purging tube 5463 to the reduced-pressure cavity 5421 may occur via the head space 5471. In this example, no end cap, such as the end cap 5470, may be placed on an end of the purging tube 5463 so that the fluid from the purging tube 5463 may enter the head space 5471. In one embodiment, the head space may provide the sole passageway through which fluid is transferred from the purging tube 5463 to the reduced-pressure cavity 5421. In this embodiment, no interlumen channels 5440 may be present in the manifold 5415 and no end cap may be placed on an end of the purging tube 5463. In another example, the end cap 5470 may be placed on an end of the purging tube 5463 so that the interlumen channels 5440 provide the sole passageways through which fluid is transferred from the purging tube 5463 to the reduced-pressure cavity 5421.

Figure 47:
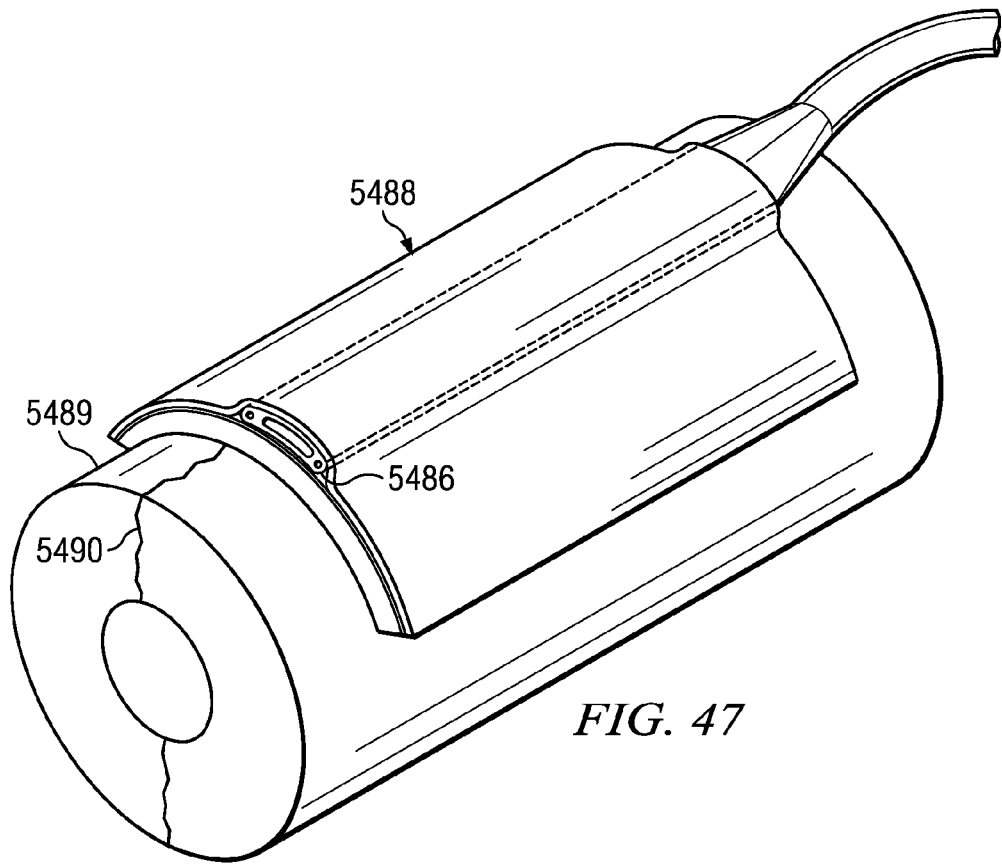
FIG. 47 depicts a perspective view of the primary manifolds of FIGS. 30-40 being applied with a secondary manifold to a bone tissue site.

Referring primarily to FIG. 47, a primary manifolds 5486, which may any manifold disclosed herein, may be used in conjunction with a secondary manifold 5488. In FIG. 47, the secondary manifold 5488 includes a two-layered felted mat. The first layer of the secondary manifold 5488 is placed in contact with a bone tissue site 5489 that includes a bone fracture 5490 or other defect. The primary manifold 5486 is placed in contact with the first layer, and the second layer of the secondary manifold 5488 is placed on top of the primary manifold 5486 and first layer. The secondary manifold 5488 facilitates fluid communication between the primary manifold 5486 and the bone tissue site 5489, yet prevents direct contact between the bone tissue site 5489 and the primary manifold 5486.

Preferably, the secondary manifold 5488 is bioabsorbable, which allows the secondary manifold 5488 to remain in situ following completion of reduced-pressure treatment. Upon completion of reduced-pressure treatment, the primary manifold 5486 may be removed from between the layers of the secondary manifold 5488 with little or no disturbance to the bone tissue site 5489. In one embodiment, the primary manifold 5486 may be coated with a lubricious material or a hydrogel-forming material to ease removal from between the layers.

The secondary manifold 5488 preferably serves as a scaffold for new tissue growth. As a scaffold, the secondary manifold 5488 may be comprised of at least one material selected from the group of polylactic acid, polyglycolic acid, polycaprolactone, polyhydroxybutyrate, polyhydroxyvalerate, polydioxanone, polyorthoesthers, polyphosphazenes, polyurethanes, collagen, hyaluronic acid, chitosan, hydroxyapatite, calcium phosphate, calcium sulfate, calcium carbonate, bioglass, stainless steel, titanium, tantalum, allografts, and autografts.

The purging function of the reduced-pressure delivery systems in FIGS. 30-32, 36, 39, and 40 may be employed with any of the manifolds described herein. The ability to purge a manifold or a conduit delivering reduced pressure prevents blockages from forming that hinder the administration of reduced pressure. These blockages typically form as the pressure near the tissue site reaches equilibrium and egress of fluids around the tissue site slows. It has been found that purging the manifold and reduced-pressure conduit with air for a selected amount of time at a selected interval assists in preventing or resolving blockages. For example, purging the manifold may prevent blockages caused by fibrin.

More specifically, air is delivered through a second conduit separate from a first conduit that delivers reduced pressure. An outlet of the second conduit is preferably proximate to the manifold or an outlet of the first conduit. While the air may be pressurized and "pushed" to the outlet of the second conduit, the air is preferably drawn through the second conduit by the reduced pressure at the tissue site. It has been found that delivery of air for two (2) seconds at intervals of sixty (60) seconds during the application of reduced pressure is sufficient to prevent blockages from forming in many instances. This purging schedule provides enough air to sufficiently move fluids within the manifold and first conduit, while preventing the introduction of too much air. Introducing too much air, or introducing air at too high of an interval frequency will result in the reduced-pressure system not being able to return to the target reduced pressure between purge cycles. The selected amount of time for delivering a purging fluid and the selected interval at which the purging fluid is delivered will typically vary based on the design and size of system components (e.g., the pump, tubing, etc.). However, purging fluid, such as air, should be delivered in a quantity and at a frequency that is high enough to sufficiently clear blockages while allowing the full target pressure to recover between purging cycles.

Figure 48:
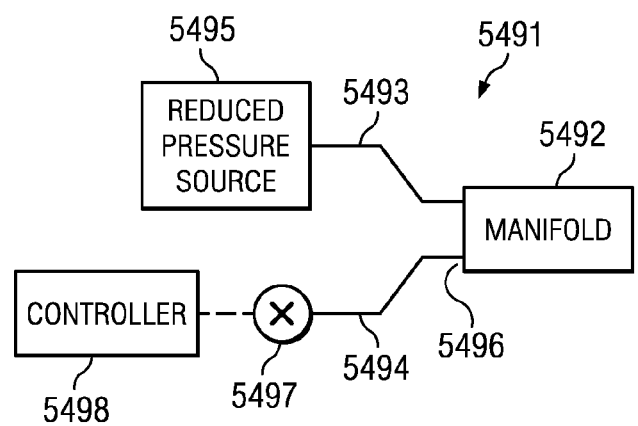
FIG. 48 illustrates a schematic view of a reduced-pressure delivery system having a valve fluidly connected to a second conduit according to an embodiment of the present invention.

Referring primarily to FIG. 48, in one illustrative embodiment, a reduced-pressure delivery system 5491 includes a manifold 5492 fluidly connected to a first conduit 5493 and a second conduit 5494. The first conduit 5493 is connected to a reduced-pressure source 5495 to provide reduced pressure to the manifold 5492. The second conduit 5494 includes an outlet 5496 positioned in fluid communication with the manifold 5492 and proximate an outlet of the first conduit 5493. The second conduit 5494 is fluidly connected to a valve 5497, which is capable of allowing communication between the second conduit 5494 and the ambient air when the valve 5497 is placed in an open position. The valve 5497 is operably connected to a controller 5498 that is capable of controlling the opening and closing of the valve 5497 to regulate purging of the second conduit with ambient air to prevent blockages within the manifold 5492 and the first conduit 5493.

It should be noted that any fluid, including liquids or gases, could be used to accomplish the purging techniques described herein. While the driving force for the purging fluid is preferably the draw of reduced pressure at the tissue site, the fluid similarly could be delivered by a fluid delivery means similar to that discussed with reference to FIG. 9.

Referring primarily to FIGS. 49-52, a reduced-pressure delivery apparatus 5800 is shown according to an illustrative embodiment. The reduced-pressure treatment apparatus 5800 includes a manifold 5815, a transition region 5829, and a delivery tube 5825. The reduced-pressure treatment apparatus 5800 delivers reduced pressure from a reduced-pressure source, such as reduced-pressure source 5495 in FIG. 48, to a subcutaneous tissue site through slits 5831. The reduced-pressure treatment apparatus 5800 also includes a purging function that helps to prevent blockages from forming in the manifold 5815.

Although not shown in FIGS. 49-52, the manifold 5815 may include at least one purging lumen operable to deliver a fluid, such as a gas or liquid, to a distal portion of the manifold 5815. The manifold 5815 may also include at least one reduced-pressure lumen operable to deliver reduced pressure to a subcutaneous tissue site via the slits 5831. The at least one reduced-pressure lumen may terminate at the slits 5831, which provide an opening though which reduced pressure may be applied to a subcutaneous tissue site. In addition, the manifold 5815 may include one or more interlumen channels that fluidly interconnect any combination of the at least one reduced-pressure lumen, the at least one purging lumen, and the slits 5831. In one embodiment, the slits 5831 are parallel to the at least one reduced-pressure lumen (not shown) and the at least one purging lumen (not shown). The at least one purging lumen, reduced-pressure lumen, and interlumen channel are shown in further detail in FIGS. 53-55.

The manifold 5815 is adapted to be inserted for placement at a subcutaneous tissue site. In the embodiment of FIGS. 49-52, the manifold 5815 has an flattened shape to facilitate the positioning of the manifold 5815 at a subcutaneous tissue site. In particular, the manifold 5815 has flat side 5885 and opposing flat side 5886, as well as curved side 5887 and opposing curved side 5888. In other examples, each of flat sides 5885 and 5886 and curved sides 5887 and 5888 may be flat, curved, or other shape. The width 5890 of the manifold 5815 is greater than the height 5891 of the manifold 5815, which provides the manifold 5815 with flattened shape. However, the width 5890 may also be equal to or less than the height 5891.

The manifold 5815 may be composed of any material capable of being placed at a subcutaneous tissue site. In one example, the manifold 5815 resists collapse when reduced pressure is applied through the manifold 5815. Such resistance may be provided, at least in part, by the structure of the manifold 5815, as well as the material from which the manifold 5815 is made. For example, the hardness of the material from which the manifold 5815 is made may be adjusted such that the manifold 5815 resists collapse when reduced pressure is applied through the manifold 5815. In one embodiment, the manifold 5815 may be composed of silicone, such as medical grade silicone. In another embodiment, the manifold 5815 may be composed of thermoplastic silicone polyetherurethane.

The facilitate the placement of the manifold 5815 at a subcutaneous tissue site, the manifold 5815 may be coated with a lubricant, which may be biocompatible or synthetic. The lubricant may facilitate percutaneous insertion of the manifold 5815, as well as subcutaneous movement of the manifold 5815. In one example, the manifold 5815 is coated with either or both of heparin or parylene.

The flat side 5885 of the manifold 5815 includes slits 5831. The slits 5831 are located on a distal portion of the manifold 5815. Although the manifold 5815 is shown to have three slits 5831, the manifold 5815 may have any number of slits, such as one slit. The slits 5831 extend to the distal end of the manifold 5815. In one example, the slits 5831 may extend across a majority of the length 5894 of the manifold 5815. In another example, the slits 5831 may extend across the entire length 5894 of the manifold 5815.

Each of the slits 5831 are located on a single side, in particular the flat side 5885, of the manifold 5815. However, the slits 5831 may be located on more than side of the manifold 5815. For example, all of the sides of the manifold 5815 may include one or more slits. The slits 5831 may be parallel to one another, and each has the same length. However, the slits 5831 may have any orientation relative to one another. For example, a portion of the slits 5831 may be perpendicular to another portion of the slits 5831. Also, the slits 5831 may have non-uniform lengths, including an example in which each of the slits 5831 have different lengths.

The manifold 5815 may also include an end cap 5870 that is attachable to an end of the manifold 5815 to form a head space, such as head space 2171 in FIG. 31. The end cap 5870 may be permanently or removably attached to the manifold 5815. The head space may accumulate fluid from the at least one purging lumen prior to the fluid being drawn via the at least one reduced-pressure lumen.

The reduced-pressure treatment apparatus 5800 also includes the reduced-pressure delivery tube 5825. The delivery tube 5825 is in fluid communication with the manifold 5815. In one embodiment, the delivery tube 5825 delivers reduced pressure to the at least one reduced-pressure lumen and fluid, such as gas or liquid, to the at least one purge lumen. The delivery tube 5825 may have any cross-sectional shape, such as a circular, elliptical, polygonal, or irregular cross-sectional shape.

The reduced-pressure treatment apparatus 5800 also includes the transition region 5829 disposed between the delivery tube 5825 and the manifold 5815. In one example, the transition region 5829 facilitates fluid communication between the delivery tube 5825 and the manifold 5815. One end 5895 may be sized to fit the delivery tube 5825, while the other end 5896 may be adapted to fit the manifold 5815.

Figure 53:
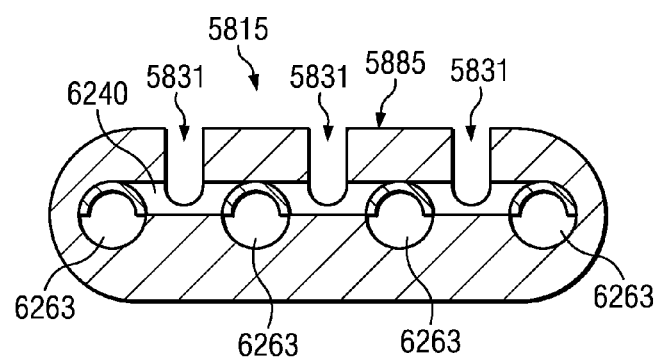
FIG. 53 is a schematic cross-sectional view of a manifold according to an illustrative embodiment.
Figure 54:
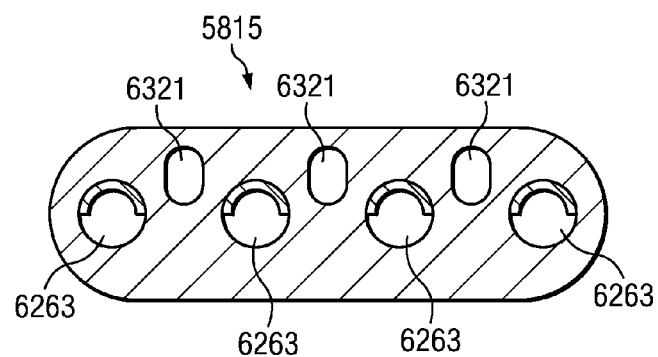
FIG. 54 is a schematic cross-sectional view of a manifold according to an illustrative embodiment.

Referring primarily to FIGS. 53 and 54, cross-sectional views of the manifold 5815 are shown according to an illustrative embodiment. In particular, FIG. 53 is a cross-sectional view of the manifold 5815 taken along line 53-53 in FIG. 49. FIG. 54 is a cross-sectional view of the manifold 5815 taken along line 54-54 in FIG. 49.

The manifold 5815 includes reduced-pressure lumens 6321 to transfer reduced pressure from a reduced-pressure source, such as reduced-pressure source 5495 in FIG. 48. The reduced-pressure lumens 6321 deliver reduced pressure from a reduced-pressure source to a tissue site, or any portion of the manifold 5815. The reduced-pressure lumens 6321 may have any cross-sectional shape, including a circular, elliptical, flattened, irregular, or polygonal cross-sectional shape. In one example, the material from which the manifold 5815 is made may be flexible, causing the cross-sectional shape of the reduced-pressure lumens 6321 to vary depending on fluid flow through the lumens, as well as other factors. In addition, although FIG. 54 shows the manifold 5815 to have three reduced-pressure lumens 6321, the manifold 5815 may have any number of reduced-pressure lumens depending on the particular implementation.

As the reduced-pressure lumens 6321 extend toward the distal end of the manifold 5815, the reduced-pressure lumens 6321 may gradually open toward flat side 5885 to become the slits 5831. In this manner, each of the reduced-pressure lumens 6321 may terminate at a respective slit 5831. Thus, at least one wall of each of the reduced-pressure lumens 6321 may be contiguous with a wall of a respective slit. The number of reduced-pressure lumens 6321 is equal to the number of slits 5831 in the manifold 5815.

Reduced pressure from a reduced-pressure source may be delivered to a tissue site via the slits 5831. Each the slits 5831 allow fluid communication between the reduced-pressure lumens 6321 and a space outside of the manifold 5815, such as a subcutaneous tissue site. In addition to permitting the transfer of reduced pressure from the reduced-pressure lumens 6321 to a tissue site, the slits 6331 may also allow exudate or other fluid from the tissue site to enter the reduced-pressure lumens 6321. The orientation of the slits 6331 relative to the reduced-pressure lumens 6321, including, in some cases, a perpendicular orientation, may also help prevent soft tissue from entering the reduced-pressure lumens 6321, thereby preventing blockages and soft tissue damage.

The manifold 5815 also includes purging lumens 6263. Although the manifold 5815 is shown to have four purging lumens 6263, the manifold 5815 may have any number of purging lumens. The purging lumens 6263, which are another non-limiting embodiment of the second conduit 2163 in FIGS. 30 and 31, are operable to deliver a fluid to a distal portion of the manifold 5815, including the end of the manifold 5815. The purging lumens 6263 may also deliver a fluid to the tissue space around the manifold 5815. The fluid delivered by the purging lumens 6263 may be a gas, such as air, or a liquid. In one embodiment, one or more of the purging lumens 6263 may be a sensing lumen. The reduced pressure at a subcutaneous tissue site may be detectable using the one or more sensing lumens.

The purging lumens 6263 may have any cross-sectional shape, including an circular, elliptical, flattened, irregular, or polygonal cross-sectional shape. In one example, the material from which the manifold 5815 is made may be flexible, causing the cross-sectional shape of the purging lumens 6263 to vary depending on fluid flow through the lumens.

The manifold 5815 includes interlumen channel 6240. The interlumen channel 6240 fluidly connects, or otherwise provides fluid communication between the purging lumens 6263 and either or both of the reduced-pressure lumens 6321 and the slits 5831. In one example, the reduced-pressure lumens 6321 draw purging fluid from the purging lumens 6263 via the interlumen channel 6240. In another example, positive pressure in the purging lumens 6263 forces the fluid from the purging lumens 6263 to the reduced-pressure lumens 6321 via the interlumen channel 6240. The positive pressure in the purging lumens 6263 may be supplied by a positive pressure source.

The manifold 5815 may include any number of interlumen channels, such as interlumen channel 6240. For example, the manifold 5815 may include two or more interlumen channels that are located at any point along the length 5894 of the manifold 5815. In one non-limiting example, the interlumen channels 6240 may be uniformly or non-uniformly spaced apart from one another. In another non-limiting example, the interlumen channels 6240, or a number of the interlumen channels 6240, may be closer to one another at designated portions of the manifold 5815, such as the portion of the manifold 5815 that includes slits 5831. In another non-limiting example, all of the interlumen channels 6240 may be located at the portion of the manifold 5815 that includes slits 5831. The number of interlumen channels may control the rate of fluid being transferred, or the cross-flow, from the purging lumens 6263 to the reduced-pressure lumens 6321. The inclusion of two or more interlumen channels 6240 may allow continued fluid communication between the purging lumens 6263 and the reduced-pressure lumens 6321 in the event that one or more of the interlumen channels becomes blocked or occluded by fibrin or other materials.

In another example, the transfer of fluid from the purging lumens 6263 to the reduced-pressure lumens 6321 may occur via the head space that is formed by coupling an end of the manifold 5815 to the end cap 5870 in FIGS. 49-52. In one embodiment, the head space may provide the sole passageway through which fluid is transferred from the purging lumens 6263 to the reduced-pressure lumens 6321. In this embodiment, no interlumen channel 6240 may be present in the manifold 5815.

Figure 55:
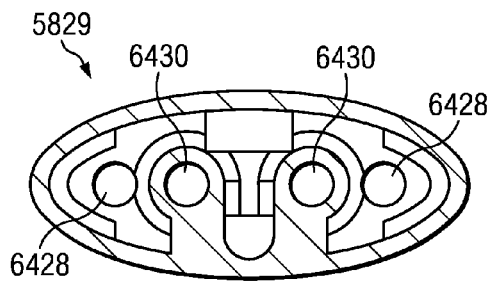
FIG. 55 is a schematic cross-sectional view of a transition region according to an illustrative embodiment.
Figure 56:
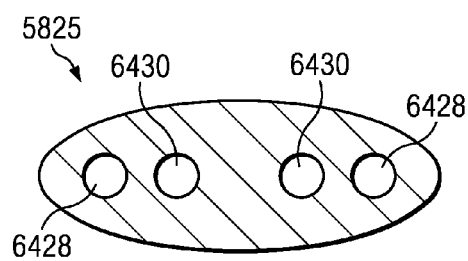
FIG. 56 is a schematic cross-sectional view of a delivery tube according to an illustrative embodiment.

Referring primarily to FIGS. 55 and 56, cross-sectional views of the reduced-pressure treatment apparatus 5800 are shown according to an illustrative embodiment. In particular, FIG. 55 is a cross-sectional view of the transition region 5829 as shown from the perspective of cross-sectional indicator 56 in FIG. 49. FIG. 56 is a cross-sectional view of the delivery tube 5825 as shown from the perspective of cross-sectional indicator 56 in FIG. 49.

The delivery tube 5825 includes fluid delivery lumens 6430 that may deliver fluid to the purging lumens 6263 in FIGS. 53 and 54. The delivery tube 5825 also includes reduced-pressure delivery lumens 6428 that may deliver reduced pressure to the reduced-pressure lumens 6321, as well as other parts of the manifold 5815 and an adjacent tissue site.

The number of purging lumens 6263 in the manifold 5815 may exceed the number of fluid delivery lumens 6430 in the delivery tube 5825. Also, the number of reduced-pressure lumens 6321 in the manifold 5815 may exceed the number of reduced-pressure delivery lumens 6428 in the delivery tube 5825. The number of lumens increases from the delivery tube 5825 to the manifold 5815 in this manner at the transition region 5829, which acts as the interface between the delivery tube 5825 and the manifold 5815.

In one embodiment, the transition region 5829 includes at least one cavity. In one example, the fluid delivery lumens 6430 may be in fluid communication with the purging lumens 6263 via the cavity. In this example, the fluid delivery lumens 6430 may be coupled, or otherwise fluidly connected, to an end of the cavity that is nearer the delivery tube 5825. The purging lumens 6263 may be coupled, or otherwise fluidly connected, to an end of the cavity that is nearer the manifold 5815. Providing a cavity in this manner permits the number of the fluid delivery lumens 6430 and the purging lumens 6263 to be varied while still maintaining fluid communication between them.

In another example, the reduced-pressure delivery lumens 6428 may be in fluid communication with the reduced-pressure lumens 6321 via the cavity. In this example, the reduced-pressure delivery lumens 6428 may be coupled, or otherwise fluidly connected, to an end of the cavity that is nearer the delivery tube 5825. The reduced-pressure lumens 6321 may be coupled, or otherwise fluidly connected, to an end of the cavity that is nearer the manifold 5815. Providing a cavity in this manner permits the number of the reduced-pressure delivery lumens 6428 and the reduced-pressure lumens 6321 to be varied while still maintaining fluid communication between them. In addition, the transition region may include two cavities, one of which provides fluid communication between the fluid delivery lumens 6430 and the purging lumens 6263, the other of which provides fluid communication between the reduced-pressure delivery lumens 6428 and the reduced-pressure lumens 6321.

In another embodiment, the transition region 5829 includes one or more branching or forking pathways that allow fluid communication between a lesser number of fluid delivery lumens and a greater number of purging lumens. The transition region 5829 may also include one or more branching or forking pathways that allow fluid communication between a lesser number of reduced-pressure delivery lumens and a greater number of reduced-pressure lumens.

Figure 57:
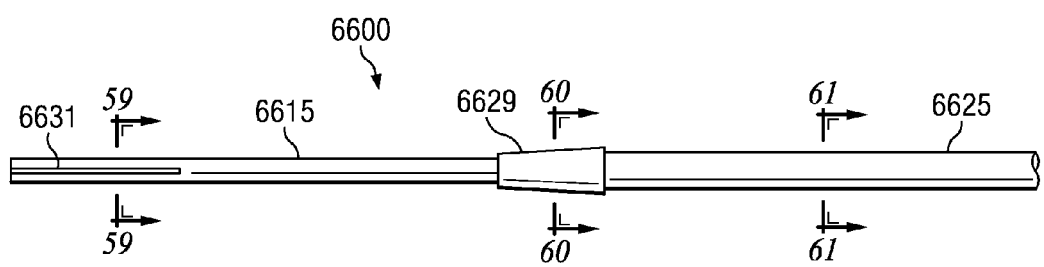
FIG. 57 is a schematic plan view of an apparatus for applying reduced pressure to a subcutaneous tissue site according to an illustrative embodiment.
Figure 58:
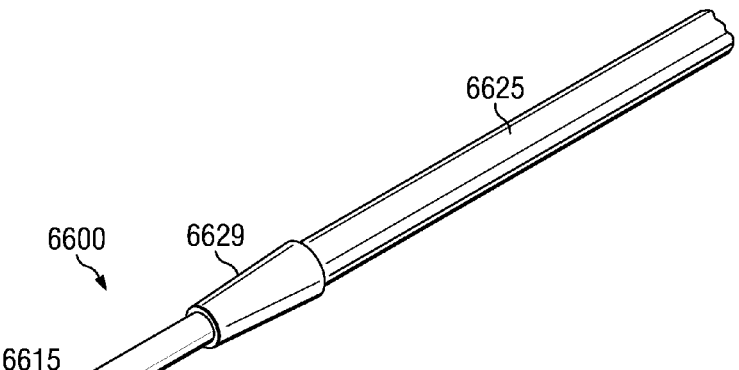
FIG. 58 is a schematic perspective view of an apparatus for applying reduced pressure to a subcutaneous tissue site according to an illustrative embodiment.

Referring primarily to FIGS. 57 and 58, a reduced-pressure treatment apparatus 6600 is shown according to an illustrative embodiment. The reduced-pressure treatment apparatus 6600 includes a manifold 6615, a transition region 6629, and a delivery tube 6625. The reduced-pressure treatment apparatus 6600 delivers reduced pressure from a reduced-pressure source, such as reduced-pressure source 5495 in FIG. 48, to a subcutaneous tissue site through slits 6631 (only one of which is shown in FIGS. 57 and 58). The reduced-pressure treatment apparatus 6600 also includes a purging function that helps to prevent blockages from forming in the manifold 6615.

In contrast to the manifold 5815 in FIGS. 49-53, the manifold 6615 has a substantially cylindrical shape, as well as a substantially circular cross-sectional shape. In other embodiments, the manifold 5815 may have any cross-sectional shape, such as a substantially rectangular, substantially polygonal, substantially triangular, substantially elliptical, star, or irregular cross-sectional shape.

Figure 59:
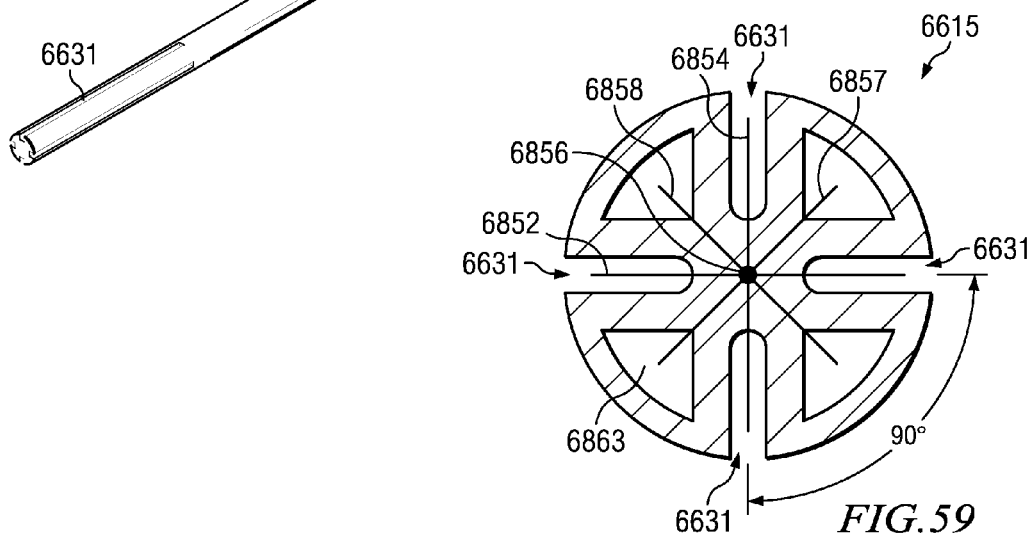
FIG. 59 is a schematic cross-sectional view of a manifold according to an illustrative embodiment.

Referring primarily to FIG. 59, a cross-sectional view of the manifold 6615 taken along line 59-59 in FIG. 57 is shown according to an illustrative embodiment. FIG. 59 shows the spatial orientation of the purging lumens 6863 and the slits 6631.

Figure 49:
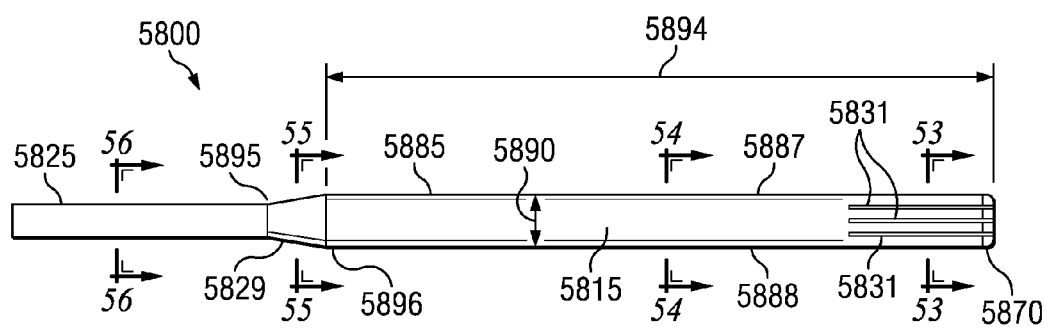
FIG. 49 is a schematic plan view of an apparatus for applying reduced pressure to a subcutaneous tissue site according to an illustrative embodiment.
Figure 50:
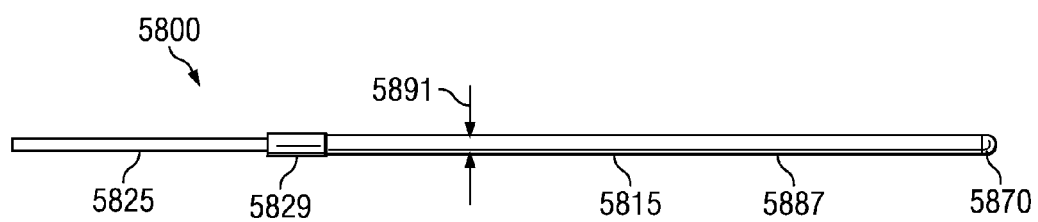
FIG. 50 is a schematic side view of an apparatus for applying reduced pressure to a subcutaneous tissue site according to an illustrative embodiment.
Figure 52:
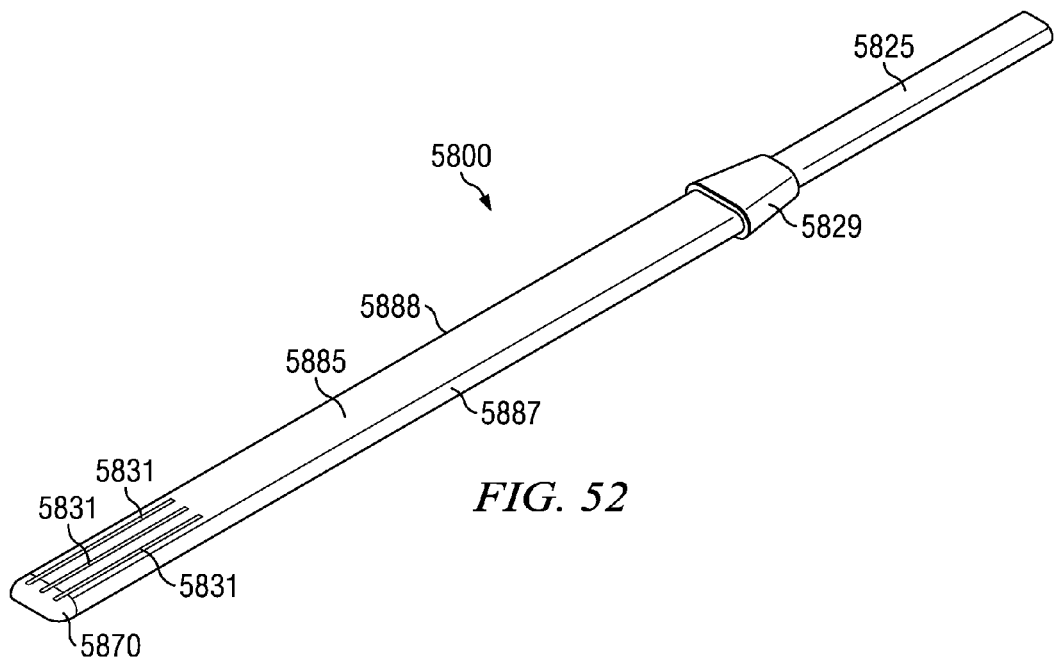
FIG. 52 is a schematic perspective view of an apparatus for applying reduced pressure to a subcutaneous tissue site according to an illustrative embodiment.

In contrast to the slits 5831 in FIGS. 49, 52, and 53, the slits 6631 are spaced at equal intervals around an outer surface of the manifold 6615. In particular, the manifold 6615 includes four slits 6631 that are spaced at ninety degree intervals from one another. Also, an axis 6852 formed by a first pair of slits is perpendicular to an axis 6854 formed by a second pair of slits. Although four slits 6631 are shown on the manifold 6615, the manifold 6615 may include any number of slits. Also, the slits 6631 may be spaced at non-uniform intervals from one another, or may all be located on a single side of the manifold 6615.

Each of the purging lumens 6863 is substantially pie-shaped. A pie shape may include a triangle modified in that one or more sides is/are curved. In addition, the purging lumens 6863 are spaced at equal intervals around a central longitudinal axis 6856 of the manifold 6615. Each of the four purging lumens 6863 are located in a separate quadrant of the manifold 6615, and are spaced at ninety degree intervals from one another. An axis 6857 formed by a first pair of purging lumens is perpendicular to an axis 6858 formed by a second pair of purging lumens. Although four purging lumens 6863 are shown in the manifold 6615, the manifold 6615 may include any number of purging lumens. Also, the purging lumens 6863 may be spaced at non-uniform intervals from one another.

Figure 60:
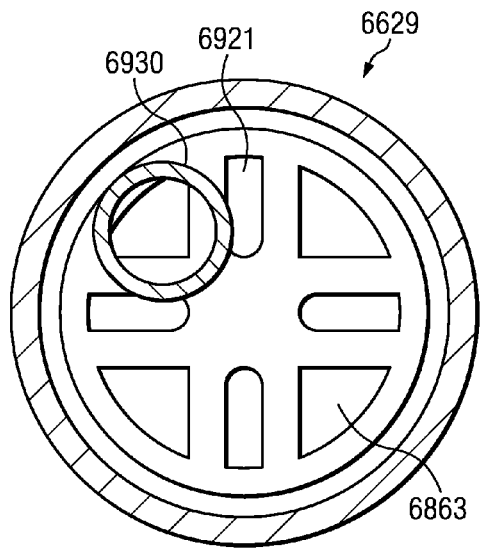
FIG. 60 is a schematic cross-sectional view of a transition region according to an illustrative embodiment.
Figure 61:
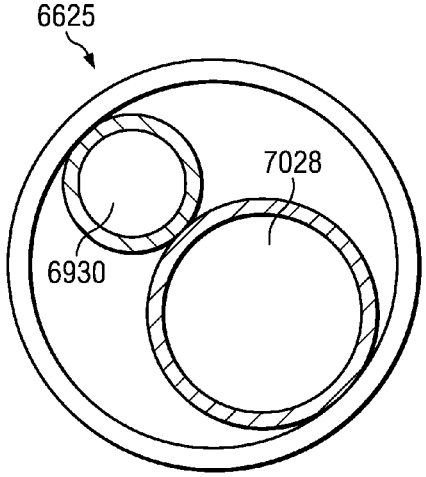
FIG. 61 is a schematic cross-sectional view of a delivery tube according to an illustrative embodiment.

Referring primarily to FIGS. 60 and 61, cross-sectional views of the reduced-pressure treatment apparatus 6600 are shown according to an illustrative embodiment. In particular, FIG. 60 is a cross-sectional view of the transition region 6629 taken along line 60-60 in FIG. 57. FIG. 61 is a cross-sectional view of the delivery tube 6625 taken along line 61-61 in FIG. 57.

The delivery tube 6625 includes fluid delivery lumen 6930 that may deliver fluid to the purging lumens 6863 in FIGS. 59 and 60. The delivery tube 6625 also includes reduced-pressure delivery lumen 7028 that may deliver reduced pressure to the reduced-pressure lumens 6921, as well as other parts of the manifold 6615 and an adjacent tissue site. The reduced-pressure delivery lumen 7028 is shown to have a larger diameter than the fluid delivery lumen 6930, although each of these lumens may have any size relative to one another.

The number of lumens increases from the delivery tube 6625 to the manifold 6615 at the transition region 6629, which acts as the interface between the delivery tube 6625 and the manifold 6615.

Figure 62:
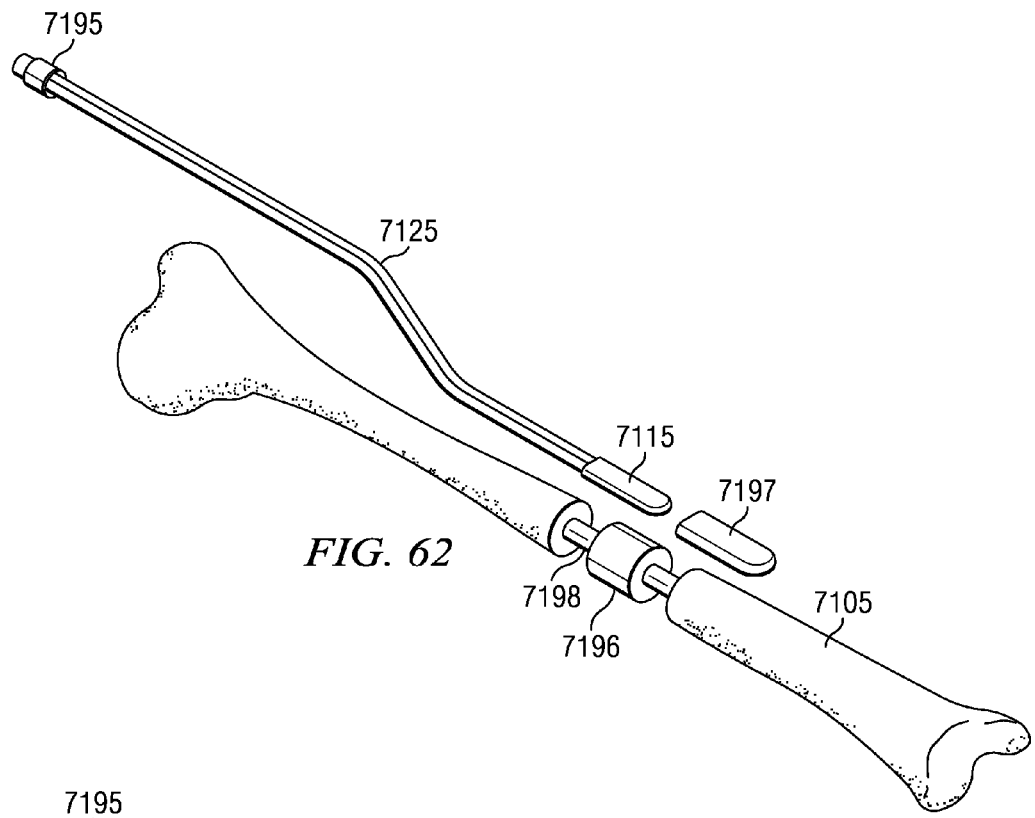
FIG. 62 is a schematic perspective view of an apparatus for applying reduced pressure to a subcutaneous tissue site according to an illustrative embodiment.
Figure 63:
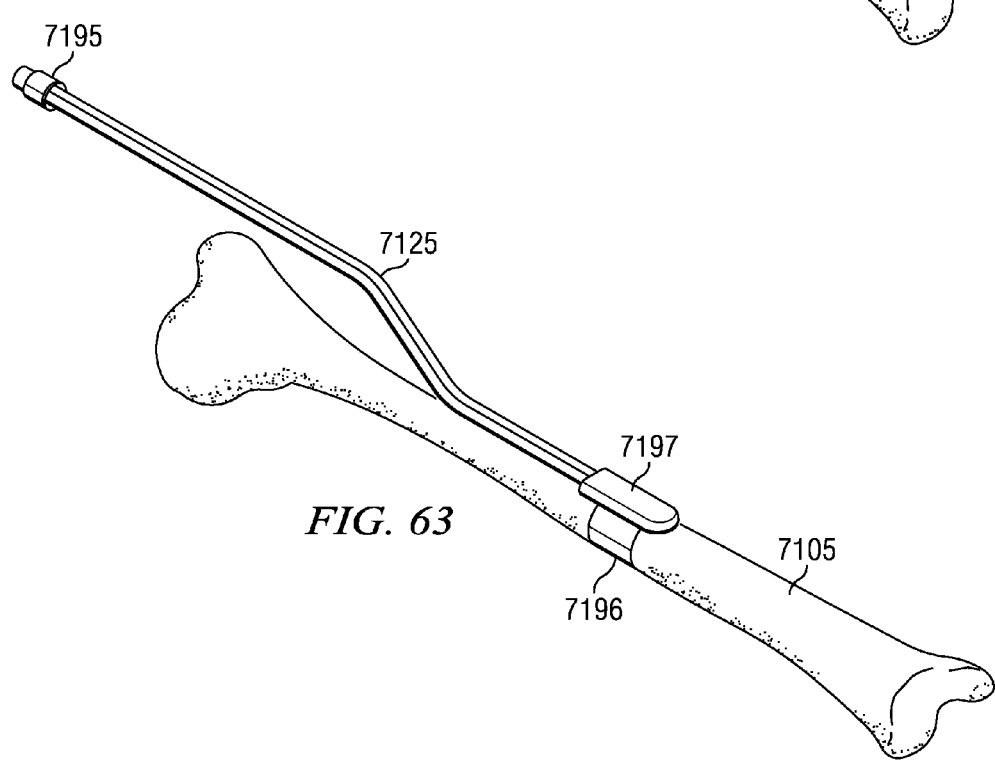
FIG. 63 is a schematic perspective view of an apparatus for applying reduced pressure to a subcutaneous tissue site according to an illustrative embodiment.

Referring primarily to FIGS. 62 and 63, the application of a manifold 7115 to a subcutaneous tissue site 7105 is shown according to an illustrative embodiment. The manifold 7115 includes a felt envelope 7197 that may cover at least a portion of the outer surface of the manifold 7115 and may serve as a second manifold, e.g., second manifold 5488 in FIG. 47. In one example, the felt envelope 7197 may cover a majority or all of the outer surface of the manifold 7115. The felt envelope 7197 may help to prevent soft tissue from blocking openings, apertures, or slits in the manifold 7115, and may help to prevent tissue damage when the manifold 7115 is removed from the subcutaneous tissue site 7105.

In one embodiment, a method for applying reduced pressure to the subcutaneous tissue site 7105 includes applying the manifold 7115 to the subcutaneous tissue site 7105. The manifold 7115 may be percutaneously inserted into a patient, and the manifold 7115 may be positioned adjacent to or abutting the subcutaneous tissue site 7105. The symmetrical design of the manifold included in at least a portion of the illustrative embodiments may facilitate the implantation of the manifold in any orientation.

In the example in which the subcutaneous tissue site 7105 includes a defect, such as a fracture, a scaffold 7196 may be positioned at the defect site to improve healing and tissue generation characteristics. The scaffold 7196 may be adjoined to the subcutaneous tissue site 7105 using a tibial nail 7198.

The delivery tube 7125 may be used to facilitate placement of the manifold 7115 at the subcutaneous tissue site 7105. The delivery tube 7125 may be coupled to a reduced-pressure source via a purge/reduced-pressure connector 7195.

In one embodiment, a method of manufacturing an apparatus for applying reduced pressure to the subcutaneous tissue site 7105 includes forming manifold 7115. The method may also include providing the delivery tube 7125 and coupling the delivery tube 7125 to the manifold 7115 such that the delivery tube 7125 is in fluid communication with the manifold 7115.

Figure 64:
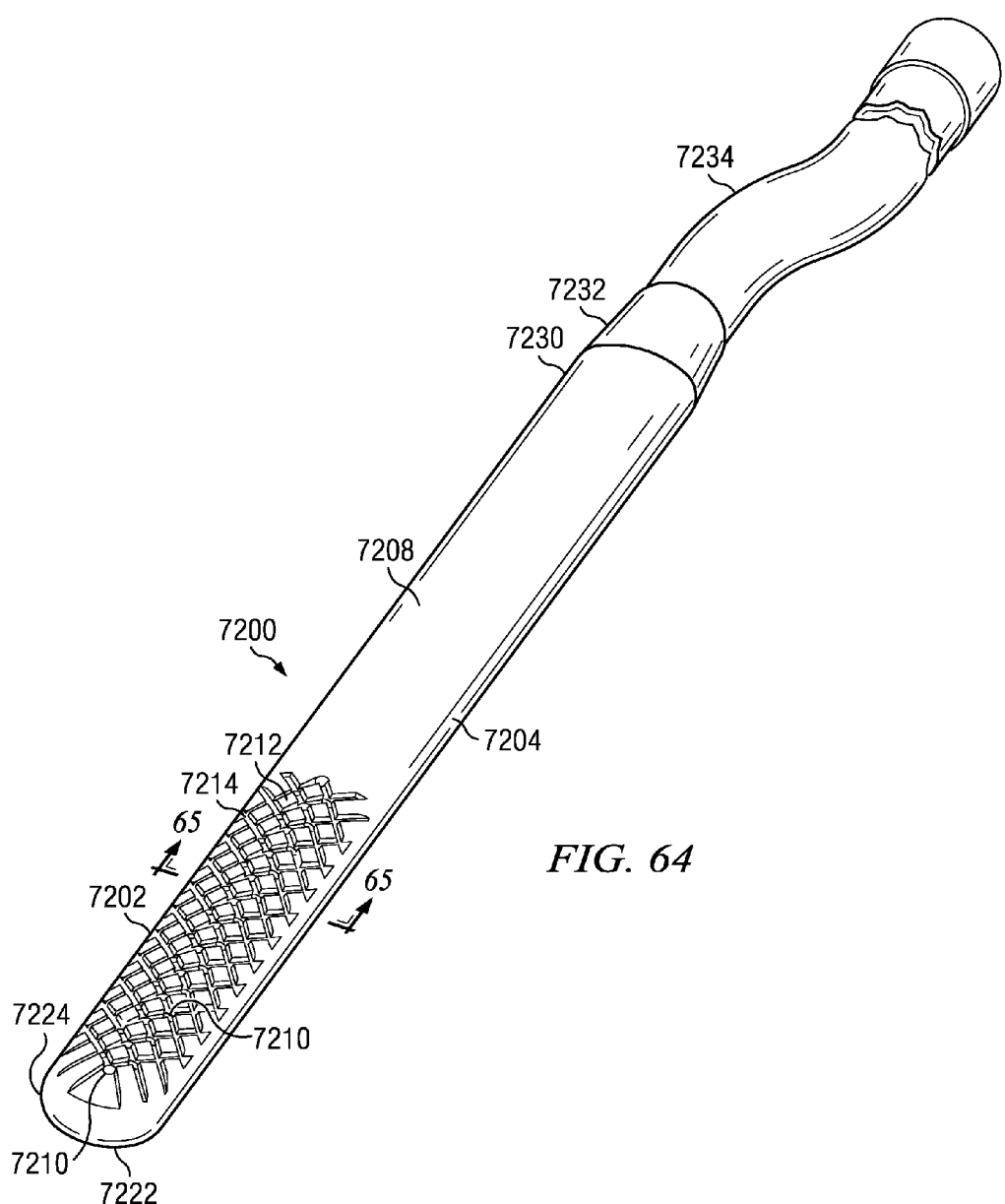
FIG. 64 is a schematic perspective view of another illustrative embodiment of a reduced pressure delivery apparatus.
Figure 65:
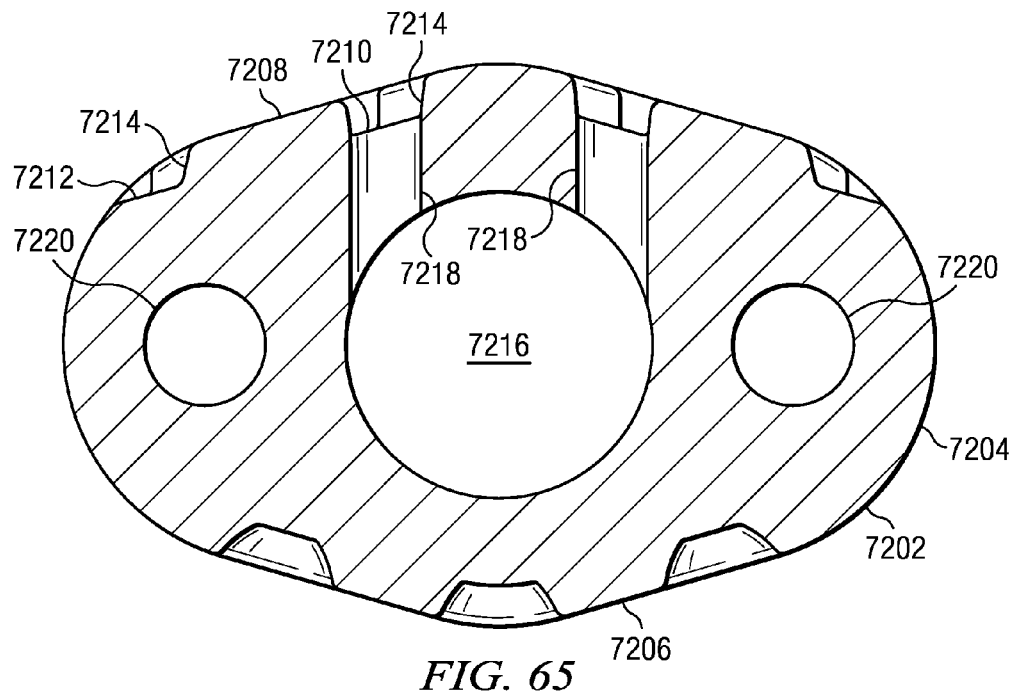
FIG. 65 is a schematic cross sectional view taken along line 65-65 in FIG. 64.
Figure 66:
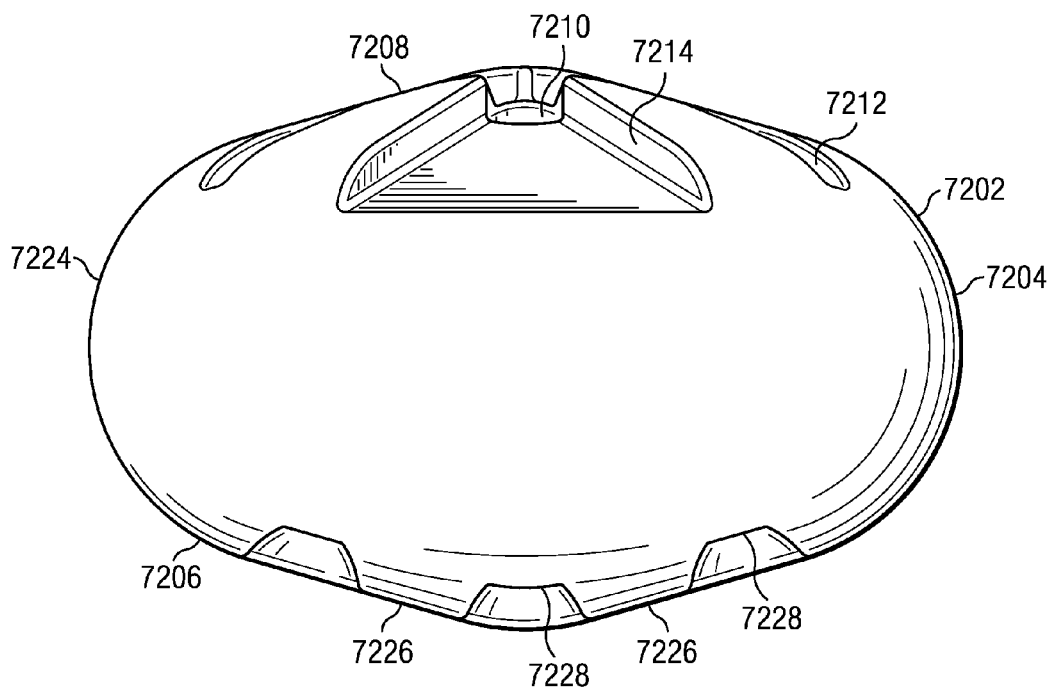
FIG. 66 is a schematic end view of the reduced pressure delivery apparatus of FIGS. 64 and 65 showing an end cap.
Figure 67:
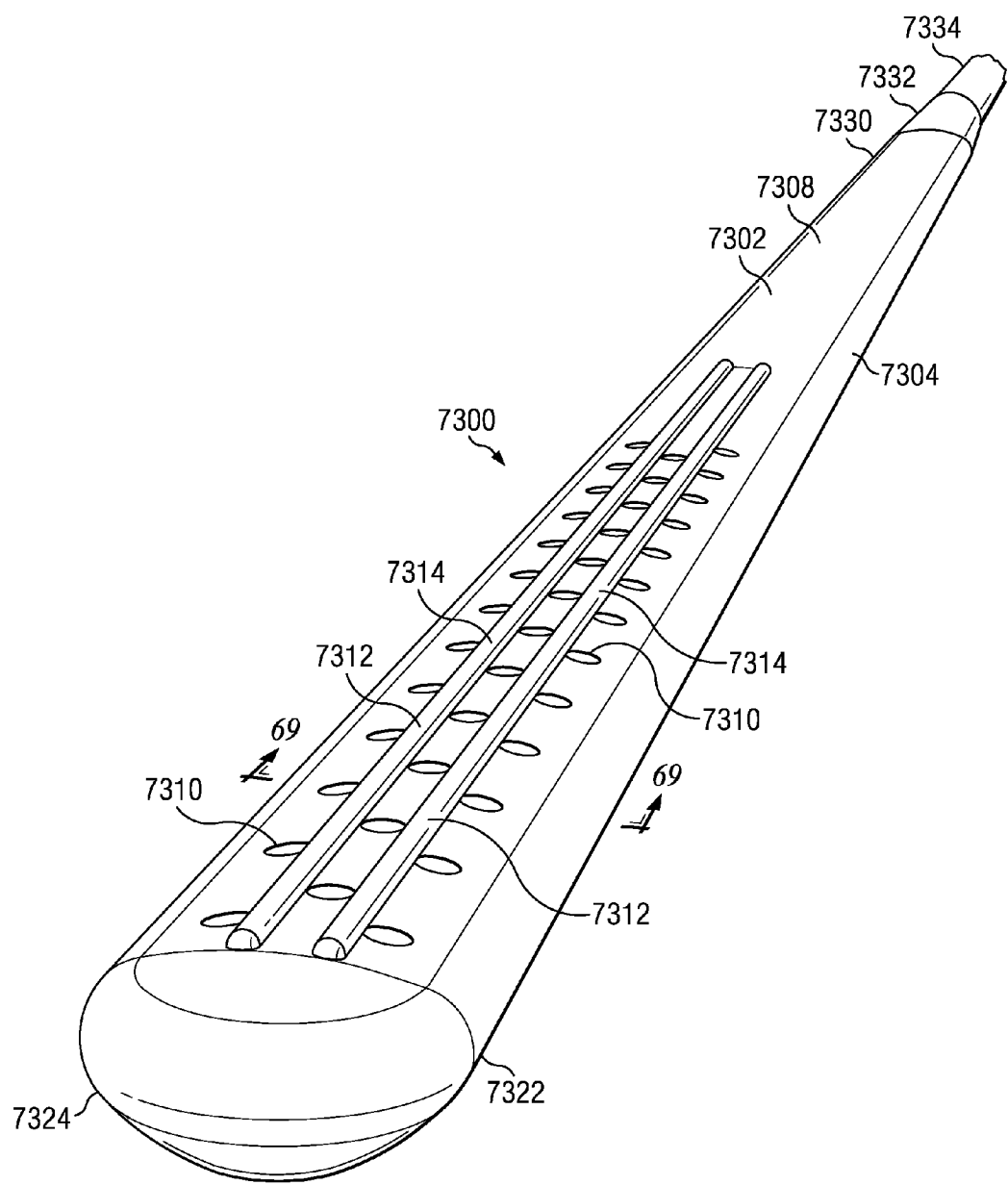
FIG. 67 is a schematic perspective view of another illustrative embodiment of a reduced pressure delivery apparatus.
Figure 68:
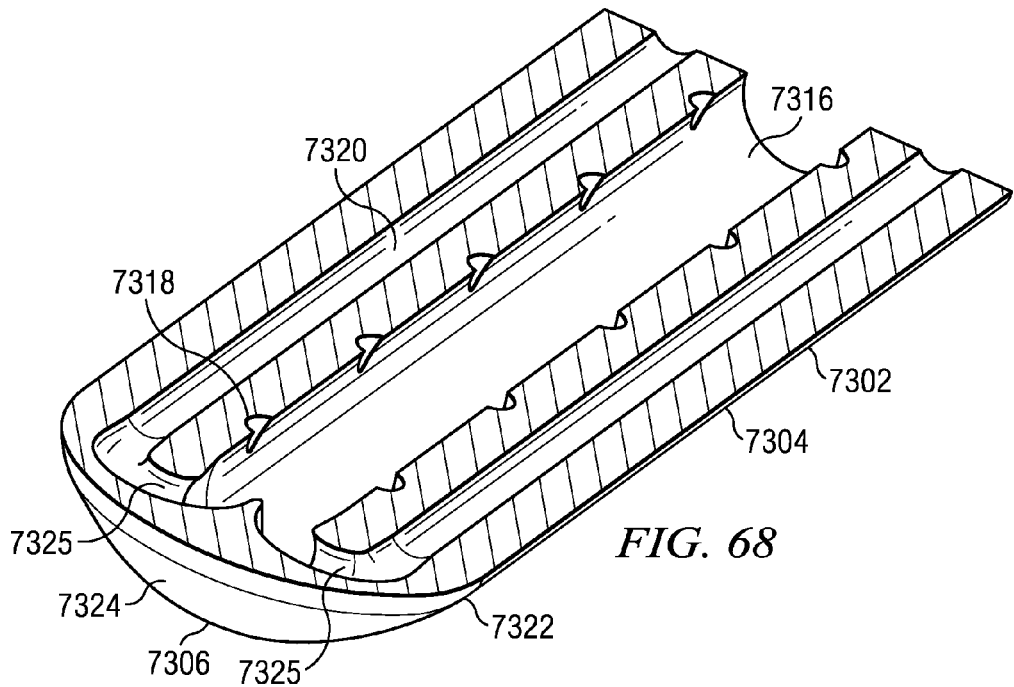
FIG. 68 is a schematic, perspective view of a portion of the reduced pressure delivery apparatus of FIG. 67 with a portion broken away to shown an interior portion.
Figure 69:
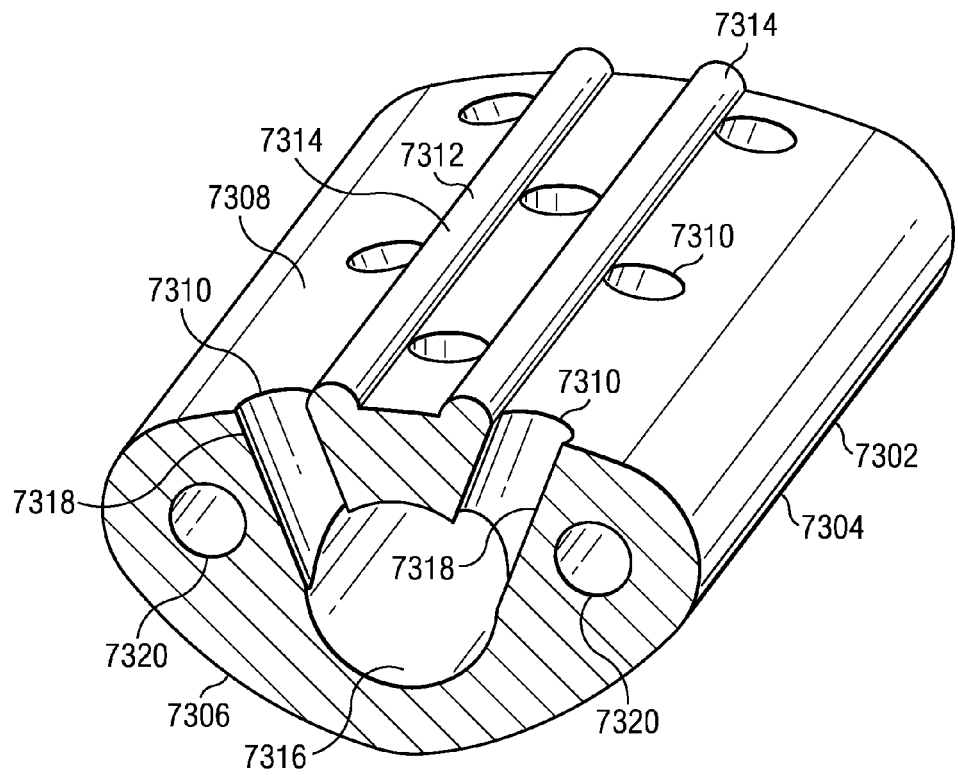
FIG. 69 is a schematic, cross sectional view taken along line 69-69 in FIG. 67.
Figure 70:
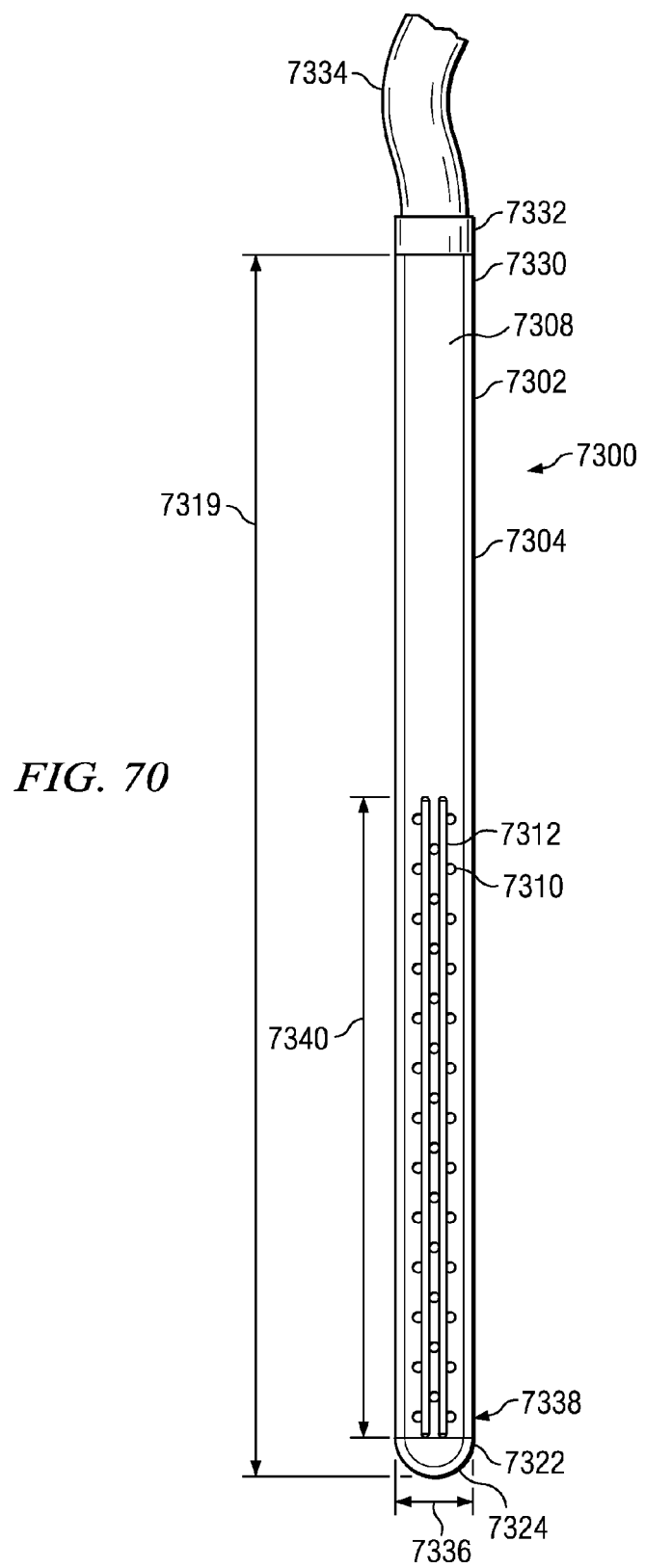
FIG. 70 is a schematic, plan view of the reduced pressure delivery apparatus of FIGS. 67-69.

Referring now primarily to FIGS. 64-66, another illustrative embodiment of a reduced-pressure delivery apparatus 7200 is presented. The reduced-pressure delivery apparatus 7200 includes a manifold 7202 having a longitudinal manifold body 7204 and having a first side 7206 and a second, tissue-facing side 7208. The reduced-pressured delivery apparatus 7200 delivers reduced pressure from a reduced pressure source, such as reduced-pressure source 5495 in FIG. 49, to a subcutaneous tissue site, such as a bone or more particularly a vertebrae or multiple vertebra, through a plurality of apertures 7210 formed on the second, tissue-facing side 7208 of the longitudinal manifold body 7204. The plurality of apertures 7210 may be further distributed or manifolded by a plurality of manifolding surface features 7212, such as a plurality of recesses 7214 or rounded grooves. The plurality of recesses 7214 may be asymmetrical to facilitate percutaneous removal.

The plurality of apertures 7210 are associated with the plurality of manifolding surface features 7212, which help distribute the reduced pressure. The plurality of apertures 7210 fluidly couple the plurality of manifold surface features 7212 to an evacuation lumen or reduced-pressure lumen 7216 by conduits 7218. The reduced-pressure lumen 7216 may be one or a plurality of conduits for delivering reduced pressure and removing fluids. The reduced-pressure lumen 7216 runs the longitudinal length of the longitudinal manifold body 7204. The longitudinal manifold body 7204 also contains at least one purging lumen or conduit 7220. The one or more purging lumens 7220 also run the longitudinal length of the longitudinal manifold body 7204. At a distal end 7222 of the manifold 7202 is an end cap 7224. The end cap 7224 may be formed integrally as part of the longitudinal manifold body 7204.

The end cap 7224 provides head space (not shown) that allows the purging fluid within the one or more purging lumens 7220 to be fluidly coupled to the reduced-pressure lumen 7216. The first side 7206 of the longitudinal manifold body 7204 near the distal end 7222 may also have a plurality of ridges 7226 and second plurality of recesses 7228.

A proximal end 7230 out of the longitudinal manifold body 7204 may have a connector 7232 to facilitate connection with a reduced-pressure delivery tube or conduit 7234. The reduced-pressure delivery tube 7234 may be a multi-lumen conduit that provides reduced pressure from the reduced-pressure source to the reduced-pressure lumen 7216 of the manifold 7202 and provides a purging fluid to the one or more purging lumens 7220.

In operation, the reduced-pressure delivery apparatus 7200 is used in a manner analogous to the embodiments previously presented. Thus, the second, tissue-facing side 7208 of the manifold 7202 is positioned proximate the tissue site and reduced pressure is supplied. The reduced pressure is delivered to the tissue site through the apertures 7210 and the manifolding surface features 7212. A purging fluid, e.g., air, is used to help remove or avoid blocking of the reduced pressure lumen 7216 and to prevent hydrostatic equilibrium.

Referring now primarily to FIGS. 67-70, another illustrative embodiment of a reduced-pressure delivery apparatus 7300 is presented. The reduced-pressure delivery apparatus 7300 includes a manifold 7302 having a longitudinal manifold body 7304, which has a first side 7306 and a second, tissue-facing side 7308. The manifold 7302 may be formed by injection molding. Injection molding of the manifold 7302 may help to avoid portions breaking or being otherwise at risk of being left in the patient's body. The manifold 7302 may also be extruded into parts and then bonded or otherwise coupled to form an integral unit. Alternatively, the manifold 7302 may be extruded and then undergo a secondary controlled melt "tipping" process to form an integral unit. The manifold 7302 may be made from a flexible or semi-rigid material. For example, the manifold 7302 may be made from any medical-grade polymer, such as polyurethane, etc. In one embodiment, the manifold 7302 is made from a material with a stiffness of approximately 80 Shore A, but other stiffnesses may be used. A coating may be added to the manifold 7302 to avoid material buildup on the manifold 7302.

A plurality of apertures 7310 are formed on the second, tissue-facing side 7308 of the longitudinal manifold body 7304 for providing reduced pressure to a subcutaneous tissue site, such as a bone. While the apertures are shown in a symmetrical space pattern, it should be understood that the apertures may be formed with any pattern or with a random placement. A plurality of manifold surface features 7312 are formed on the second, tissue-facing side 7308. The plurality of manifold surface features 7312 may include a plurality of standoffs or offsets 7314. The plurality of offsets 7314 may be formed integrally with or coupled to the second, tissue-facing side 7308 of the longitudinal manifold body 7304. The offsets 7314 may be any surface feature creating effective flow channels between the second, tissue-facing side 7308 and the tissue site. The surface features 7312 may detach from the manifold body 7304 when the manifold 7302 is percutaneously removed, and the surface features 7312 may be bioresorbable.

The apertures 7310 are fluidly coupled to reduced-pressure lumen 7316 formed in the longitudinal manifold body 7304. The reduced-pressure lumen 7316 is fluidly coupled to the apertures 7310 by a plurality of conduits 7318. The reduced-pressure lumen 7316 runs the length 7319 of the longitudinal manifold body 7304. The longitudinal manifold body 7304 is also formed with one or more purging lumens 7320 which also run the length 7319 of the longitudinal manifold body 7304. While the illustrative embodiment shows two purge lumens 7320, it should be understood that any number may be used. Additionally, the two purge lumens 7320 are shown symmetrically spaced about the reduced-pressure lumen 7316, and while the symmetric orientation of the two purge lumen 7320 does enhance performance in that the performance is not degradated by different orientations, other orientations may be used. Additional lumens, such as a pressure sensing lumen, may be included within the longitudinal manifold body 7304.

On the distal end 7322 of the longitudinal manifold body 7304 an end cap 7324 is formed or coupled. The end cap 7324 is formed with a header space 7325 that allows the one or more purging lumens 7320 to be fluidly coupled to the reduced-pressure lumen 7316. The end cap 7324 is formed integrally to the or as part of the longitudinal manifold body 7304 and thus, avoids the risk of the end cap becoming dislodged during removal from the patient's body.

At the proximal end 7330 of the longitudinal manifold body 7304, a connector 7332 may be coupled to provide easy connection with a reduced-pressure delivery tube or conduit 7334, which in turn is fluidly coupled to a reduced pressure source and also a source of a purging fluid or liquid. The reduced-pressure delivery tube 7334 may be a multi-lumen conduit that delivers reduced pressure to the reduced-pressure lumen 7316 and provides the purging fluid to the one or more purging lumens 7320. The purging fluid may be, for example, atmospheric air.

The longitudinal manifold body 7304 has the length 7319 and a width 7336. Typically a treatment area 7338, which has a longitudinal length of 7340 is formed close to the distal end 7322. The longitudinal manifold body 7304 typically has an aspect ratio, which is the length 7319 divided by the width 7336, that is greater than five, and typically greater than 10 or even 20 or more. In one embodiment for a spinal application, the longitudinal length 7340 of the treatment area 7338 is in the range of about 60 to 80 millimeters, but it should be understood that any dimension may be used depending on the application involved.

In one illustrative, non-limiting embodiment, the effective diameter of the lateral cross section of the longitudinal manifold body 7304 is eight millimeters and in another illustrative embodiment is eleven millimeters, but it should be understood that while specific dimensions are given for an example, any size effective diameter may be used. It should also be noted that although a slightly elliptical or triangular shape is presented, the cross sectional shape of the longitudinal manifold body may be any of those previously mentioned or even irregular or other shapes.

In operation, the manifold 7302 may be inserted surgically or using minimally invasive surgery. Typically, the manifold 7302 would be removed percutaneously or in one embodiment may be bio-absorbable and left in place.

The administration of reduced-pressure tissue treatment to a tissue site in accordance with the systems and methods described herein may be accomplished by applying a sufficient reduced pressure to the tissue site and then maintaining that sufficient reduced pressure over a selected period of time. Alternatively, the reduced pressure that is applied to the tissue site may be cyclic in nature. More specifically, the amount of reduced pressure applied may be varied according to a selected temporal cycle. Still another method of applying the reduced pressure may vary the amount of reduced pressure randomly. Similarly, the rate or volume of fluid delivered to the tissue site may be constant, cyclic, or random in nature. Fluid delivery, if cyclic, may occur during application of reduced pressure, or may occur during cyclic periods in which reduced pressure is not being applied. While the amount of reduced pressure applied to a tissue site will typically vary according to the pathology of the tissue site and the circumstances under which reduced-pressure tissue treatment is administered, the reduced pressure will typically be between about −5 mm Hg and −500 mm Hg, but more preferably between about −5 mm Hg and −300 mm Hg.

While the systems and methods of the present disclosure have been described with reference to tissue growth and healing in human patients, it should be recognized that these systems and methods for applying reduced-pressure tissue treatment can be used in any living organism in which it is desired to promote tissue growth or healing. Similarly, the systems and methods of the present disclosure may be applied to any tissue, including, without limitation, bone tissue, adipose tissue, muscle tissue, neural tissue, dermal tissue, vascular tissue, connective tissue, cartilage, tendons, or ligaments. While the healing of tissue may be one focus of applying reduced-pressure tissue treatment as described herein, the application of reduced-pressure tissue treatment, especially to tissues located beneath a patient's skin, may also be used to generate tissue growth in tissues that are not diseased, defective, or damaged. For example, it may be desired to use the percutaneous implantation techniques to apply reduced-pressure tissue treatment to grow additional tissue at a tissue site that can then be harvested. The harvested tissue may be transplanted to another tissue site to replace diseased or damaged tissue, or alternatively the harvested tissue may be transplanted to another patient.

It is also important to note that the reduced-pressure delivery apparatuses described herein may be used in conjunction with scaffold material to increase the growth and growth rate of new tissue. The scaffold material could be placed between the tissue site and the reduced-pressure delivery apparatus, or the reduced-pressure delivery apparatus could itself be made from bioresorbable material that serves as a scaffold to new tissue growth.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in a connection to any one embodiment may also be applicable to any other embodiment.

We claim:

1. A system for applying reduced pressure to a subcutaneous tissue site on a patient, the system comprising:
   a reduced-pressure source operable to supply reduced pressure;
   a fluid source operable to supply a purging fluid;
   a manifold having a flattened shape including a flat side and an opposing side opposite the flat side, a width defined by the width of the flat side and a height defined by the distance between the flat side and the opposing side wherein the width is greater than the height, and a distal portion adapted to be inserted in the patient and placed at the subcutaneous tissue site, the manifold comprising:
      at least one purging lumen formed in the manifold and in fluid communication with the fluid source to deliver the purging fluid to the distal portion of the manifold,
      at least one slit formed in the flat side only at the distal portion of the manifold and adapted to be facing the subcutaneous tissue site, and
      at least one reduced-pressure lumen formed in the manifold, the at least one reduced-pressure lumen extending toward the distal end of the manifold and opening toward the flat side of the manifold to become the at least one slit, wherein the at least one reduced-pressure lumen is operable to deliver reduced pressure supplied from the reduced-pressure source to the subcutaneous tissue site via the at least one slit; and
   a delivery tube in fluid communication with the manifold, the delivery tube having at least one reduced-pressure delivery lumen adapted to deliver reduced pressure to the at least one reduced-pressure lumen and having at least one fluid delivery lumen adapted to deliver the purging fluid to the at least one purging lumen.

2. The system of claim 1, wherein the manifold further comprises at least one interlumen channel fluidly interconnecting at least two of the at least one purging lumen, and the at least one reduced-pressure lumen.

3. The system of claim 1, wherein the at least one slit extends to the distal end of the manifold.

4. An apparatus for applying reduced pressure to a subcutaneous tissue site on a patient, the apparatus comprising:
a manifold having a flattened shape including a flat side and an opposing side opposite the flat side, a width defined by the width of the flat side and a height defined by the distance between the flat side and the opposing side wherein the width is greater than the height, and a distal portion adapted to be inserted into the patient and for placement at the subcutaneous tissue site, the manifold comprising:
at least one purging lumen formed in the manifold and operable to deliver a purging fluid to the distal portion of the manifold,
at least one slit formed in the flat side only at the distal portion of the manifold and adapted to be facing the subcutaneous tissue site,
at least one reduced-pressure lumen formed in the manifold, the at least one reduced-pressure lumen extending toward the distal end of the manifold and opening toward the flat side of the manifold to become the at least one slit, wherein the at least one reduced-pressure lumen is operable to deliver reduced pressure to the subcutaneous tissue site via the at least one slit; and
an end cap that is attachable to an end of the manifold to form a head space, and wherein the head space is adapted to accumulate fluid from the at least one purging lumen prior to the fluid being drawn via the at least one reduced-pressure lumen.

5. The apparatus of claim 4, wherein the manifold further comprises at least one interlumen channel fluidly interconnecting at least two of the at least one purging lumen, and the at least one reduced-pressure lumen.

6. The apparatus of claim 4, wherein the at least one reduced-pressure lumen terminates at the at least one slit.

7. The apparatus of claim 4, further comprising:
a delivery tube in fluid communication with the manifold, the delivery tube delivering reduced pressure to the at least one reduced-pressure lumen and the purging fluid to the at least one purging lumen,
wherein the delivery tube has at least one fluid delivery lumen and at least one reduced-pressure delivery lumen,
wherein the at least one fluid delivery lumen delivers the fluid to the at least one purging lumen, and
wherein the at least one reduced-pressure delivery lumen delivers reduced pressure to the at least one reduced-pressure lumen.

8. The apparatus of claim 4, wherein the manifold is coated with at least one of heparin and parylene.

9. A method for applying reduced pressure to a subcutaneous tissue site, the method comprising:
applying a manifold having a flattened shape including a flat side and an opposing side opposite the flat side, a width defined by the width of the flat side and a height defined by the distance between the flat side and the opposing side wherein the width is greater than the height, and a distal portion to the subcutaneous tissue site, the manifold comprising:
at least one purging lumen operable to deliver a fluid to the distal portion of the manifold,
at least one slit formed in the flat side only at the distal portion of the manifold and adapted to be facing the subcutaneous tissue site, and
at least one reduced-pressure lumen extending toward the distal end of the manifold and opening toward the flat side of the manifold to become the at least one slit, the at least one reduced-pressure lumen operable to deliver reduced pressure to the subcutaneous tissue site via the at least one slit;
supplying a reduced pressure to the manifold via a reduced-pressure delivery lumen in a delivery tube; and
supplying the fluid to the manifold via a fluid delivery lumen in the delivery tube.

* * * * *